(12) United States Patent
Ramsey et al.

(10) Patent No.: US 12,146,876 B2
(45) Date of Patent: Nov. 19, 2024

(54) SOLID SUPPORTS FOR DECODING METHODS FOR MULTIPLEXING ASSAYS

(71) Applicant: The University of North Carolina at Chapel Hill, Chapel Hill, NC (US)

(72) Inventors: John Michael Ramsey, Chapel Hill, NC (US); William Hampton Henley, Chapel Hill, NC (US); Thomas Linz, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 486 days.

(21) Appl. No.: 17/244,257

(22) Filed: Apr. 29, 2021

(65) Prior Publication Data

US 2022/0011300 A1    Jan. 13, 2022

Related U.S. Application Data

(62) Division of application No. 15/765,749, filed as application No. PCT/US2016/055407 on Oct. 5, 2016, now Pat. No. 11,016,084.

(60) Provisional application No. 62/237,324, filed on Oct. 5, 2015.

(51) Int. Cl.
*C12Q 1/68* (2018.01)
*G01N 33/542* (2006.01)
*G01N 33/543* (2006.01)

(52) U.S. Cl.
CPC ..... *G01N 33/542* (2013.01); *G01N 33/54313* (2013.01)

(58) Field of Classification Search
CPC .................. G01N 33/542; G01N 33/54313
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,800,159 A | 1/1989 | Mullis et al. | |
| 4,965,188 A | 10/1990 | Mullis et al. | |
| 6,074,827 A | 6/2000 | Nelson et al. | |
| 6,143,496 A | 11/2000 | Brown et al. | |
| 8,222,047 B2 | 7/2012 | Duffy et al. | |
| 8,236,574 B2 | 8/2012 | Duffy et al. | |
| 8,846,415 B2 | 9/2014 | Duffy et al. | |
| 9,110,025 B2 | 8/2015 | Rissin et al. | |
| 9,617,589 B2 | 4/2017 | Ramsey et al. | |
| 9,890,419 B2* | 2/2018 | Geiss .................. | C12Q 1/682 |
| 2005/0130188 A1 | 6/2005 | Walt et al. | |
| 2005/0221373 A1 | 10/2005 | Enzelberger et al. | |
| 2006/0003320 A1 | 1/2006 | Miller et al. | |
| 2006/0008924 A1 | 1/2006 | Anker et al. | |
| 2010/0055721 A1 | 3/2010 | Lambert et al. | |
| 2013/0323716 A1 | 12/2013 | Kartalov et al. | |
| 2014/0272958 A1 | 9/2014 | Ramsey et al. | |
| 2015/0185149 A1 | 7/2015 | Jin et al. | |
| 2015/0211048 A1 | 7/2015 | Ramsey et al. | |
| 2015/0224499 A1 | 8/2015 | Wang et al. | |
| 2018/0136203 A1* | 5/2018 | Walt .................. | G01N 21/78 |
| 2019/0054470 A1 | 2/2019 | Ramsey et al. | |

FOREIGN PATENT DOCUMENTS

| | | |
|---|---|---|
| EP | 1895289 A2 | 3/2008 |
| EP | 2360271 A1 | 8/2011 |
| WO | 9840726 A1 | 9/1998 |
| WO | 0047996 A2 | 8/2000 |
| WO | 0073777 A1 | 12/2000 |
| WO | 0207729 A1 | 1/2002 |
| WO | 02099982 A2 | 12/2002 |
| WO | 2004034012 A2 | 4/2004 |
| WO | 2008122051 A1 | 10/2008 |
| WO | 2013116780 A1 | 8/2013 |
| WO | 2013176767 A1 | 11/2013 |
| WO | 2013188927 A1 | 12/2013 |
| WO | 2014210207 A1 | 12/2014 |
| WO | 2017015529 A1 | 1/2017 |
| WO | 2017065854 A2 | 4/2017 |
| WO | 2017112025 A2 | 6/2017 |
| WO | 2017185098 A1 | 10/2017 |
| WO | 2020068174 A2 | 4/2020 |
| WO | 2020131182 A2 | 6/2020 |

OTHER PUBLICATIONS

Jun et al. (Molecules, 2012, 17:2474-2490) (Year: 2012).*
Extended European Search Report corresponding to European Patent Application No. 21183583.0 (12 pages) (dated Jan. 20, 2022).
Arya et al. "Basic principles of real-time quantitative PCR" Expert Review of Molecular Diagnostics, 5(2):209-219 (2005).
Bouzigues et al. "Biological Applications of Rare-Earth Based Nanoparticles" ACS Nano, 5:8488-8505 (2011).
Chang et al. "Single molecule enzyme-linked immunosorbent assays: Theoretical considerations" Journal of Immunological Methods, 378:102-115 (2012).
Chin et al. "Commercialization of microfluidic point-of-care diagnostic devices" Lab Chip, 12:2118-2134 (2012).
Communication pursuant to Rule 164(2)(b) and Article 94(3) EPC corresponding to European Patent Application No. 16858484.5 (11 pages) (dated Apr. 8, 2019).
Culbertson et al. "Micro Total Analysis Systems: Fundamental Advances and Biological Applications" Analytical Chemistry, 86:95-118 (2014).
Dörre et al. "Techniques for single molecule sequencing" Bioimaging, 5:139-152 (1997).
Hinz et al. "Polymer support for exonucleolytic sequencing" Journal of Biotechnology, 86:281-288 (2001).
Huang et al. "Highly sensitive mutation detection based on digital amplification coupled with hydrogel bead-array" ChemComm, 27:4094-4096 (2009).

(Continued)

*Primary Examiner* — Stephanie K Mummert
(74) *Attorney, Agent, or Firm* — Myers Bigel, P.A.

(57) ABSTRACT

Decoding methods are provided for identifying populations in assays, particularly multiplexing assays and those associated with fluidic devices.

17 Claims, 22 Drawing Sheets

(56) References Cited

OTHER PUBLICATIONS

International Preliminary Report on Patentability corresponding to International Patent Application No. PCT/US2016/055407 (11 pages) (mailed Apr. 19, 2018).
International Search Report and the Written Opinion of the International Searching Authority corresponding to International Patent Application No. PCT/US2019/059773 (14 pages) (mailed Sep. 8, 2020).
International Search Report and the Written Opinion of the International Searching Authority corresponding to International Patent Application No. PCT/US2016/055407 (20 pages) (mailed Aug. 10, 2017).
Kalinina et al. "Nanoliter scale PCR with TaqMan detection" Nucleic Acids Research, 25(10):1999-2004 (1997).
Kingsmore, Stephen F. "Multiplexed protein measurement: technologies and applications of protein and antibody arrays" Nature Reviews Drug Discovery, 5:310-320 (2006).
Leamon et al. "A massively parallel PicoTiterPlate™ based platform for discrete picoliter-scale polymerase chain reactions" Electrophoresis, 24:3769-3777 (2003).
Linz et al. "Photobleaching kinetics-based bead encoding for multiplexed bioassays" Lab on a Chip 17:1076-1082 (2017).
Lizardi et al. "Mutation detection and single-molecule counting using isothermal rolling-circle amplification" Nature Genetics, 19:225-232 (1998).
Manesse et al. "Dynamic microbead arrays for biosensing applications" Lab Chip, 13:2153-2160 (2013).
Margulies et al. "Genome sequencing in microfabricated high-density picolitre reactors" Nature, 437:376-380 (2005).
Miller et al. "Basic Concepts of Microarrays and Potential Applications in Clinical Microbiology" Clinical Microbiology Reviews, 22(4):611-633 (2009).
Nie et al. "An automated integrated platform for rapid and sensitive multiplexed protein profiling using human saliva samples" Lab Chip, 14:1087-1098 (2014).
Nie et al. "Multiplexed Salivary Protein Profiling for Patients with Respiratory Diseases Using Fiber-Optic Bundles and Fluorescent Antibody-Based Microarrays" Analytical Chemistry, 85:9272-9280 (2013).
Osborne et al. "Single-Molecule Analysis of DNA Immobilized on Microspheres" Analytical Chemistry, 72:3678-3681 (2000).
Rissin et al. "Multiplexed single molecule immunoassays" Lab Chip, 13:2902-2911 (2013).
Rissin et al. "Simultaneous Detection of Single Molecules and Singulated Ensembles of Molecules Enables Immunoassays with Broad Dynamic Range" Analytical Chemistry, 83:2279-2285 (2011).
Rissin et al. "Single Molecule Detection: Analytical Applications and Fundamental Studies" Dissertation, Tufts University (183 pages) (Apr. 2007).
Rissin et al. "Single-molecule enzyme-linked immunosorbent assay detects serum proteins at subfemtomolar concentrations" Nature Biotechnology, 28(6):595-599 (2010).
Schuler et al. "Monochrome Multiplexing in Polymerase Chain Reaction by Photobleaching of Fluorogenic Hydrolysis Probes" Analytical Chemistry 88:2590-2595 (2016).
Shen et al. "Multiplexed Quantification of Nucleic Acids with Large Dynamic Range Using Multivolume Digital RT-PCR on a Rotational SlipChip Tested with HIV and Hepatitis C Viral Load" Journal of the American Chemical Society, 133:17705-17712 (2011).
Song et al. "Direct Detection of Bacterial Genomic DNA at Sub-Femtomolar Concentrations Using Single Molecule Arrays" Analytical Chemistry, 85:1932-1939 (2013).
Tan et al. "Monitoring the Reactions of Single Enzyme Molecules and Single Metal Ions" Analytical Chemistry, 69:4242-4248 (1997).
Walt, David R. "Optical Methods for Single Molecule Detection and Analysis" Analytical Chemistry, 85:1258-1263 (2013).
Walt, David R. "Protein measurements in microwells" Lab Chip, 14:3195-3200 (2014).
Wang et al. "Luminescent nanomaterials for biological labelling" Nanotechnology, 17:R1-R13 (2006).
Witters et al. "Digital microfluidics-enabled single-molecule detection by printing and sealing single magnetic beads in femtoliter droplets" Lab Chip, 13:2047-2054 (2013).
Woolley et al. "Emerging technologies for biomedical analysis" Analyst, 139:2277-2288 (2014).
Zammatteo et al. "Comparison between Microwell and Bead Supports for the Detection of Human Cytomegalovirus Amplicons by Sandwich Hybridization" Analytical Biochemistry, 253:180-189 (1997).

* cited by examiner

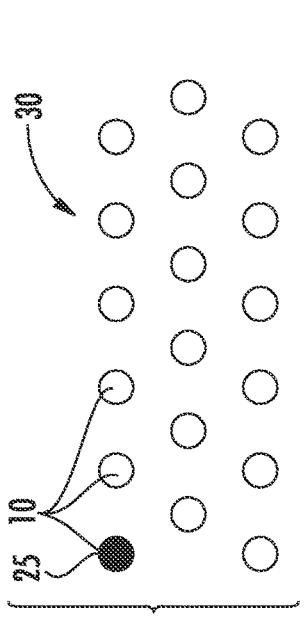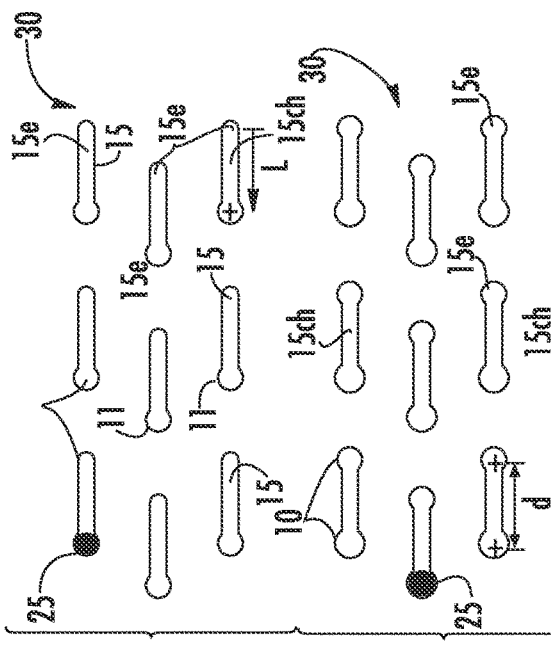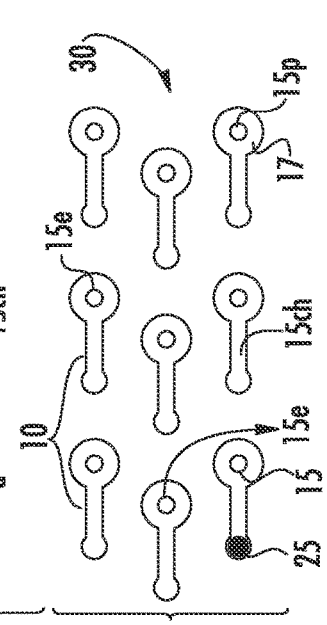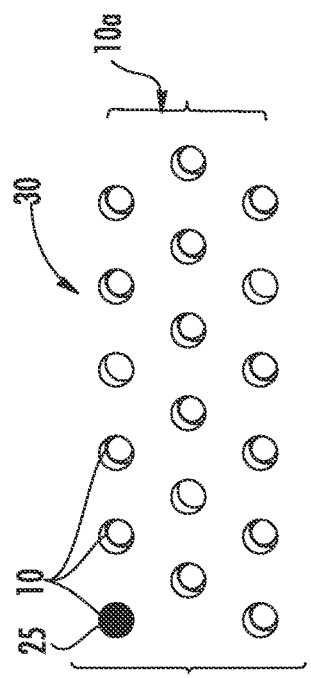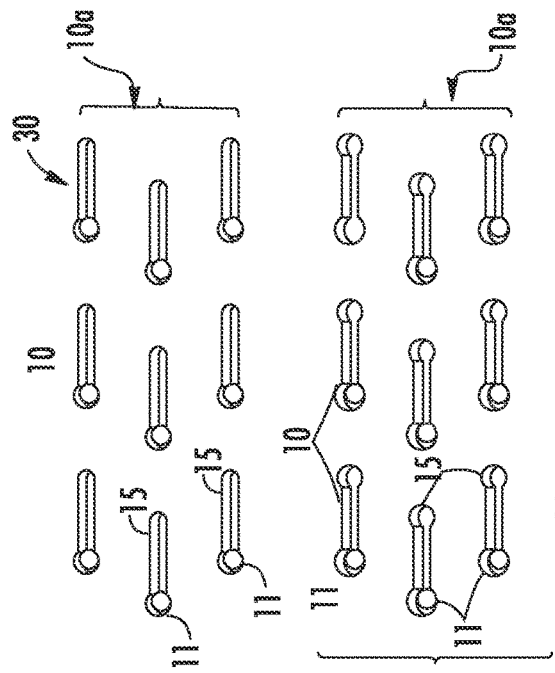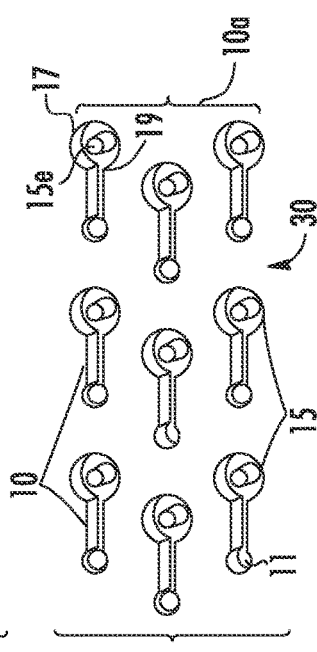
FIG. 9A  FIG. 10A  FIG. 11A  FIG. 12A
FIG. 9B  FIG. 10B  FIG. 11B  FIG. 12B

SOLID SUPPORTS FOR DECODING METHODS FOR MULTIPLEXING ASSAYS

STATEMENT OF FEDERAL SUPPORT

This invention was made with government support under Grant No. HR0011-12-2-0001 awarded by the United States Department of Defense (DARPA). The government has certain rights in the invention.

FIELD OF THE INVENTION

The present invention relates to the analysis of samples and may be particularly suitable for analyses carried out using fluidic devices.

BACKGROUND

The ability to measure low abundance analytes from biological samples is highly important to numerous fields including clinical diagnostics. See, e.g., Rissin et al., Single-molecule enzyme-linked immunosorbent assay detects serum proteins at subfemtomolar concentrations. *Nat. Biotechnol.* 2010, 28, 595-599; Walt, D. R., Optical Methods for Single Molecule Detection and Analysis, *Anal. Chem.* (Washington, D.C., U.S.) 2013, 85, 1258-1263; and Witters et al., Digital microfluidics-enabled single-molecule detection by printing and sealing single magnetic beads in femtoliter droplets, *Lab Chip* 2013, 13, 2047-2054.

Many protein and nucleic acid diagnostic biomarkers are present at low endogenous concentrations requiring that methods for their analysis have very low limits of detection. Increasingly common strategies for performing such sensitive measurements utilize beads functionalized with biorecognition elements (such as antibodies, oligonucleotides, etc.). See, Rissin et al., Simultaneous Detection of Single Molecules and Singulated Ensembles of Molecules Enables Immunoassays with Broad Dynamic Range, *Anal. Chem.* (Washington, D.C., U.S.) 2011, 83, 2279-2285; Song et al., Direct Detection of Bacterial Genomic DNA at Sub-Femtomolar Concentrations Using Single Molecule Arrays, *Anal. Chem.* (Washington, D.C., U.S.) 2013, 85, 1932-1939; Woolley et al., Emerging technologies for biomedical analysis, *Analyst* (Cambridge, U.K.) 2014, 139, 2277-2288; and Culbertson et al., Micro Total Analysis Systems: Fundamental Advances and Biological Applications, *Anal. Chem.* (Washington, D.C., U.S.) 2014, 86, 95-118.

The addition of thousands to millions of microspheres per sample provides high surface area for target capture, thus efficiently and selectively preconcentrating target analytes from large sample volumes. See, Chang et al., Single molecule enzyme-linked immunosorbent assays: Theoretical considerations, *J. Immunol. Methods* 2012, 378, 102-115; and Walt, D. R, Protein measurements in microwells, *Lab Chip* 2014, 14, 3195-3200.

Although this approach is beneficial for measuring various individual analytes, a key advantage of such bead-based methods is the ability to multiplex analyses and quantify numerous targets from a single sample. See, Rissin et al., Multiplexed single molecule immunoassays, *Lab Chip* 2013, 13, 2902-2911; and Kingsmore, S. F., Multiplexed protein measurement: technologies and applications of protein and antibody arrays, *Nat. Rev. Drug Discovery* 2006, 5, 310-320. This can be especially valuable in biological testing applications (e.g. clinical and point-of-care (POC) diagnostics) where a panel of disease biomarkers may be screened in a single test. See, Nie et al., An automated integrated platform for rapid and sensitive multiplexed protein profiling using human saliva samples, *Lab Chip* 2014, 14, 1087-1098; Shen et al., Multiplexed Quantification of Nucleic Acids with Large Dynamic Range Using Multivolume Digital RT-PCR on a Rotational SlipChip Tested with HIV and Hepatitis C Viral Load, *Journal of the American Chemical Society* 2011, 133, 17705-17712; and Chin et al. Commercialization of microfluidic point-of-care diagnostic devices, *Lab Chip* 2012, 12, 2118-2134.

Typical multiplexed bead-based diagnostics methods encode various types of affinity beads with different combinations of dyes at different intensity levels. See, Manesse et al., Dynamic microbead arrays for biosensing applications. *Lab Chip* 2013, 13, 2153-2160; and Nie et al., Multiplexed Salivary Protein Profiling for Patients with Respiratory Diseases Using Fiber-Optic Bundles and Fluorescent Antibody-Based Microarrays. *Anal. Chem.* (Washington, D.C., U.S.) 2013, 85, 9272-9280.

Beads can be decoded by acquiring an image at appropriate excitation/emission wavelengths for each of the encoding dyes used. See, Rissin et al., Multiplexed single molecule immunoassays. *Lab Chip* 2013, 13, 2902-2911. Beads are then assigned to a population based on pre-established fluorescence emission intensity thresholds. See, e.g., Nie et al., Multiplexed Salivary Protein Profiling for Patients with Respiratory Diseases Using Fiber-Optic Bundles and Fluorescent Antibody-Based Microarrays, *Anal. Chem.* (Washington, D.C., U.S.) 2013, 85, 9272-9280. While this approach can produce several populations of encoded beads, it can require that the spectral properties of the different encoding dyes and each of the intensity levels be well resolved to ensure that each bead population can be distinguished from another. Therefore, there is a practical upper limit to the number of multiplexing levels that can be used with this approach, even with specialized equipment such as a flow cytometer. There remains a need for alternate encoding/decoding systems that can allow for increased multiplexing and/or detection speed.

The contents of the documents cited hereinabove in the Background section of the patent application are hereby incorporated by reference as if recited in full herein.

SUMMARY OF EMBODIMENTS OF THE INVENTION

Embodiments of the invention provide decoding measurements of encoded devices, which can provide for additional levels of multiplexing believed to be unattainable by conventional encoding methods.

In contrast to using only single time point encoding measurements, as is typically done for traditional decoding measurements, embodiments of the present application provide methods that employ a time domain to obtain a plurality of decoding measurements taken at different time periods to distinguish and/or identify (decode) different populations. The decoding measurements can be based on encoding agents (e.g., dyes), such as, for example, encoding agents with similar spectral properties.

The encoding agents can have similar spectral properties such that they may be indistinguishable in a first image (e.g., before a defined event), and can include one that is stable (e.g., produces the same fluorescence intensity at different points in time both before and after a defined event) and one that is physically and/or chemically changed in response to a defined event (e.g., exhibits an increase or decrease in fluorescence intensity at different points in time after the defined event compared to the fluorescence intensity before the defined event and/or is selectively activated).

The encoding agents can include stable, partially stable, relatively stable and unstable agents.

Some or all of the encoding agents can include similar spectral properties such that they may be indistinguishable in a first image and the unstable encoding agent can generate a reduced or an increased fluorescence intensity due to a physical and/or chemical change, which may be caused by exposure to a defined event (e.g., a thermal, optical, chemical, magnetic, and/or electrochemical event).

Decoding measurements can be taken at different points in time, including before, during, and/or after a defined event that causes a physical and/or chemical change associated with a respective solid support (which may be all or a portion thereof), which can cause the encoding signal for the respective solid support (which may be all or a portion thereof) to change (e.g., the luminescence intensity generated by the respective solid substrate (which may be all or a portion thereof) with at least one encoding agent may change). In some embodiments, luminescence intensity may be measured, which may include fluorescence and/or phosphorescence intensity. Other decoding measurements of a solid support include detecting a change in magnetic behavior, pH, light scattering, physical size, shape, refractive index, solubility, light absorbance and/or emission intensity or maxima wavelengths shifts, conductivity, dielectric constant, viscosity, and radioactive decay events, and combinations of the above.

For example, in some embodiments, solid supports such as, but not limited to, beads, can be encoded with an encoding agent (e.g., dye or dyes), and where more than one encoding agent is used, the encoding agents may have similar spectral properties (e.g., similar initial spectral properties), but different stabilities. Although indistinguishable by conventional decoding methods, the methods of the present invention can allow different populations of solid supports to be resolved. In some embodiments, to identify at least two different populations, at least two different encoding agents may be used. Alternatively or in addition, in some embodiments, one encoding agent (e.g. the same dye and/or active moiety) may be used to identify at least two different populations, but for at least one of the populations the encoding agent, in response to a defined event, provides a different encoding signal than the other such that the population can be identified, which may, for example, be that the encoding agent includes an element that is not present in the other and that is selectively activated or changed in response to the defined event. For example, the encoding agents for two different populations may include the same dye, but may be attached to a solid support differently and one attachment method may include a bond that is disrupted by a defined event, which changes the fluorescence intensity of the encoding agent or of the solid support.

Solid supports of the present invention can yield many more distinct encoding states than can be achieved with static, single time-point measurements.

Methods of the present invention can identify increased populations with additional encoding signals provided by a physical and/or chemical change associated with the solid support, which can cause the encoding signal for a respective solid support and/or portion thereof to change over time, typically based on a defined event, such as, for example, the defined event causing a change in a chemical and/or physical property of an encoding agent and/or solid substrate.

The increased multiplexing capabilities may not require additional filter sets or other costly optical equipment, which can provide a low cost, relatively simple analytical platform.

While there are many ways to implement time-dependent measurements in and/or on a solid substrate (e.g., bead), photostability and/or thermal stability may be particularly suitable parameters to exploit to identify multiplexed beads.

In some embodiments, first and second encoding signals of a respective solid support (which may be all or a portion thereof) can be obtained and analyzed to identify different populations. In some embodiments, the first encoding signal can be based on and/or obtained from a first image with different solid supports in different locations. The second encoding signal can be based on and/or obtained from a second image with the different solid supports in the corresponding (same) locations. In some embodiments, the first encoding signal can be based on and/or obtained from a first image with encoded molecular recognition elements in different locations on and/or in a sample on a solid support, and the second encoding signal can be based on and/or obtained from a second image with the different encoded molecular recognition elements in the corresponding (same) locations. The actual number of different encoding signals in the first and second images can be the same. However, the encoding signal of respective solid support(s) can change over time (e.g., shift from one level into another, such as high to low or vice versa), which can increase the number of detectable encoding states.

For example, in some embodiments, an analysis system can be configured to detect the same number of defined intensity levels between the first and second images, such as, for example, three (3) intensity levels (low, med, high). However, due to a change in the intensity level between the first and second images for at least some of the populations, additional populations can be defined based on populations that remained the same and populations that changed (1. initial low intensity and stayed at low intensity, 2. initial medium intensity and bleached to low intensity, 3. initial medium intensity and stayed at medium intensity, 4. initial high intensity and bleached to low intensity, 5. initial high intensity and bleached to medium intensity, 6. initial high intensity and stayed at high intensity).

Further, employing the ability to get brighter as a quencher is eliminated or a caged dye is released, an analysis system can be configured to detect all of 1-6 above, plus 7. initial low intensity that increased to medium intensity, 8. initial low intensity that increased to high intensity, 9. initial medium intensity that increased to high intensity. That is, 9 populations from only 3 intensity levels. If a second dye set (e.g., encoding agent) is used, one can yield 81 populations.

Other encoding signals can be employed including physical and/or chemical changes of a solid substrate as will be discussed further below.

In some embodiments, a method of decoding solid supports is provided, the method including: detecting a first encoding signal and a second encoding signal for solid supports in a plurality of solid supports (e.g., a multiplexing bead set); comparing the first encoding signal and the second encoding signal for a respective solid support in the plurality of solid supports, wherein the second encoding signal for the respective solid support is detected during or after at least one chemical and/or physical change associated with the solid support and the first and second encoding signals for the respective solid support are different; and decoding the plurality of solid supports based at least in part on the comparison of the first and second encoding signals.

In some embodiments, a method of decoding a solid support is provided, the method including providing a plurality of molecular recognition elements (such as, e.g., antibodies, aptamers, and/or nucleic acid probes), wherein at least some of the plurality of molecular recognition elements including one or more encoding agents; binding at least a portion of the plurality of molecular recognition elements to at least a portion of a sample on the solid support; detecting a first encoding signal and a second encoding signal for molecular recognition elements in the plurality of molecular recognition elements; comparing the first encoding signal and the second encoding signal for a respective molecular recognition element in the plurality of molecular recognition elements, wherein the second encoding signal for the respective molecular recognition element is detected during or after at least one chemical and/or physical change associated with the molecular recognition element and the first and second encoding signals for the respective molecular recognition element are different; and decoding the plurality of molecular recognition elements based at least in part on the comparison of the first and second encoding signals. The solid support may be a microscope slide holding a biological sample such as, e.g., a tissue section. In some embodiments, the solid support may be a glass, silicon, or plastic slide holding arrays of proteins and/or nucleic acids involved in a direct or sandwich type of assay.

Some embodiments include a method of decoding a sample, including detecting a first encoding signal and a second encoding signal for encoded elements (e.g., encoded solid supports and/or encoded molecular recognition elements) in a plurality of encoded elements; comparing the first encoding signal and the second encoding signal for a respective encoded element in the plurality of encoded elements, wherein the second encoding signal for the respective encoded element is detected during or after at least one chemical and/or physical change associated with the encoded element and the first and second encoding signals for the respective encoded element are different; and decoding the plurality of encoded elements based at least in part on the comparison of the first and second encoding signals.

Other embodiments are directed to analysis systems. An assay decoding system may be provided including a circuit comprising at least one processor; a fluidic analysis chip comprising a plurality of solid supports (e.g., a multiplexing bead set); and a source in communication with the plurality of solid supports, wherein the circuit activates the source to cause at least one detectable physical and/or chemical change associated with at least some of the plurality of solid supports and compares first and second encoding signals for a respective solid support in the plurality of solid supports to decode different populations of solid supports in the plurality of solid supports. The source may include at least one of a thermal source or a light source in communication with the plurality of solid supports, wherein the circuit activates the at least one of the thermal source or the light source to cause at least one detectable physical and/or chemical change associated with at least some of the plurality of solid supports.

In some embodiments, the system may include a controller, a detector in communication with the controller, an image processor with a module configured to identify signal present in signal detection segments of reaction wells of a device holding the reaction wells at different points in time for a single sample, and a dynamic decoding module.

The reaction wells can have at least one bead retention segment

The module can be configured to identify a positive assay signal after a reaction and later before and after at least one defined event.

The module can be configured to carry out multiplexed bead decoding based on identified positive assay signals after a reaction event and before and after a defined event.

Centerlines of bead wells holding respective beads can be spaced apart at a distance of between 0.2 and 1000 μm.

Further aspects of the invention include a plurality of solid supports (e.g., a multiplexing bead set) including a first population of solid supports including at least one encoding agent at a first concentration and/or ratio; and a second population of solid supports including the at least one encoding agent at a second concentration and/or ratio and at least one additional encoding agent, wherein a fluorescence excitation and emission wavelength for the at least one encoding agent and the at least one additional encoding agent overlap, and wherein the first and second concentrations of the at least one encoding agent are different and the different concentrations and/or ratios of the at least one encoding agent on respective solid supports in the first and second populations provide a plurality of encoding states.

A further aspect of the present invention includes a plurality of encoded molecular recognition elements, wherein the plurality of encoded molecular recognition elements includes a first population of molecular recognition elements including at least one encoding agent at a first concentration and/or ratio; and a second population of molecular recognition elements comprising the at least one encoding agent at a second concentration and/or ratio and at least one additional encoding agent, wherein a fluorescence excitation and emission wavelength for the at least one encoding agent and the at least one additional encoding agent overlap, and wherein the first and second concentrations of the at least one encoding agent are different and the different concentrations and/or ratios of the at least one encoding agent on respective molecular recognition elements in the first and second populations provide a plurality of encoding states.

In some embodiments, an encoded molecular recognition element includes two or more (e.g., 2, 3, 4, or more) encoding agents.

Another aspect of the present invention is directed to a kit comprising a plurality of solid supports as described herein.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 3A shows that the initial fluorescence intensities for each bead population were similar. FIG. 3B shows that the populations were easily resolved after prolonged photoexposure. FIGS. 3A and 3B are shown at identical brightness/contrast settings of the camera. FIG. 3C illustrates a map depicting the position and identity of individual phycoerythrin PE (solid), quantum dots QD (small dots), and Mix (stripes) encoded beads in the array wells.

FIG. 9A is a top view of a microfluidic device with a conventional bead well array.

FIG. 9B is a side perspective view of the conventional bead wells shown in FIG. 9A.

FIG. 10A is a top view of an exemplary bead well array according to embodiments of the present invention.

FIG. 10B is a side perspective view of the bead wells shown in FIG. 10A.

FIG. 11A is a top view of another exemplary bead well array according to embodiments of the present invention.

FIG. 11B is a side perspective view of the bead wells shown in FIG. 11A.

FIG. 12A is a top view of yet another bead well array according to embodiments of the present invention.

FIG. 12B is a side perspective view of the bead wells shown in FIG. 12A.

DETAILED DESCRIPTION OF EMBODIMENTS OF THE INVENTION

Figure 1A:
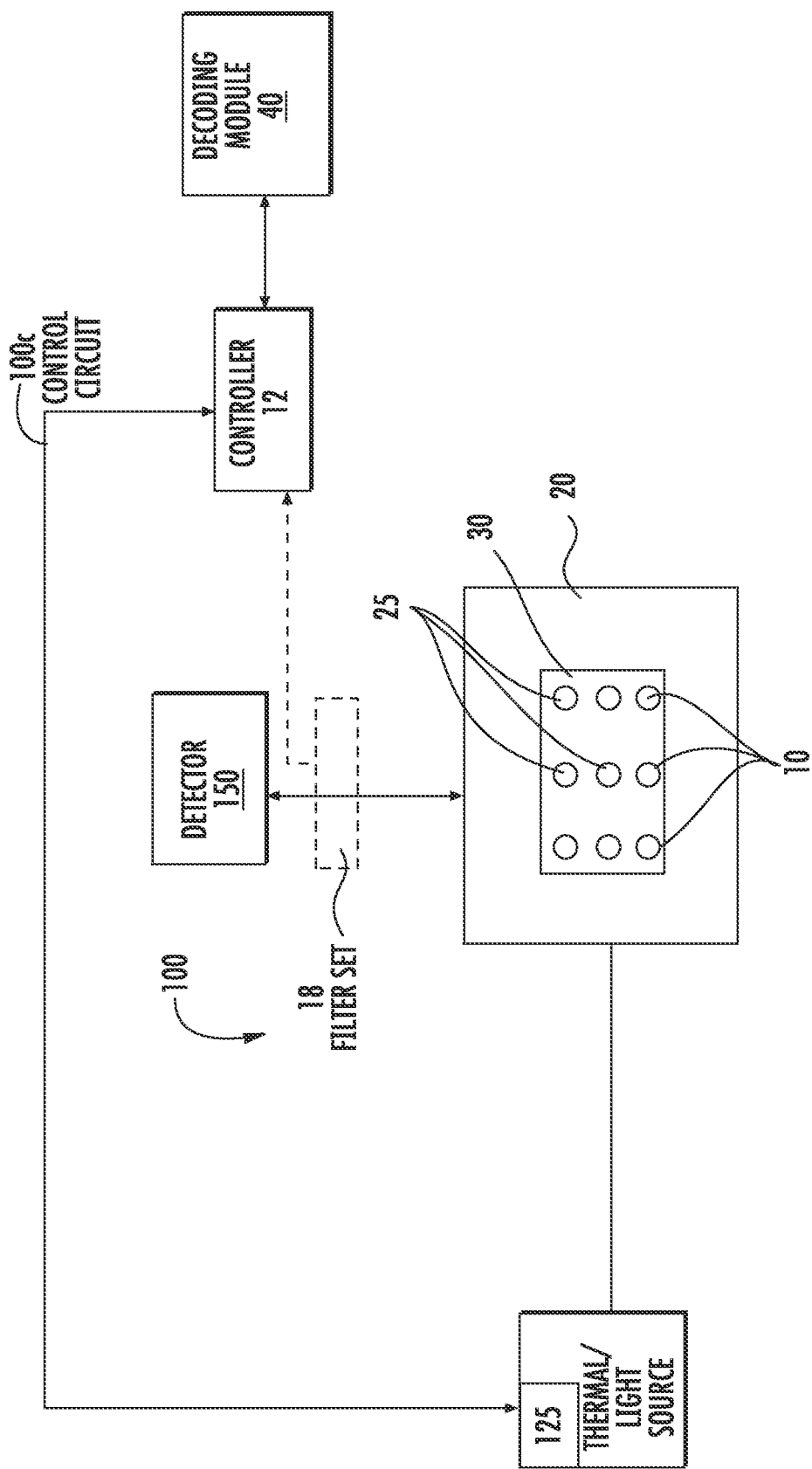
FIG. 1A is a schematic illustration of an analysis system according to embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The abbreviations "FIG. and "Fig." for the word "Figure" can be used interchangeably in the text and figures.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The terms "microchip" and "microfluidic chip" are used interchangeably and refer to a substantially planar, thin device. The microfluidic chip can be rigid, semi-rigid or flexible. The term "thin" refers to a thickness dimension that is 10 mm or less such as between 10 mm and 0.1 mm, and can be about 3 mm, about 2.5 mm, about 2 mm, about 1.5 mm, about 1 mm, or about 0.5 mm. The microchip typically has a width and length that is less than about 6 inches, more typically between about 1 inch and 6 inches. The microchip can have a width dimension that is less than a length dimension. The microfluidic chip can have a width dimension that is about 2.13 inches (54 mm) and a length dimension that is about 3.4 inches (85.5 mm), in some embodiments. The microchip can include micro-sized and/or nano-sized fluidic channels.

The term "primary dimension" refers to a width and/or depth dimension of a fluidic channel.

The terms "micro-sized" and "microfluidic" with respect to a fluidic channel refer to a fluid flow channel that has sub-millimeter or smaller size width and/or depth (e.g., the term includes micrometer and nanometer size channels) and includes channels with at least a segment having a width and/or depth in a size range of hundreds of microns or less, typically less than 900 microns and greater than 1 nm. A fluidic channel or portion thereof may include a nanochannel having a primary dimension between 1 nm and about 900 nm, more typically between about 10 nm and 500 nm.

A channel of bead wells of a bead well array can have sidewalls and a floor formed into one or more substrates to have an open top surface and a closed bottom surface with the sidewalls extending therebetween. One or more spacers, top substrates, membranes or covers may be used. The top substrate, membrane or cover can seal, cover or otherwise close the upper surface of a fluidic channel(s) and/or array of reaction wells. The term "about" refers to parameters that can vary between +/−20% or less, such as, e.g., +/−10% or 5%.

The term "solid support" includes one or more of an object such as, e.g., a microbead, chip, plate, slide, pin, plate well, bead, microsphere, nanoparticle, microwell or other member that may be used to provide a probe and/or primer and/or that may be coupled to or labeled with an encoding agent (such as, e.g., a fluorescent compound, a chemiluminescent compound, a radioactive element, and/or an enzyme) and/or a dynamic element. An encoding agent and/or a dynamic element may be directly or indirectly attached to a solid support, such as, for example, by covalent attachment, noncovalent attachment, and/or physical incorporation. In some embodiments, a solid support may be a printed array on a solid surface. In some embodiments, a solid support may be a microsphere. In some embodiments, a solid support may be a solid surface on which a sample, such as, e.g., a chemical and/or biological component (e.g., a tissue sample), is provided and a molecular recognition element comprising one or more encoding agent(s) may be attached to a portion of the sample. The molecular recognition element may comprise or may be an antibody, aptamer, DNA hybridization probe, oligonucleotide, peptide, protein, and/or combinations thereof. In some embodiments, a solid support may comprise a labile reagent and/or support bond, each of which may allow for cleavage from the solid support. In some embodiments, one or more encoding agents may be attached to a solid support (e.g., a bead or microsphere) to provide an encoded solid support (e.g., an encoded bead or encoded microsphere). In some embodiments, one or more encoding agents may be attached to a molecular recognition element (e.g., an antibody) to provide an encoded molecular recognition element (e.g., an encoded antibody). In some embodiments, an encoded molecular recognition element may be attached to a particle and/or may attach to a particle, such as, for example, a nanoparticle. In some embodiments, an encoded molecular recognition element may attach to a solid surface on which a sample is provided due to the binding affinity of the encoded molecular recognition element to an element in and/or on the sample on the solid surface. Thus, in some embodiments, an encoding agent may not be attached to a solid support until an assay is begun or complete or unless the encoded molecular recognition element binds to an element on and/or in a sample on a solid support. Accordingly, methods of the present invention may include providing or binding one or more encoding agents onto a solid support. In some embodiments, methods of the present invention comprise providing a plurality of encoded molecular recognition elements and binding at least a portion of the encoded molecular recognition elements to a sample on a solid support. In some embodiments, methods of the present invention may be used in fluorescence microscopy applications including, for example, immunofluorescence mapping of tissues, cells, and/or receptors and/or fluorescence in situ hybridization (FISH).

The term "bead" or "beads" refers to solid phase members such as particles, granules or microspheres, typically magnetic microspheres, that can be porous, superficially porous, or nonporous of material(s) such as, e.g., polymers, plastics, glass, silicon dioxide, metal or semimetal oxides (including but not limited to aluminum oxides, titanium oxides, zirconium oxides or other oxides), quantum dots, metal particles, and/or the like, which may be appropriate for use in the reaction wells. In some embodiments, a multiplexing bead set may be provided comprising a plurality of beads (e.g., microspheres) that are uniquely encoded to distinguish one population of beads from another.

The term "circuit" refers to an entirely hardware embodiment or an embodiment combining software and hardware.

The analyte in a sample can be any analyte of interest from a sample including, for example, various mixtures including synthetic and/or biological macromolecules, nanoparticles, small molecules, DNA, nucleic acids/polynucleic acids, peptides, proteins and/or the like. The analyte can be one or more analyte molecules. The sample or analyte of a sample can include one or more polar metabolites such as, e.g., amino acids and/or charged molecules, peptides, and/or proteins. The sample and/or analyte may also or alternatively include molecules extracted from biofluids, blood, serum, urine, dried blood, cell growth media, lysed cells, beverages and/or food. The sample may also or alternatively include environmental samples such as water, air and/or soil.

The term "oligonucleotide" refers to a nucleic acid sequence of at least about five nucleotides to about 500 nucleotides (e.g., 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 50 nucleotides, or about 20 nucleotides to about 25 nucleotides, which can be used, for example, as a primer in a polymerase chain reaction (PCR) amplification assay and/or as a probe in a hybridization assay or in a microarray. Oligonucleotides of this invention can be natural or synthetic, e.g., DNA, RNA, PNA, LNA, modified backbones, etc., or any combination thereof as are well known in the art.

Probes and primers, including those for either amplification and/or detection, can comprise oligonucleotides (including naturally occurring oligonucleotides such as DNA and synthetic and/or modified oligonucleotides) of any suitable length, but are typically from 5, 6, or 8 nucleotides in length up to 40, 50 or 60 nucleotides in length, or more.

Probes and/or primers may be immobilized on or coupled to a solid support such as, e.g., a bead, chip, pin, or microtiter plate well, and/or coupled to or labeled with an encoding agent such as, e.g., a fluorescent compound, a chemiluminescent compound, a radioactive element, and/or an enzyme.

The term "encoding agent" refers to one or more agents (e.g., chemicals, proteins, etc.) associated with (e.g., applied to, attached to, bound to, compounded with, used to fabricate or create, etc.) a solid support and/or a material of the solid support and/or a material in contact with the solid support that provide and/or will generate an encoding signal for the respective solid support (which may be all or a portion thereof). In some embodiments, one or more encoding agents provide and/or generate a detectable encoding signal that allows for differentiation of a solid support (e.g., bead) population or subpopulation. For example, in some embodiments, one or more encoding agents may provide and/or generate a detectable encoding signal for an individual solid support (e.g., a bead) to which the one or more encoding agents are attached and/or one or more encoding agents may provide and/or generate a detectable encoding signal for a particular portion of a solid support to which the one or more encoding agents are attached (e.g., the portion of the solid support to which a molecular recognition element comprising the one or more encoding agents binds).

An encoding signal may be provided and/or generated by one or more encoding agents associated with a solid support and/or by the solid support itself and/or a material (e.g., compound) associated with the solid support. In some embodiments, the encoding signal is a signal (e.g., an optical and/or electrical signal) that is generated by one or more encoding agents (e.g., chemicals, proteins, etc.) associated with (e.g., applied to, attached to, bound to, compounded with, used to fabricate or create, etc.) a solid support and/or by the solid support. A detectable encoding signal may be optically and/or electronically detectable, which may be perceived visually with the human eye and/or electronically read, detected, and/or obtained. The detectable encoding signal can comprise intensity, typically at or above a defined threshold value, a color (e.g., color hue, color intensity, and/or color value), a color and intensity, and/or a change in size, shape, and/or radioactivity. In some embodiments, the detectable encoding signal comprises a luminescence intensity, which may include a fluorescence, phosphorescence, and/or chemiluminescence intensity.

The encoding signal for a respective solid support (which may be all or a portion thereof) may be detectable (e.g., detectable optically, electronically, electrochemically, electrostatically, magnetically, etc.) or may not be detectable. In some embodiments, the encoding signal for a respective solid support (which may be all or a portion thereof) may change. For example, the encoding signal for a respective solid support may change from detectable to not detectable, from not detectable to detectable, from a greater value to a lower value (e.g., from a greater signal amplitude, fluorescence intensity value, diameter, etc.), and/or from a lower value to a greater value. The change in an encoding signal for a respective solid support may occur over time and/or may occur due to at least one chemical and/or physical change associated with the solid support. In some embodiments, an encoding signal for a solid substrate may change and/or may be provided and/or generated by a change in the environment in which the solid support is present (e.g., a change in a solution in which the solid support and/or encoding agent is in contact with). For example, an encoding signal for a solid support may change and/or may be provided and/or generated by a change in magnetic behavior, pH, light scattering, physical size (increase or decrease), shape, refractive index, solubility, light absorbance and/or emission intensity or maxima wavelengths shifts, conductivity, dielectric constant, viscosity, and radio emission from isotopic decay, and combinations of the above.

"Encoding state" refers to a particular combination of encoding signals (detectable or not detectable) for a respective solid support in a plurality of solid supports, such as, for example two or more encoding signals for a particular solid support at two or more points in time, and/or to a particular combination of encoding signals (detectable or not detectable) for a particular portion of a solid support (e.g., a specific area or part of a sample on the solid support providing the particular combination of encoding signals). For a respective solid support, the particular encoding signal at two or more points in time may allow for differentiation and/or identification of a particular population or sub-population (e.g., a particular solid support (e.g., bead) population or sub-population). In some embodiments, the particular encoding signal for the respective solid support at two or more points in time may be the same and/or may be different. Each encoding state may be unique from another encoding state and/or detectable (e.g., optically and/or electronically) and distinguishable from another encoding state to provide distinguishable populations. However, an encoding signal at a first point in time for a respective population may be the same as the encoding signal at the first point in time for a different population, but at a second point in time the encoding signals for the two populations may be different, such that the two populations may be distinguished and/or identified. In some embodiments, the encoding signal for a first population and second population may start out at different levels (e.g., have different signal amplitudes or values) but end up at the same level.

The term "decoding" refers to (typically electronic/programmatic) identification of different populations of a respective sample (including e.g., a sample of solid supports and/or a sample comprising a plurality of encoded molecular recognition elements) based at least in part on the encoding signal from encoded solid support(s) and/or encoded molecular recognition elements. In some embodiments, decoding is based at least in part on comparing two or more encoding signals for a respective solid support (which may be all or a portion thereof) before, during and/or after at least one chemical and/or physical change associated with the respective solid support and/or by comparing two or more encoding signals at different points in time. In some embodiments, decoding is based at least in part on comparing two or more encoding signals for an individual solid support before, during and/or after at least one chemical and/or physical change associated with the individual solid support and/or by comparing two or more encoding signals for the individual solid support at different points in time. For example, a sample comprising a plurality of solid supports may comprise 6 different populations and, thus, 6 different encoding states. Detection and/or identification of one or more encoding signals can allow for the decoding of the sample to determine the identity of the particular solid support population. In some embodiments, decoding is based at least in part on comparing two or more encoding signals for a particular portion of a solid support (e.g., a specific area or part of a sample on the solid support) before, during and/or after at least one chemical and/or physical change associated with that portion of the solid support and/or by comparing two or more encoding signals for that portion of the solid support at different points in time. Different encoded molecular recognition elements may provide a plurality of encoding states and detection and/or identification of one or more encoding signals can allow for the decoding of the sample to determine the identity and/or location of a particular population, such as, e.g., the identity and/or location of an element that binds the encoded molecular recognition element for particular population.

The term "dynamic decoding" or "time-domain encoding", referred to interchangeably herein, refer to the (typically automated) analysis of encoding signals of a sample (including e.g., a sample of solid supports and/or encoded molecular recognition elements) based on a plurality (e.g., 2 or more) of measurements (typically from images) to obtain encoding signals of the solid support(s) over time. Different populations (e.g., populations of solid supports or molecular recognition elements) in the sample can have respective encoding signals that can change over time. The change can be used to identify populations. For example, in some embodiments, time-domain encoding may incorporate photobleaching kinetics to decode different populations. By incorporating the time domain, time-domain encoding can unlock additional multiplexing levels that are unattainable by conventional decoding methods.

Two or more measurements (e.g., 2, 3, 4, 5, 6, etc.) may be taken to obtain two or more encoding signals (e.g., 2, 3, 4, 5, 6, etc.) for respective solid supports in a sample comprising a plurality of solid supports and/or for a respective solid support with at least one portion of the solid support providing the two or more encoding signals. In some embodiments, a first encoding signal measurement can be taken at a first point in time and a second encoding signal measurement can be taken at a second point in time. The first encoding signal measurement(s) can be based on a first image that is taken at the first point in time (e.g., before, during or after an assay is carried out e.g., after a hybridization reaction) and/or on the detection of an optical or electrical signal obtained at the first point in time. The second encoding signal measurement may be obtained after or later than the first point in time. In some embodiments, the second encoding signal measurement and one or more subsequent measurements may be taken after any exited state lifetime of a compound (e.g., an encoding agent) associated with the solid support and/or at a time greater than 1 ms (e.g., 10 ms, 100 ms, or 1, 2, 3, 4, 5 second(s)) after the immediately preceding measurement. The second encoding signal measurement can be based on a second image taken at the second point in time and/or on the detection of an optical or electrical signal obtained at the second point in time. The two or more encoding signal measurements may be taken and/or obtained to detect the encoding signal at a point in time (e.g., at a first and second point in time) for a specific solid support in the sample of solid supports.

In some embodiments, an encoding signal measurement may be taken and/or obtained before, after, and/or during a Defined Event. The term "Defined Event" means a planned event that can cause or result in a physical and/or chemical change associated with a solid support. The Defined Event can be passive or dynamic. In some embodiments, a Defined Event may cause or result in a physical and/or chemical change in a dynamic element. In some embodiments, a Defined Event may cause or result in a physical and/or chemical change in an encoding agent (e.g. a dye, protein, etc.) and/or a solid support (e.g., a microsphere).

A "dynamic element" as used herein refers to a chemical and/or biological compound that provides or exhibits a physical and/or chemical change in response to a Defined Event. The physical and/or chemical change may modify the encoding signal for a respective solid support (which may be all or a portion thereof) at a point in time compared to the encoding signal at a different (e.g., earlier) point in time and may be detectable (e.g., optically and/or electrically detectable). A "dynamic element" may include an encoding agent (e.g. a dye, protein, etc.) and/or a solid support (e.g., a microsphere). The physical and/or chemical change may be a physical and/or chemical change that affects a solid support (e.g., the change may be a change in the charge and/or color of a solid support and/or may be a change in the size and/or shape of a solid support). Thus, the dynamic element may be the solid support and/or a compound attached and/or associated with the solid support. In some embodiments, the physical and/or chemical change is a physical and/or chemical change that affects an encoding agent associated with the solid support (e.g., the change may be in the stability of a linker binding the encoding agent to the solid support, the solvent accessibility of an encoding agent, and/or the presence and/or absence of a quencher). Thus, the dynamic element may be the encoding agent and/or a compound attached to and/or associated with the encoding agent (e.g., a quencher). The physical and/or chemical change may be reversible or irreversible. In some embodiments, the dynamic element may be an encoding agent. In some embodiments, a Defined Event may selectively activate or deactivate an encoding agent. Example Defined Events are provided in Table 1.

TABLE 1

Example Defined Events.

Addition/removal of a ligand, base pairing, quencher, etc. that effects a chemical binding and/or cleavage
pH change
Photobleaching/Photoactivation
Solvent environment change
Protein/nucleic acid conformation/shape change (via complex formation or disruption, breakage of disulfide bonds, denaturation, etc.)
Interaction with another chemical species that results in an observable change
Thermal event (hot or cold)
Pressure change
Passage of time greater than 1 ms (e.g., greater than 10 ms, 1 second, etc.) and/or a passage of time after any exited state lifetime of a compound associated with the solid supports One or more Defined Events may be used to decode a solid support and/or a plurality of solid supports, and an encoding signal for a respective solid support (which may be all or a portion thereof) may or may not change in response to each of the one or more Defined Events. The Defined Event may not be one that typically occurs in an assay and/or analysis in which the solid support(s) are used in. In some embodiments, the Defined Event is an event (e.g., a heating or light exposure) that occurs during an assay in which the solid support(s) are used in. A Defined Event may force a chemical and/or physical change in a portion of the solid support(s) (e.g., optionally in an encoding agent attached to and/or associated with the solid support), which can result in a change in the encoding signal for that portion of the solid support(s) that is associated with a particular encoding state. Example static encoding signals and time-domain encoding signals are provided in Table 2. In some embodiments, a static encoding signal may be used to decode at least one population in a sample in addition to one or more time-domain encoding signals.

TABLE 2

Example static encoding signals and time-domain encoding signals.

| Static Encoding Signals: | Time-domain Encoding Signals: |
|---|---|
| Absorbance/Emission maxima wavelengths | A change in Absorbance/Emission maxima wavelengths |
| Emission Intensity | A change in Emission Intensity |
| Shape | A change in Shape (cube to sphere, etc.) |
| Size | A change in Size (shrinkage, swelling, dissolution) |
| Magnetic Properties | A change in Magnetic Properties |
| Presence of Radioactivity | A change in Radioactivity (via natural decay or removal of the radioisotope) |
| pH | A change in pH |
| Degree of Light Scattering | A change in the Degree of Light Scattering |
| Refractive Index | A change in Refractive Index |
| Conductivity | A change in Conductivity |
| Dielectric Constant | A change in Dielectric Constant |
| Any of the above | Solubility (measured by a change of a static encoding parameter) |

An encoding signal is not to be confused with an assay dye signal, if present, and the dynamic element, encoding agent, and Defined Event should be configured and/or selected so that they do not interfere with the assay. In some embodiments, if a dye is utilized in an assay for which dynamic decoding is utilized, then the assay dye may be distinguishable from the one or more dynamic elements and/or encoding agents used in the dynamic decoding. For example, the assay dye signal may be spectrally shifted from the signal associated with the dynamic element's signal and/or encoding agent's signal and/or the assay dye may use a detectable parameter different than the encoding agent(s) and/or dynamic element(s). Alternatively, the encoding agent and/or dynamic element may be spectrally similar and/or of the same magnitude and/or intensity of the assay dye; however, in such a case the Defined Event can cause a change in the encoding agent signal and/or dynamic element signal such that it is no longer spectrally similar and/or of the same magnitude and/or intensity of the assay dye and thus is distinguishable from the assay dye and/or no longer interferes with the assay.

The same solid support in the same device (e.g., fluidic device, typically the same beads which may be in the same reaction wells or virtual arrays), may be used for the first and second images or for detecting the first and second optical and/or electrical signals. The encoding agents and/or dynamic elements for the different images can have similar spectral properties.

A Defined Event may cause and/or result in one or more physical and/or chemical changes associated with a solid support. In some embodiments, a Defined Event may cause and/or result in a change in an environment of the solid support, which can, in response, cause or induce a physical and/or chemical change in a dynamic element (e.g., an encoding agent and/or solid support) to provide a change in the encoding signal for the solid support (e.g., a change in the encoding signal for a particular solid support in a plurality of solid supports or a change in the encoding signal for a particular portion of a solid support, the solid support containing a plurality of encoding signals at different portions of the solid support), which can be visually and/or electronically detected (if the latter, the detection can be via an optical or electrical detector).

Time-domain encoding may comprise comparing an encoding signal for a respective solid support at a particular point in time (e.g., prior to the Defined Event) to an encoding signal for the respective solid support at a different point in time (e.g., after the Defined Event) to identify the particular population the encoding signal and/or solid support belongs to. In some embodiments, a first encoding signal for a respective solid support is obtained in a first reading (e.g., detection of an optical or electrical signal) and/or first image before or during a Defined Event and at least one second reading and/or second image is obtained after the first image to obtain a second encoding signal for the respective solid support. The first and/or second reading and/or image may comprise multiple different encoding signals that correspond to discrete solid supports or to discrete locations of and/or entities on and/or in a sample on a solid support. The different encoding signal measurements and/or images can be obtained from a common detector, e.g., when the fluidic device and/or solid supports of the fluidic device is or are held at the same temperature and the detector is operated at the same wavelength during an analysis of a sample. The different encoding signal measurements and/or images may be obtained within about 1 microsecond to about 50 hours of each other, and in some embodiments between about 1 ms to about 10 minutes of each other (e.g., 1 second to 1 minute or 1 second to about 10 minutes of each other).

Two or more (e.g., 2, 3, 4, 5, 6, etc.) encoding signal measurements and/or images may be obtained before, during and/or after one or more Defined Event(s) and/or one or more physical and/or chemical change(s) associated with a solid support. The encoding signal measurements and/or images may be obtained using one or more wavelength bands (e.g., 1, 2, 3, 4, 5, etc.). In some embodiments, two or more encoding signal measurements and/or images may be obtained before a Defined Event and/or at least one physical and/or chemical change associated with a solid support. For example, a first image may be obtained in a blue excitation wavelength band, a second image may be obtained in a green excitation wavelength band, and a third image may be obtained in a red excitation wavelength band, with each of the first, second and third images being obtained before a Defined Event and/or at least one physical and/or chemical change associated with a solid support. In some embodiments, two or more encoding signal measurements and/or images may be obtained during and/or after a Defined Event and/or at least one physical and/or chemical change associated with a solid support. For example, an image may be obtained in each of the following: a blue excitation wavelength band, a green excitation wavelength band, and a red excitation wavelength band, with each of the three images being obtained during and/or after a Defined Event and/or at least one physical and/or chemical change associated with a solid support. Thus, embodiments of the present invention may include obtaining multiple encoding signal measurements and/or images that may be obtained in multiple wavelength bands. In some embodiments, two or more encoding signal measurements and/or images may be obtained before, during and/or after two or more Defined Event(s) and/or two or more physical and/or chemical change(s) associated with a solid support. For example, a first image may be taken before a first Defined Event and/or a first physical and/or chemical change associated with a solid support, a second image may be taken after the first Defined Event and/or the first physical and/or chemical change associated with a solid support, and a third image may be taken subsequent to the second image and after a second Defined Event and/or a second physical and/or chemical change associated with a solid support (optionally the same or a different solid support).

The Defined Event can provide a physical and/or chemical change in a dynamic element that is, e.g., a thermally induced change (which may also be used for the assay), a pressure induced change, an optically induced change, a natural radioactive isotope decay, a chemically induced change, or combinations of any of the above. Time-domain encoding can exploit a defined stable, partially stable, selectively activatable, and/or unstable property (e.g., denaturation of an organic protein dye and/or an alteration in a chemical structure due to pH, heat or photosensitive labile bond, for example) of a respective encoding agent to force a change in the encoding signal, such as, e.g., the encoding signal for the solid support attached to the respective encoding agent or for the molecular recognition element attached to the respective encoding agent. For example, where the encoding signal is an intensity value, the physical and/or chemical change can result in an increase or decrease in the intensity value, e.g., by at least 0.01% between the first and second images and/or readings, more typically an increase or decrease by at least 1-20% between the first and second images and/or readings. The increase or decrease can be sufficient to move the intensity level from high to low, low to high, medium to low, low to medium, high to medium or medium to high, zero to low, high or medium or high, low or medium to zero, for example. The terms high, medium, and low refer to a first, second and third level, respectively, where the first is greater than the second and third, the second is between the first and third, the third is less than the first and second. In some embodiments, two or more different levels may be provided between the high and low levels (i.e., there may be more than one level between the high and low levels).

The encoding agent can comprise a caged dye which is photosensitive and is selectively activated upon sufficient photo (light) exposure to increase intensity.

The terms "similar spectral properties" or "spectrally similar" as used herein refer to encoding agents (e.g., dyes) and/or dynamic elements that have similar excitation and/or emission wavelengths and generate detectable fluorescence intensities in response to a light source operated at a single wavelength or a single wavelength range or band pass such that they would be indistinguishable in an image and/or reading.

The term "quenching" refers to deactivation of an excited molecular entity (e.g., an encoding agent) intermolecularly by an external environmental influence (such as a quencher) or intramolecularly by a substituent through a non-radiative process. A quencher is a molecular entity that deactivates (quenches) an excited state of an encoding agent, either by energy transfer, electron transfer, or by a chemical mechanism.

The fluorescence intensity of at least one encoding agent and/or dynamic element may decrease after a quenching event as the Defined Event. Alternatively, the fluorescence intensity of at least one encoding agent and/or dynamic element may increase after the Defined Event.

The term "bleaching" refers to the loss of absorption or emission intensity.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. The amplified sequence can also be detected by adding an intercalating dye to the reaction mixture and monitoring the fluorescence signal strength, which will be proportional to the total mass of double stranded DNA. Although embodiments according to the present invention are described with respect to PCR reactions, or nucleic acid and protein ELISAs, it should be understood that other nucleic acid amplification methods can be used, such as reverse transcription PCR (RT-PCR) including isothermal amplification techniques such as rolling circle amplification or loop-mediated isothermal amplification (LAMP).

DNA amplification techniques such as the foregoing can involve the use of a probe, a pair of probes, or two pairs of probes which specifically bind to DNA containing a polymorphism or mutation of interest, but do not bind to DNA that does not contain the polymorphism of interest under the same hybridization conditions, and which serve as the primer or primers for the amplification of the DNA or a portion thereof in the amplification reaction. Such probes are sometimes referred to as amplification probes or primers herein.

The term "reagent" refers to any substance or compound, including primers, the nucleic acid template and the amplification enzyme, that is added to a system in order to bring about a chemical reaction, or added to see if a reaction occurs. Amplification reagents or reagent refer to those reagents (deoxyribonucleotide triphosphates, buffer, etc.) generally used for amplification except for primers, nucleic acid template and the amplification enzyme. Typically, amplification reagents along with other reaction components are placed and contained in a reaction vessel (test tube, microwell, etc.).

The term "magnetic" as used herein includes ferromagnetic, paramagnetic and super paramagnetic properties.

In general, an oligonucleotide probe which is used to detect DNA containing a polymorphism or mutation of interest is an oligonucleotide probe which binds to DNA encoding that mutation or polymorphism, but does not bind to DNA that does not contain the mutation or polymorphism under the same hybridization conditions. The oligonucleotide probe is labeled with a suitable detectable group, such as those set forth below. Such probes are sometimes referred to as detection probes or primers herein.

Figure 1B:
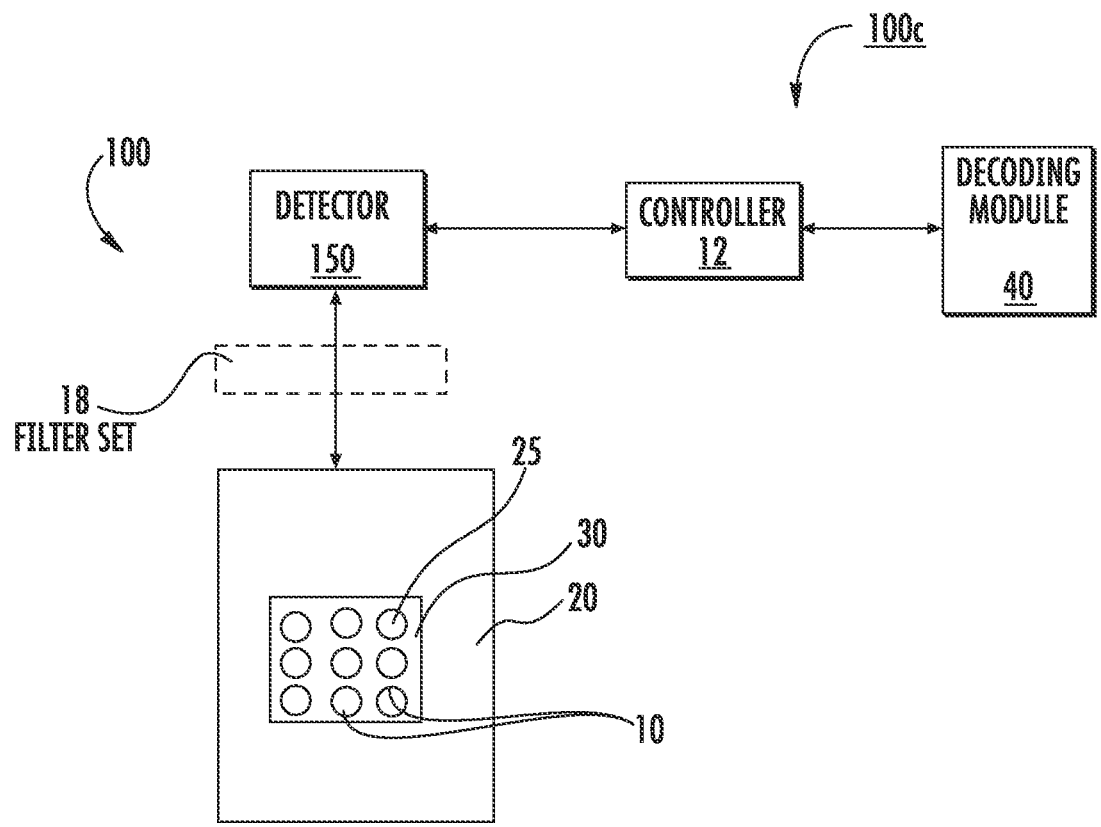
FIG. 1B is a schematic illustration of yet another analysis system according to embodiments of the present invention.

FIG. 1A is a schematic illustration of a fluidic analysis system 100 with a control circuit 100c comprising a controller 12, a detector 150 with at least one optical filter set 18 and a decoding module 40 configured to analyze encoding signals from solid supports 10 associated with an assay using a microfluidic device 20. FIG. 1B is an exemplary embodiment of another fluidic analysis system 100 with a control circuit 100c comprising a controller 12, a detector 150 with at least one optical filter set 18 and a decoding module 40, where the detector 150 can generate the Defined Event (e.g., optical excitation, photobleaching, etc.). This embodiment illustrates that no additional hardware components over conventional assay systems are required in contrast to other embodiments. The at least one optical filter set 18 can be configured to operate at a desired emission wavelength, such as, but not limited to, a single discrete range of wavelength and/or band pass, such as between about 10 nm to 1000 nm for excitation and imaging, and in particular embodiments for excitation about 545/30 nm and for imaging about 620/60 nm In some embodiments, the optical filter set 18 may be configured to operate at a wavelength in the ultraviolet (UV) range (e.g., at a wavelength in a range of 400 nm to 10 nm), infrared (IR) range (e.g., at a wavelength in a range of 700 nm to 1 mm), and/or visible light range (e.g., at a wavelength in a range of 390 nm to 700 nm) and/or any range and/or individual value therein. In some embodiments, the optical filter set 18 may not be fluorescence-based and may be optics, such as, e.g., polarization filters, to detect changes in light scattering. If the change is sized-based, then no filters may be needed, but rather the ability to image and measure size.

The microfluidic device 20 can have a bead well array 30 with an arrangement of bead wells 10 that hold respective beads 25. The controller 12 is also in communication with at least one device 125 (e.g., a thermal and/or light source) that can generate a Defined Event, which may change the environment of the beads 25 in the bead wells 10 for the dynamic decoding and/or may cause a physical and/or chemical change in the dynamic element.

The decoding module 40 can include or be in communication with a correlation table and/or database of different populations associated with different encoding agents of defined bead populations.

The device 125 can include a light source configured to emit light at a defined wavelength for a defined time to selectively activate, photoquench and/or photobleach beads 25 with one or more dynamic elements (e.g., encoding agents) responsive to same and/or a heat source configured to elevate the beads 25 to a critical temperature and/or a liquid source in fluid communication with the beads 25 in the bead wells 10 for altering the well environment and the like. The system 100 can be configured to evaluate recovery of the at least one detectable parameter after photobleaching. This recovery can be different for different materials/fluorophores in different environments and the differences can be exploited for decoding.

Figure 1C:
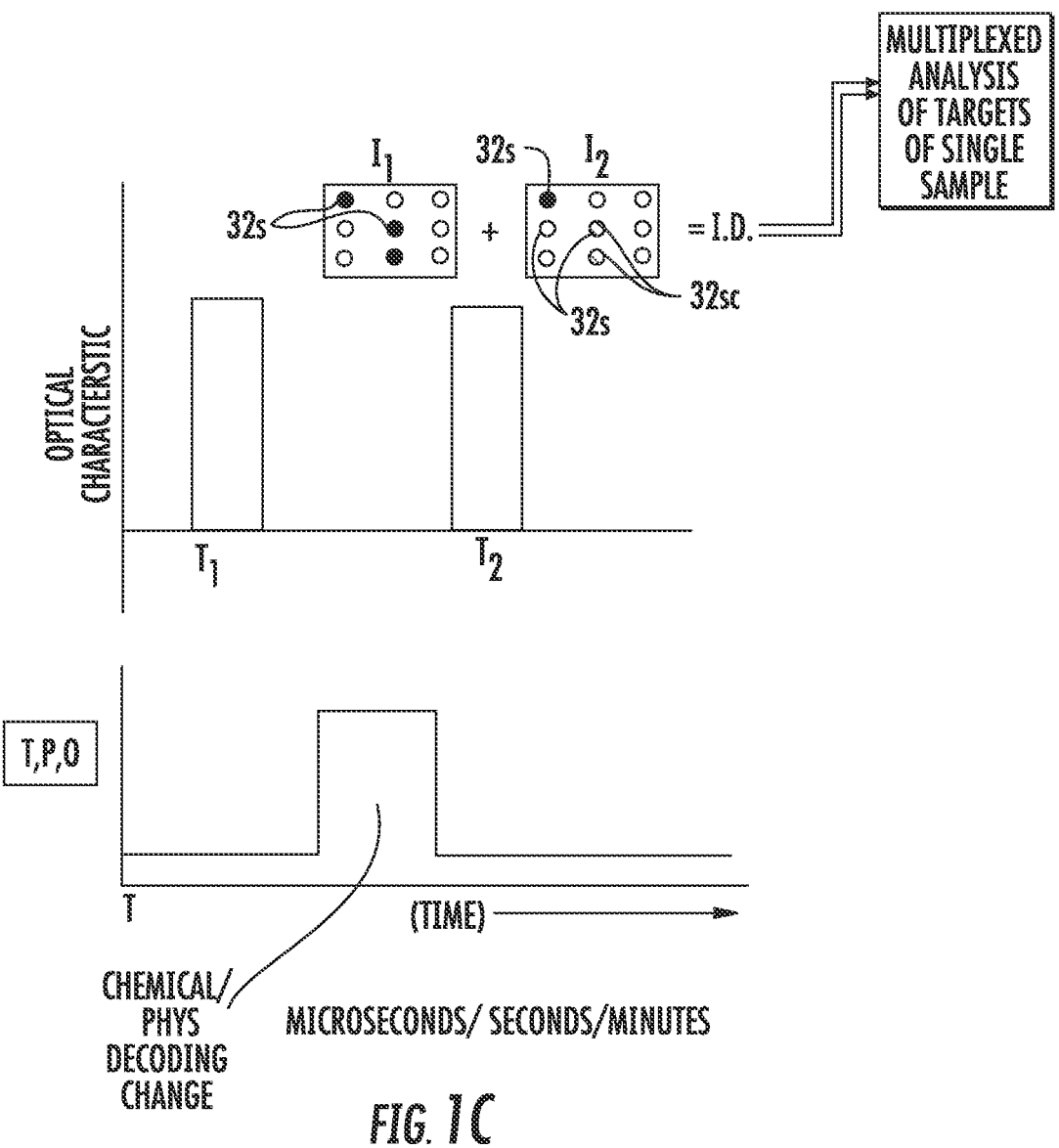
FIG. 1C is a schematic illustration of a timing diagram for obtaining images, shown as an image $I_1$ at a first time $T_1$ before a Defined Event ("DE") and an image $I_2$ at second time $T_2$ after a Defined Event (DE) according to embodiments of the present invention.
Figure 1D:
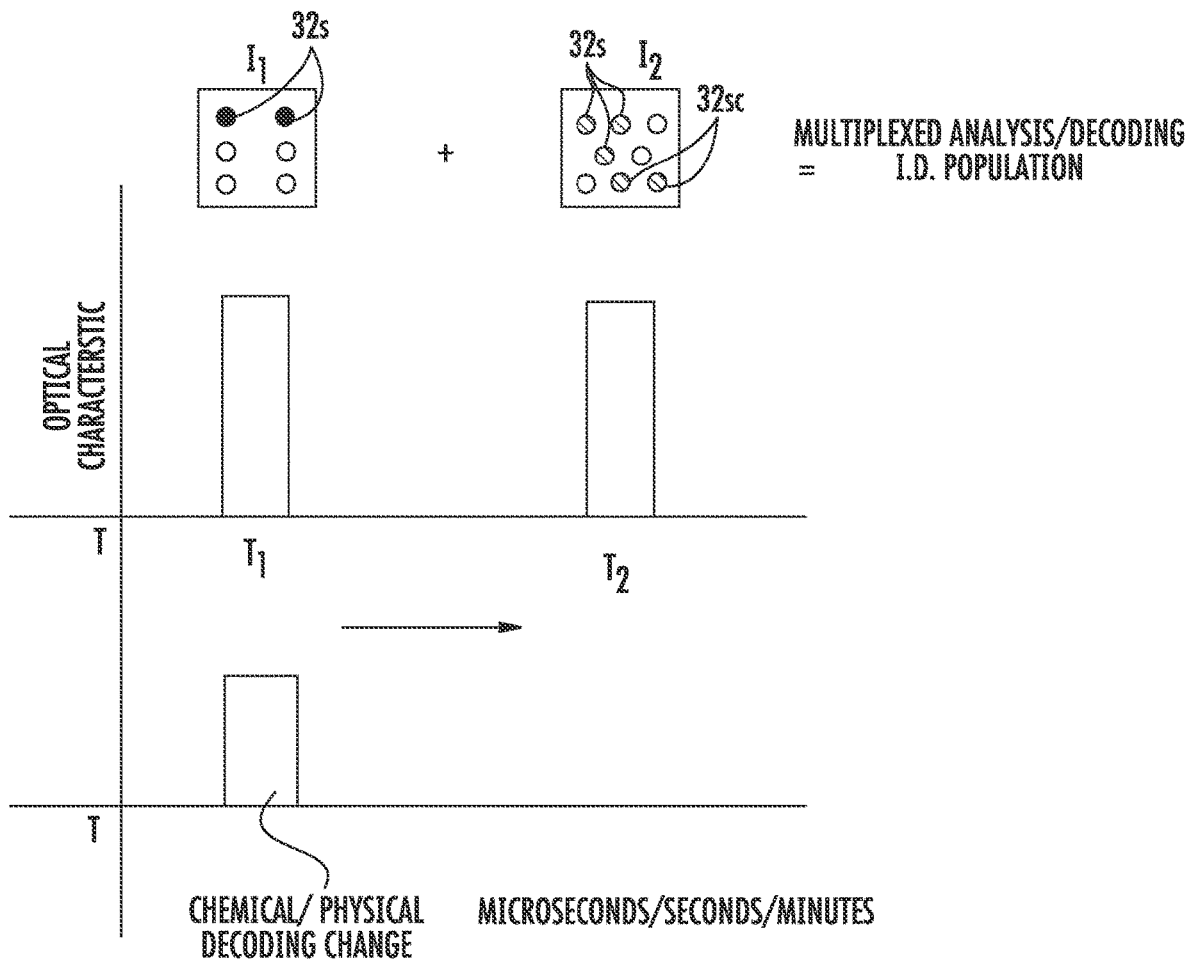
FIG. 1D is yet another schematic illustration of a timing diagram for obtaining images, shown as an image $I_1$ at a first time $T_1$ during a Defined Event ("DE") and an image 12 at second time $T_2$ after a Defined Event (DE) according to embodiments of the present invention.

As shown by FIG. 1C, the Defined Event (DE) may occur after a first image $I_1$ is obtained by the detector 150 and before a second image $I_2$ is obtained. Alternatively, as shown by FIG. 1D, the act of acquiring a first image $I_1$ can in and of itself be the Defined Event that results in a measureable change for the second image $I_2$ that is obtained after the first image $I_1$.

In some embodiments, the Defined Event DE can generate a defined environmental change to, in and/or about the bead well array 30 such as at least one actively forced or applied thermal change T (which can be an increase or decrease in temperature, although typically an increase and can, e.g., exploit a thermal instability of a dynamic element (e.g., an encoding agent) at a defined temperature), a chemical change C, (e.g., a change in pH which can be introduced in a number of manners), and/or an optical change O, such as introduction of light, optionally at a defined wavelength of light and/or intensity, e.g., for exposure sufficient to provide a quenching action to exploit a photo-instability. A second image $I_2$ can be obtained after the Defined Event DE. The system 100 can compare the intensity values 32s from the first and second images $I_1$, $I_2$ to identify solid support (e.g., bead) populations/sub-populations. As shown, the second image $I_2$ can include stable (substantially unchanged encoding signals $32s_s$) and changed intensity values $32s_c$ and this "fingerprint" or encoding signal(s) can be used for multiplexing the assay. The first image $I_1$, second image $I_2$ and/or further images obtained subsequently in response to another Defined Event DE can be used in a multiplexed analysis to identify targets of a respective single sample. Additional Defined Events can be the same type, e.g., if temperature, then a higher temperature than the temperature at the first defined event can be used. Additional Defined Events may be a different type of Defined Event than that of a first or prior Defined Event, e.g. a temperature change after photobleaching. Additional Defined Events may cause changes in the same properties as preceding Defined Events, e.g. a change in temperature that results in decreased fluorescence intensity for some populations can follow a photobleaching event that results in decreased fluorescence intensity for the same and/or different populations of the solid supports. Alternatively or in addition, additional Defined Events may cause changes in properties of the solid supports that are different from the preceding Defined Events, e.g. a change in temperature that results in some populations of solid supports changing in size by either swelling or dissolving can follow a photobleaching event that resulted in decreased fluorescence intensity for the same and/or different populations of the solid supports.

In some embodiments, photostability differences between quantum dots (QD) and fluorescent organic dyes and/or fluorescent proteins can be used for encoding the solid supports, e.g., beads, particularly if both have similar spectral properties. For example, photobleaching kinetics may be used to decode solid supports. Organic dyes can produce high fluorescence intensity but can be susceptible to photobleaching upon prolonged photoexposure. Quantum dots, however, do not typically photobleach but rather tend to maintain or increase fluorescent emission following additional photoexposure. See, e.g., Bouzigues et al., Biological Applications of Rare-Earth Based Nanoparticles. *ACS Nano* 2011, 5, 8488-8505; and Wang et al., Luminescent nanomaterials for biological labelling. *Nanotechnology* 2006, 17, R1-R13. The contents of these documents are hereby incorporated by reference as if recited in full herein.

As is known to those of skill in the art, a quantum dot is a nanoscale particle of semiconducting material that can be used for various experimental purposes, such as labeling proteins in conventional use. In some embodiments, QDs of a defined wavelength, e.g., about 605 nm, can be used as an encoding agent along with an organic dye (OD), and/or a fluorescent protein (FP). The organic dye (OD) can be a small molecule. A QD, organic dye and/or fluorescent protein can have different thermostabilites. QDs, ODs and/or FP can have similar fluorescence excitation/emission wavelengths. Non-limiting examples of excitation/emission wavelengths include 545/30 nm and 620/60 nm and can be imaged with a single filter set. Any quantum dot, fluorescent protein, and/or organic dye useful for luminescence (e.g., fluorescence) or other detectable parameter for time-domain encoding are contemplated by embodiments of the present invention. Examples of quantum dots that can be used in a method of the present invention include, but are not limited to, those including cadmium, indium, lead, sulfur, selenium, tellurium, zinc, and/or phosphorus, such as, e.g., CdS, CdSe, CdTe, InP, PbS, PbSe, and ZnS. Examples of organic dyes that can be used in a method of the present invention include, but are not limited to, fluorescein, Cy3 (Cy3.18), TAMRA, Texas Red (sulforhod-amine 101), Nile Red, Cy5 (Cy5.18), Atto740, Cy7, Alexa Fluor 750, IR125 (ICG). See, e.g., http://www.fluoprophores.tugraz.at/substance. Examples of fluorescent proteins (FP) include, but are not limited to, phycoerythrin, allophycocyanin, and green fluorescent protein (GFP).

Figure 2A:
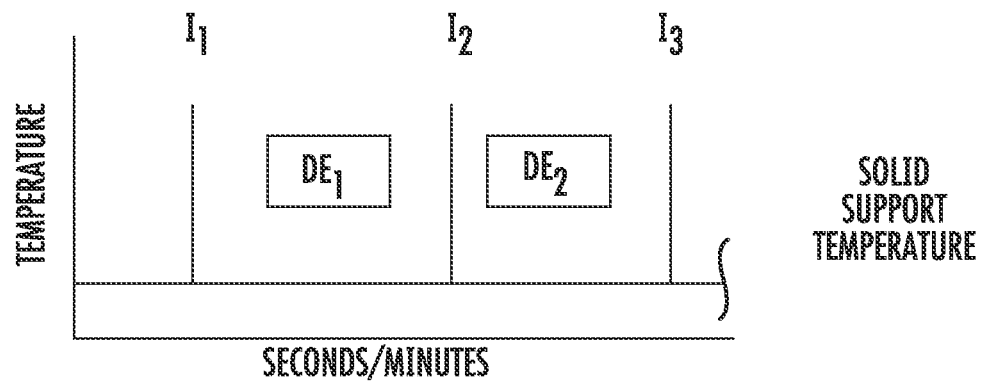
FIG. 2A is a graph of temperature for a solid support over time that illustrates the points in time at which a first, second and third image, $I_1$, $I_2$, and $I_3$, can be obtained with respect to at least one Defined Event (DE) involving photobleaching for a suitable time according to embodiments of the present invention.

Beads or other solid supports can be encoded with an organic dye, a fluorescent protein (or protein dye), a QD, or a mixture of two or more of the same or different types (Mix) to produce comparable initial fluorescence signals. Beads or other solid supports can then be utilized in an assay, such as, e.g., the beads may be loaded into microfluidic microwell array devices, sealed with oil to isolate individual bead wells from their neighbors, and successively imaged before, after, and/or during a Defined Event. For example, referring to FIG. 2A, the temperature of a solid support, e.g., beads, may be held at a defined temperature, and a first image $I_1$ may be taken prior to a Defined Event, $DE_1$, (e.g., prior to a 1 microsecond-50 hour photobleach, typically between about a 1 second to about a 3 minute photobleach) and second and third images $I_2$ and $I_3$ may be taken after the Defined Event, such as, e.g., after $DE_1$ and/or $DE_2$. Photobleaching can be based on luminous energy, which can be delivered over any relevant or practical timescale, depending on the assay.

Figure 2B:
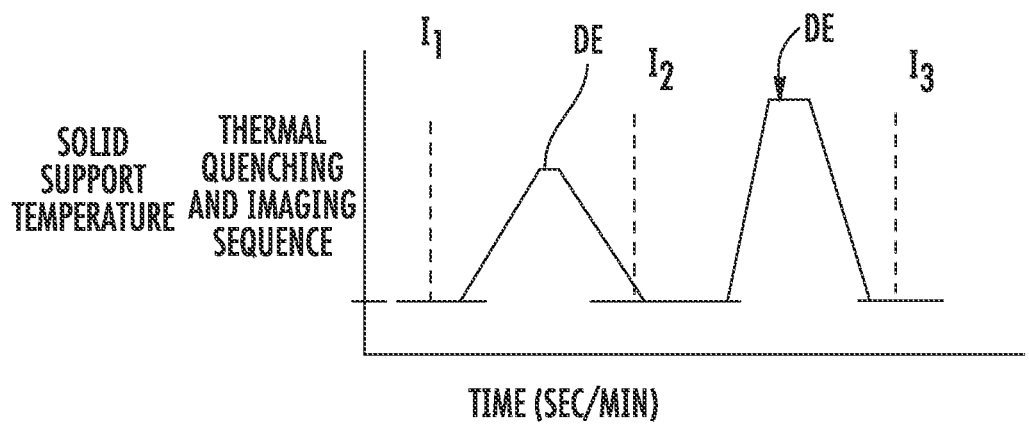
FIG. 2B is a graph of temperature for a solid support over time that illustrates the points in time at which a first, second and third image, $I_1$, $I_2$, and $I_3$, can be taken with respect to a Defined Event (DE) involving thermal quenching according to embodiments of the present invention.

FIG. 2B illustrates another embodiment for an exemplary thermal quenching and imaging sequence in which the temperature of a solid support, e.g., beads, is increased at least once to a defined threshold (critical temperature) value for a Defined Event, and a first image $I_1$ may be taken prior to the Defined Event (e.g., the first increase in temperature) and a second image $I_2$ may be taken once the temperature is returned to a set value (to have the same relative operating parameters for the detector). The term "critical temperature" refers to a temperature at which the physical and/or chemical change occurs for a dynamic element (e.g., an encoding agent). FIG. 2B also illustrates a second Defined Event at a higher threshold temperature after which a third image $I_3$ can be obtained. In some embodiments, the Defined Event may include photoexposure (e.g., photobleaching) of the encoded solid support for a given period of time, such as, e.g., 1 microsecond or more, typically between about 1 second and 10 minutes such as, 5 seconds or more, such as, for example, 1, 5, 10, 15, 20, 25, 30, 35, 40, 45 seconds or 1, 2, 3, 4, 5, or more minutes.

In some embodiments, obtaining a first image, readout, and/or detecting of an optical or electrical signal of a solid support (e.g., a plurality of solid supports), which can include a first image $I_1$, may be taken before an assay and the assay itself can generate the Defined Event (e.g., thermal and/or light exposure during the assay). In some embodiments, the first image, readout, and/or detecting of an optical or electrical signal of a solid support can be taken after an assay is completed, but prior to a Defined Event, and the image, readout, and/or detecting may be used to determine initial fluorescence intensity and/or to serve as a reference for data normalization. Comparison of images, readouts, and/or signals before (including a reference image) and after a Defined Event can illustrate if a chemical and/or physical change associated with a solid support occurred following the Defined Event (FIGS. 3A-C).

Figure 3A:
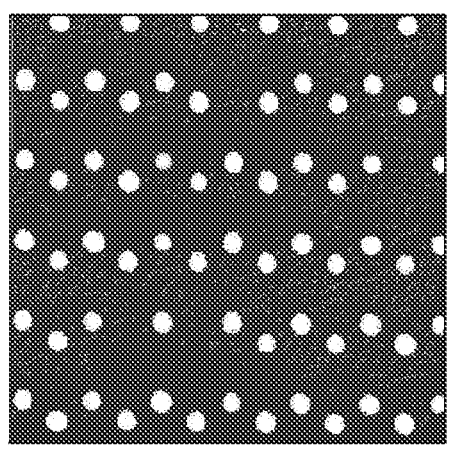
FIGS. 3A-C show three images (i.e., FIGS. 3A, 3B, and 3C) of different encoded bead populations that were loaded into a single fluidic device and electronically/optically distinguished in obtained images by changes in fluorescence caused by photobleaching as the Defined Event.
Figure 3B:
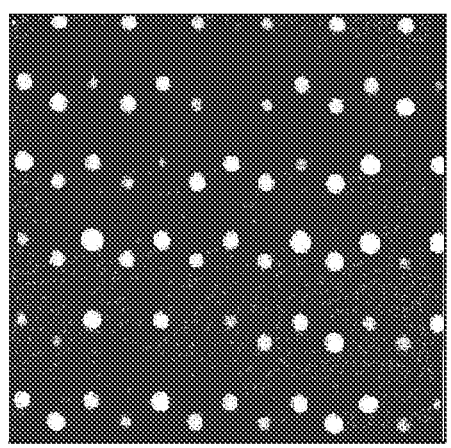
Figure 3C:
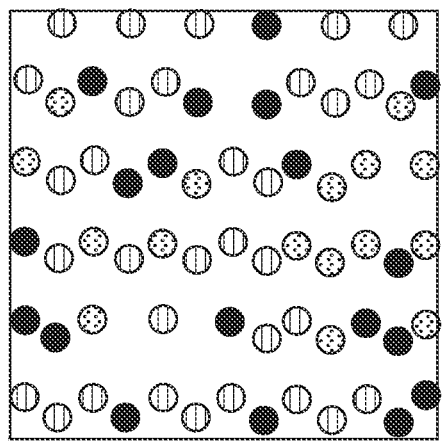
Figure 4:
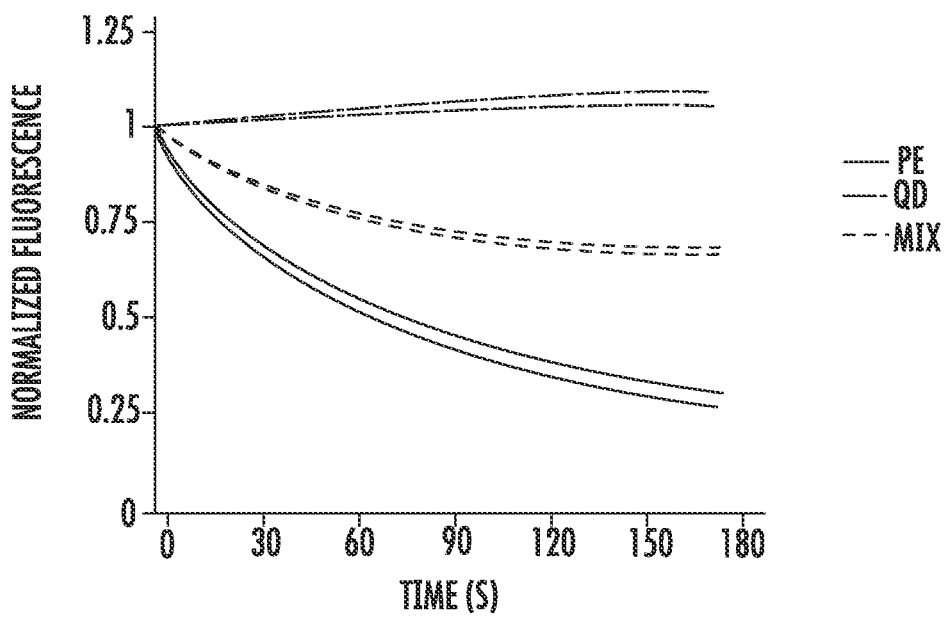
FIG. 4 is a graph of photobleaching profiles (normalized fluorescence versus time/seconds) for populations of beads encoded with PE, QDs, or a mixture of both PE and QD dyes. Five replicate microchips loaded with each bead population are depicted.

As shown in FIG. 3A, prior to photoexposure, in the image, beads encoded with FP, QDs, or a mixture of both produced comparable initial fluorescence signals that were indistinguishable as they have similar spectral properties. In contrast, as shown in FIG. 3B, after photoexposure, beads encoded with FP experienced significant bleaching over the course of 3 min while QD-encoded beads were unaffected by prolonged illumination as evidenced by their stable fluorescence over the same duration. FIG. 3B also shows that beads labeled with a mixture of both dyes exhibited moderate bleaching, less extensive than the FP-encoded population. Thus, different mixtures of both dyes can provide beads that exhibit different levels of bleaching to provide a number of different fluorescence encoding states, which can be used to identify each bead population (FIG. 3C). Plotting the fluorescence decay profiles shows that each bead set was well-resolved from the others (FIG. 4). The precision of this dynamic decoding approach was also demonstrated to be high given the similar bleaching rates observed within each bead population (n=5 replicate microchips each, >50 k beads total).

"Indistinguishable" as used herein with reference to an encoding agent, dynamic element, and/or signal (e.g., a fluorescence signal) refers to a signal and/or parameter (e.g., a color, size, and/or intensity value (e.g., a fluorescence intensity value) at a given wavelength) that is within the standard deviation, confidence interval, and/or standard error of a population of supports for a given measurement system. Thus, when two encoding agents and/or dynamic elements are indistinguishable (e.g., the fluorescence signals for two encoding agents and/or dynamic elements are indistinguishable), the signal or parameter (e.g., the intensity values for the fluorescence signals) for the two encoding agents and/or dynamic elements cannot be used to identify and/or separate which encoding agent and/or dynamic element a signal or parameter corresponds to. Accordingly, it cannot be determined which signal (e.g., fluorescence signal) is from one of the two encoding agents and/or dynamic elements. There may be a distribution range within which an encoding signal for an encoded element (e.g., an encoded bead or an encoded molecular recognition element) in a particular population may fall within. As long as a distribution range for another encoded element does not overlap or fall within the distribution range of another population, then the encoding state can be determined for the two populations such that they can be distinguished. In some embodiments, each encoding state may be defined by a range of values due to variations in the measurements of encoded elements in a single population. This range may not be the standard deviation of the measurement of a single encoded element.

In some embodiments, in a sample comprising a plurality of solid supports, a portion of the solid supports may have indistinguishable initial intensities and another portion of the solid supports may have distinguishable initial intensities. In some embodiments, even though two solid supports may have distinguishable intensities, the solid supports may encode the same solid support population if the intensity values fall within the distribution range for that solid support population. Some embodiments include two or more different populations where the subpopulations have discrete and distinguishably different intensity levels, but these subpopulations may contain additional subpopulations that are only distinguishable after a Defined Event.

Figure 5:
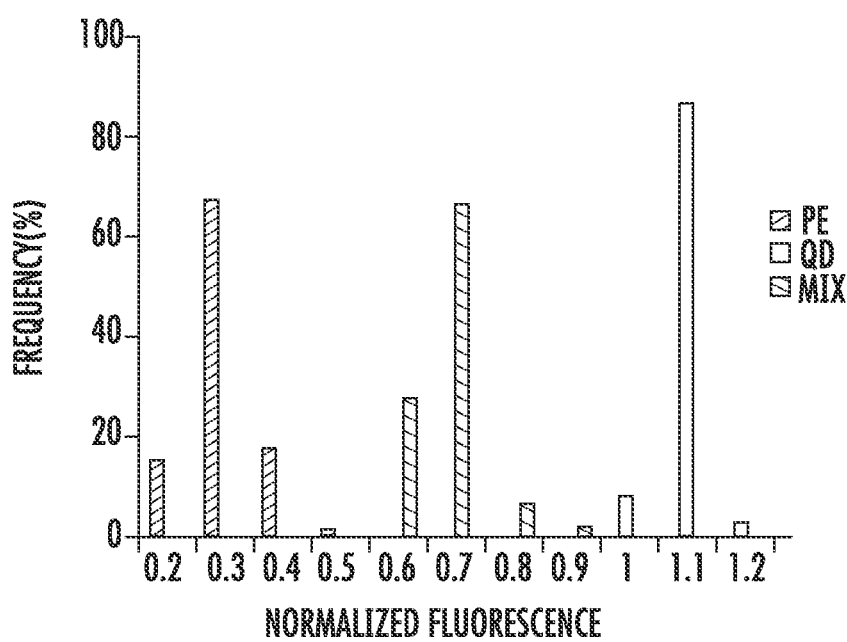
FIG. 5 is a graph of frequency (%) versus endpoint normalized fluorescence intensities for each bead population sorted into histograms after photobleaching. Each bead set (PE, QD and Mix) was well resolved from the neighboring population(s) which can allow for high identification accuracy.

Endpoint fluorescence decay values can be measured for each individual bead population. For example, the endpoint fluorescence decay values were measured for the beads encoded with FP, OD, QDs, or a mixture of agents, and these values were then normalized to the initial bead intensity and sorted into histograms. FIG. 5 illustrates the distribution of intensities by bead type. The three different populations measured in this example were very well resolved from one another producing identification accuracies of >99.98%. This high resolution will allow beads combined together in a single sample to be readily identified without ambiguity once loaded into an array and dynamically decoded.

In some embodiments, a solid support and/or molecular recognition element may include one, two or more encoding agents in order to provide two or more, typically between about 2 to about 10,000 (or greater) different encoding signals representing different populations (e.g., about 2, 3, 4, 5, 6, 7, 8, 9, 10, 20, 50, 100, 200, 500, 1,000, 2,000, 3,000, 4,000, 5,000, 6,000, 7,000, 8,000, 9,000, 10,000, or more) that may be distinguished and/or identified using one or more Defined Events. Some embodiments include different populations (e.g., different solid support populations and/or different molecular recognition element populations) at or able to generate different fluorescence levels relative to each other using one or more Defined Events. For example, a solid support may include a first encoding agent that corresponds to a first population and a second encoding agent that corresponds to a second population, the first and second encoding agents may be the same or different and each may have an initial fluorescence intensity level. In some embodiments, the initial fluorescence intensity level for the first and second encoding agents is the same or substantially the same. In other embodiments, the initial fluorescence intensity level for the first encoding agent is different than the initial fluorescence intensity level for the second encoding agent. Not all solid substrates are required to have an encoding agent or some populations may have a single dye. The dye may be stable and may not generate and/or exhibit a physical and/or chemical change for some solid substrate populations.

Each of the first and second populations may include one or more sub-populations, such as described above, where each sub-population may have the same or substantially the same initial fluorescence intensity level. Recognizing that different systems will operate with different resolution and capability, in some particular embodiments, the term the "same or substantially the same" with respect to a fluorescence intensity level can, in some embodiments, refer to a variation of ±0.15 or less (e.g., ±0.1 or 0.05) for a normalized fluorescence intensity value and/or a value such that it remains within a defined range of a defined level, e.g., high, medium, low. For example, and without limitation, a bead with an encoding agent may have a normalized fluorescence intensity value of 0.7 and beads having the same or substantially the same fluorescence intensity level may have a normalized fluorescence intensity value in a range of 0.55 to 0.85.

Using beads encoded with FP or QDs, or a mixture, as described above, initial fluorescence intensity levels that were substantially similar (unable to be reliably or accurately distinguished) to each other but different than the initial fluorescence intensity level shown in FIG. 3A (less bright/intense) were generated. These beads were shown to photobleach similarly to the brighter beads producing three more bleaching-distinguishable subpopulations or encoding states similar to those depicted in FIGS. 3A-C. This ultimately provided additional multiplexing capability with single wavelength identifying three distinguishable changes in intensity (FP, QD, and Mix).

Accordingly, incorporation of the time domain into decoding and/or a multiplexing assay (e.g., a multiplexing bead-based bioassay) can greatly increase the number of distinct multiplexing encoding states. While only two encoding levels could have been achieved with conventional methods, the dynamic decoding methods produced at least six resolvable populations or encoding states. These benefits can significantly enhance the multiplexing capability of bead-based POC assays while also minimizing cost and complexity of the required analytical equipment.

In some embodiments, additional solid support (e.g., bead) populations at a single initial fluorescence intensity level may be provided. In some embodiments, more bead populations at a single initial fluorescence intensity level may be provided by pre-sorting encoded beads. In some embodiments, the approach may be expanded to other wavelengths without using a single, common detection wavelength for the analysis (e.g., 1, 2, 3, 4, 5, 6, 7, 8, 9, 10, or more different wavelengths or spectral bands or ranges) to increase the amount of multiplexing levels that could be achieved.

Incorporation of the time domain into solid support decoding strategies can be performed using strategies beyond differences in photostability of the different encoding dyes. In some embodiments, an alternative or additional dynamic encoding strategy is to exploit the thermal stabilities of an encoding agent. For example, a protein and/or organic dye can be susceptible to heat denaturation at elevated temperatures. QDs, however, are semiconductor materials that are stable at elevated temperatures. These properties for these dyes can be utilized in dynamic decoding embodiments.

Figure 6:
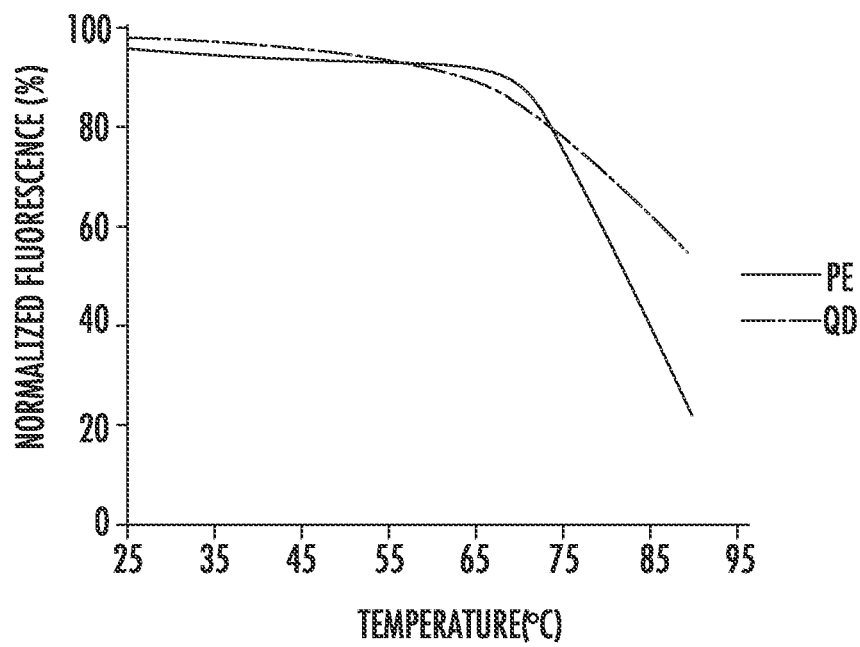
FIG. 6 is a graph of normalized fluorescence (%) versus temperature (degrees C.) for encoded beads sealed within a microwell array of a fluidic device that was heated to the indicated temperature for a thermal Defined Event. Elevated temperatures preferentially quenched fluorescence from phycoerythrin (PE) above 80° C.

Microspheres were labeled with FPs or QDs so that each population exhibited indistinguishable initial fluorescence. Each bead population was then loaded into microchips for imaging as previously described. Images were first acquired at 25° C. to determine the initial fluorescence intensity and also to serve as a reference for data normalization. Chips were then heated to elevated temperatures to denature the FP, then cooled back to 25° C. and imaged again. The loss of fluorescence intensity between the pre- and post-heating images allowed for the identity of the bead populations to be determined. FIG. 6 illustrates the decrease in normalized fluorescence signal upon heating the beads. A decrease in signal is observed as temperature is increased due to disruption of streptavidin-biotin bonds at temperatures ≥70° C. Both FP and QDs were conjugated to the beads via streptavidin-biotin chemistry. However at higher temperatures, FP begins to denature and its fluorescence drops significantly. This differential quenching can be used to identify differently encoded beads with good resolution (FIG. 7).

Figure 7:
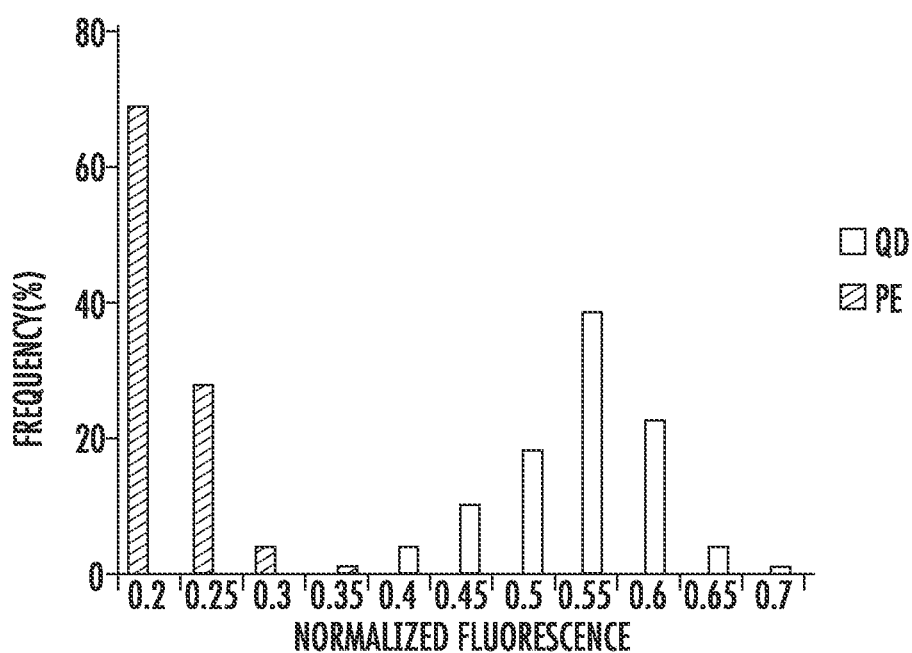
FIG. 7 is a graph showing frequency (%) versus normalized fluorescence intensities for each bead population after being heated. Thermal decoding allowed for different bead populations with similar initial fluorescence to be distinguished from one another.

As illustrated by FIGS. 6 and 7, incorporation of a dynamic element (i.e., the fluorescent protein (FP), which is denatured as the temperature changes over time) allows for previously unattainable encoding levels of multiplexing to be gained without complicating the imaging system. In some embodiments, incorporation of a temperature change in the time domain may be used for PCR-based assays where heating elements are already in place for thermocycling, thereby requiring no additional components for thermally-resolved multiplexing. In some embodiments, the concentration of a dye on a solid support (e.g., a bead) and/or a buffer composition may be modified to accentuate and/or increase resolution between solid support populations and/or allow additional distinguishable populations to be produced and identified.

According to some embodiments, a time domain measurement may be used to decode an encoded solid support (e.g., a bead set) where one or more compounds (e.g., dynamic elements such as encoding agents) have been added to a portion of the solid support (e.g., a subset of beads). The one or more compounds may be dynamic elements that provide a physical and/or chemical change in response to a Defined Event. In some embodiments, the physical and/or chemical change may be an observable change. For example, in some embodiments, the one or more compounds may provide for a change in fluorescence signal that is observed over the course of a temperature change caused by a change of quantum efficiency of one or more of the compounds (e.g., encoding dyes). In some embodiments, the addition of a heat-labile or photoactivated compound (e.g. a photoactivated acid like triarylsulfonium/hexafluoroantimonate salt) to one or more portions of a solid support, upon activation, may result in a change in chemical properties of the solid support (e.g. pH) that affects a change in fluorescence properties of an encoding agent (e.g. fluorescein). Alternatively, solid supports contained in reaction wells that either have or constitute sensors or electrodes or electrode arrays that are sensitive to pH or conductivity changes (e.g. the Ion Torrent platform, https://www.thermofisher.com/us/en/home/brands/ion-torrent.html) can measure these changes directly.

In some embodiments, a portion of a plurality of solid supports may include labile attachment chemistries for one or more dynamic elements that, upon activation (e.g., temperature change, pH change, solvent addition/removal, etc.) provide a physical and/or chemical change that results when one or more of the encoding compounds is lost to the surrounding solution (e.g. FITC-biotin released from a streptavidin-coated bead upon heating, and detected in the fluid contained within the assay well). In some embodiments, a mix of labile and non-labile (e.g. heat-labile or photocleavable streptavidin-biotin bonds and stable covalent chemical bonds, respectively) encoding agents may be used.

Figure 20:
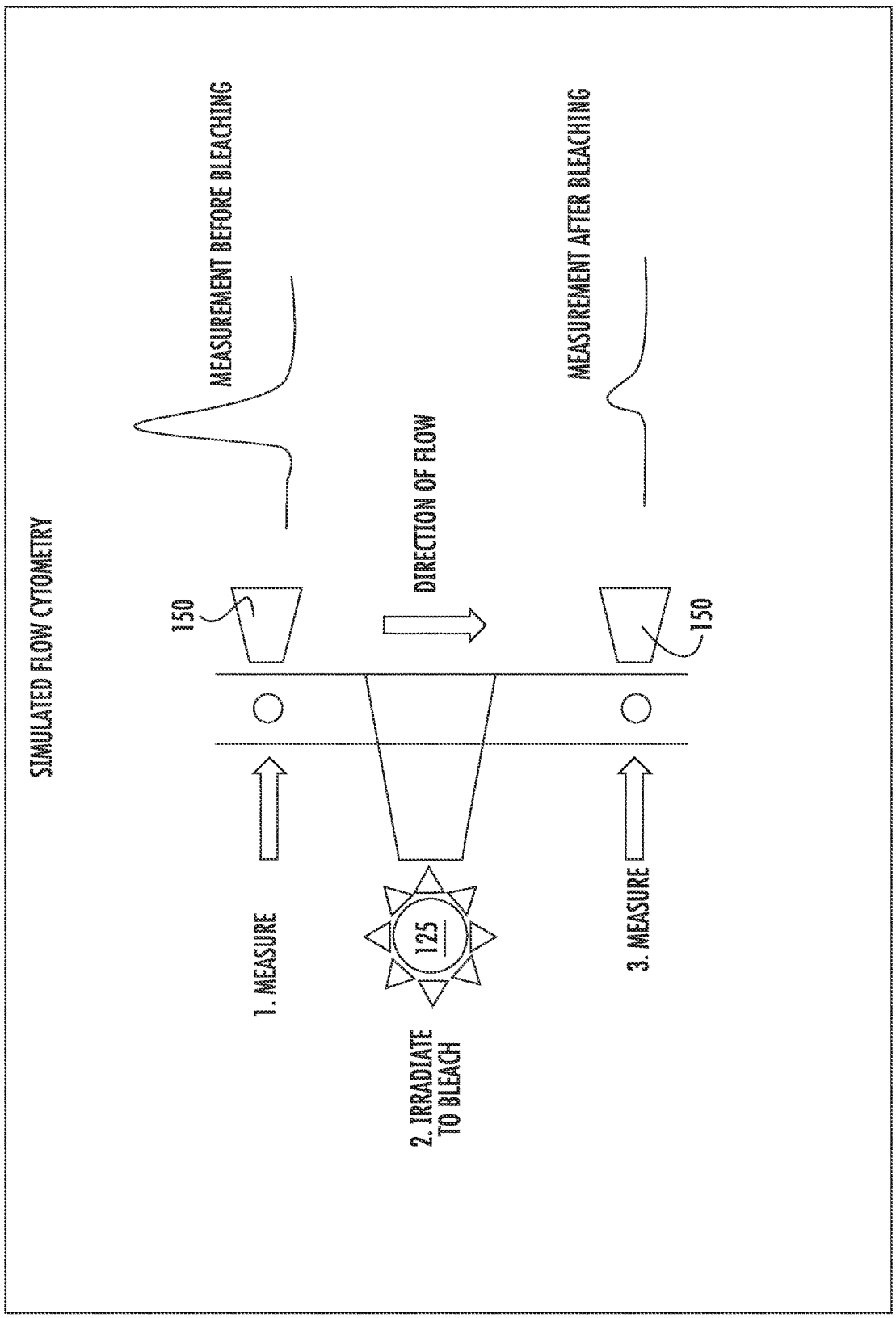
FIG. 20 is a schematic illustration of an example flow cytometry system according to embodiments of the present invention.
Figure 21:
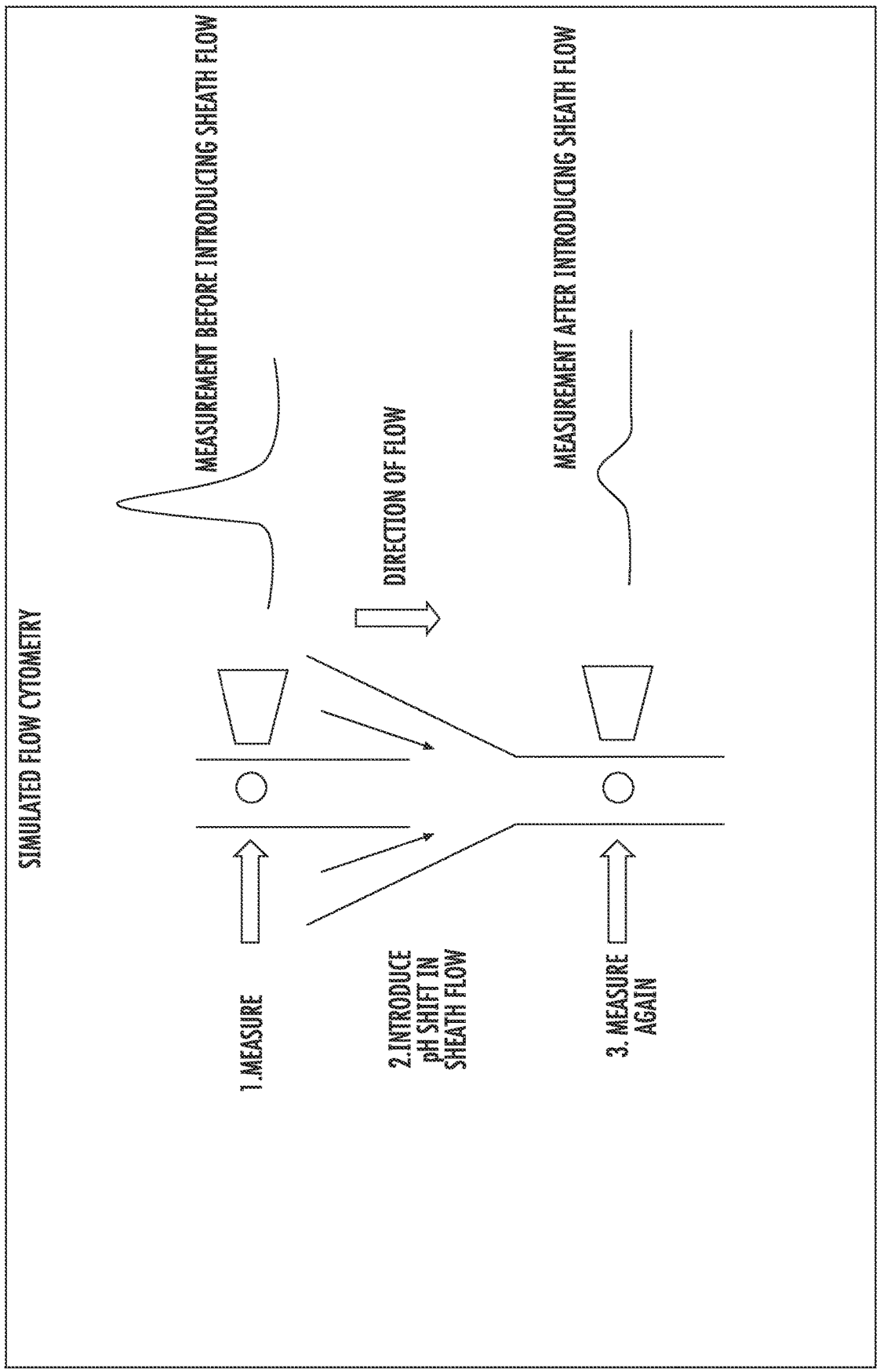
FIG. 21 is yet another schematic illustration of an example flow cytometry system according to embodiments of the present invention.

Some embodiments include the use of encoding agents (e.g., dyes) as dynamic elements that have varying degrees of susceptibility to quenching agents (oxygen, dabsyl, Black Hole Quenchers, Iowa Black, etc.) so that upon addition or removal of such quenching agents, a different population (e.g., a bead population) can be identified. In some embodiments, the dynamic element may include a quencher and one or more compounds may be protected from the quencher (e.g., by encapsulation, binding to a protein, etc.) and this may be used to accentuate differences between dyes and allow for different populations to be identified. In some embodiments, this can be affected in flow cytometry formats by the addition of a quencher into the sheath flow liquid after an initial read upstream in the system. An example flow cytometry system is shown in FIG. 20 in which measurements before and after photobleaching are depicted. A further example flow cytometry system is shown in FIG. 21 in which measurements before and after a pH shift are depicted. Alternatively, a pH, organic solvent strength, ionic strength, or other such property can change by the addition of the sheath flow to affect a detectable change in the solid supports' encoding properties In some embodiments, methods for dynamic decoding solid support populations can employ the time domain in a chemical and/or biochemical assay. Example assays include, but are not limited to, immunoassays, nucleic acid hybridization arrays, PCR, RT-PCR, RT-qPCR, etc.

Methods of the present invention may be used with solid supports, such as, e.g., beads and substrates that are not beads, such as printed arrays on a solid surface. In some embodiments, a method of the present invention may include photoresist or "printed" barcode reagents where strips or sections of each particle may vary and thereby create a distinct population. Compounds that may be used in a method of the present invention include, but are not limited to, fluorophores, chromophores, photocleavable or photoactivated compounds, heat activated or heat cleavable compounds or functional groups, and/or compounds that incorporate radioactive isotopes or magnetic or electrically conductive elements. Solid supports may also be engineered to change conformation, shape, and/or other physical properties in response to a Defined Event by methods such as, but not limited to, the use of different polymers with different physical and thermal properties or varying the degree of crosslinking between polymer strands for certain populations.

In some embodiments, a method of the present invention is used to detect two or more different populations of nucleic acids after PCR. PCR has many applications, for example the detection of trace amounts of nucleic acids to determine the presence of disease causing organisms, gene expression, genotyping, genetic engineering or modification, and forensic science applications. PCR amplification provides outstanding target identification and quantification over a large range of analyte concentrations. However, simultaneous and quantitative analysis of many analytes by PCR has proven to be extremely challenging. Intercalating dye fluorescence-based detection is only capable of determining total dsDNA concentration and therefore concurrent analysis of multiple templates in a single reaction vessel is not possible using this detection method. Fluorescent probe technologies (e.g., Taqman, molecular beacons, or other chemistries) can be used for low-level multiplexing of reactions as each target can be amplified using a different color fluorescence probe as a signaling reporter. Probes are also sequence specific, reducing false positives from primer-dimer formation or nonspecific amplification. A typical method for multiplexing with either conventional microtiter plate or microfluidic real-time-PCR (rt-PCR) is to use a small number of reaction wells, each containing three different color probes. However, it is generally considered challenging to design multiplexed primer and probe sets as they require an additional level of careful design and optimization to insure compatibility with each other. Multiplexing by this method is ultimately limited, by instrumentation and spectral overlap between dyes, to four-color detection, with one color typically reserved for an internal standard dye. However, the present invention may provide a method of increasing the multiplexing of the assay.

Figure 8:
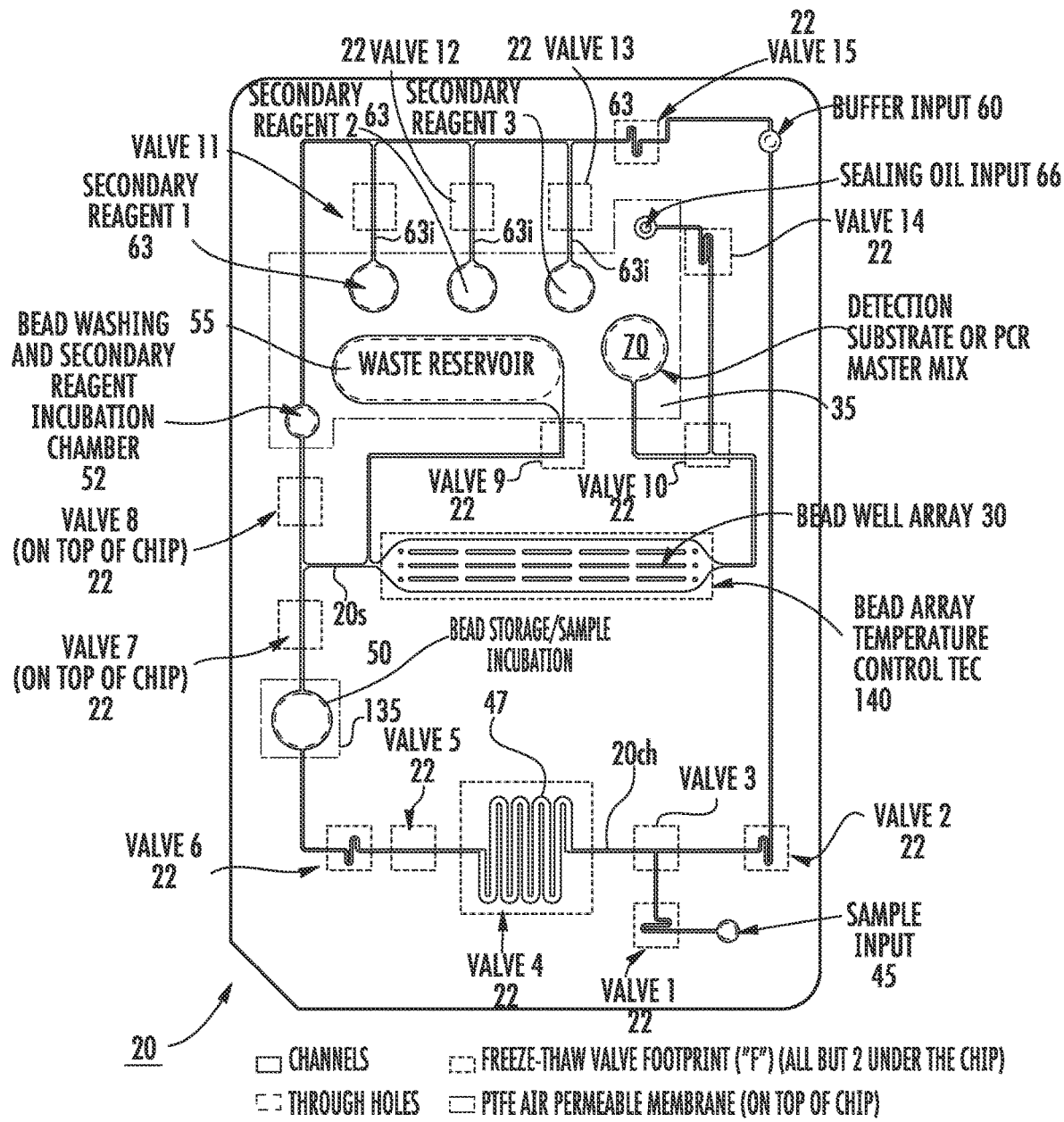
FIG. 8 is a top view of a microfluidic device with an exemplary bead well array according to embodiments of the present invention.

FIG. 8 shows a microfluidic device 20 with a bead well array 30 according to embodiments of the present invention. The device 20 can include freeze-thaw valves 22 with microfluidic channels 20ch in fluid communication with the bead well array 30.

Referring to FIGS. 9A, 9B, 10A, 10B, 11A, 11B, 12A and 12B, examples of bead wells 10 with geometries for improved signal detection are shown. As shown in FIGS. 9A and 9B, the solid substrates 25 can cooperate with conventional bead wells 10 having circular perimeters (typically cylindrical or conical wells) that are configured to hold a bead. In other embodiments, as shown in FIGS. 10A, 10B, 11A, 11B, 12A and 12B, for example, bead wells 10 according to embodiments of the present invention have geometries with a bead retention segment 11 in fluid communication with a signal detection segment 15 that is adjacent the bead retention segment 11.

The bead wells 10 can be provided in a relatively dense array 30 of closely spaced apart bead wells 10. The bead wells 10 can be aligned in rows and columns or be offset from each other. The bead wells 10 can be provided in a regularly repeating pattern, an irregular repeating pattern, or in other patterns. The term "dense" means that a footprint of a fluidic analysis device can have between about 100-6000 wells 10 per mm$^2$ and/or between 10,000 to 5,000,000 wells 10 per cm$^2$, typically between about 6,000 to about 2,000,000 wells 10 per cm$^2$, more typically between about 500,000 to about 2,000,000 wells 10 per cm$^2$.

Some or all of the neighboring wells 10 can have a separation distance of between 0.11-1,000 µm such as about 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 100 µm, 200 µm, 300 µm, 400 µm, 500 µm, 600 µm, 700 µm, 800 µm, 900 µm, 1000 µm or any fractional number therebetween, measured centerline to centerline of the neighboring bead retention segments 11.

Some or all of the wells 10 can all be reaction wells 10 that cooperate with amplification reagents. Some or all of the wells 10 can process sub-pL reaction volumes.

The signal detection segment 15 can optionally comprise a short and/or elongate fluidic channel 15ch that connects an end of the signal detection segment 15e with the bead retention segment 11. The signal detection segment 15 can include an end 15e that is spaced apart a distance "L" from the bead retention segment 11, typically by between 30% to about 10,000% (0.3× to about 100×) of a diameter of a target bead, more typically between about 0.3× to about 10× of the diameter of a target bead. In some embodiments, L can be between 1× and 5× the diameter of a target bead. For example, for 3.2 µm diameter beads, the length L can be between about 1 to about 320 µm, more typically between 1 and 32 µm, and in particular embodiments can be between about 3.2 and 16 µm. To be clear, a number with the letter "x" refers to a multiplier, one times (1×), ten times (10×) and the like.

In some embodiments, L can be between about 1 µm to about 100 µm, more typically between 1 and 20 µm, such as about 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, and about 20 µm. The length L can be measured from a centerline of the bead retention segment 11 or from a line completing the diameter of the bead retention segment drawn over the channel 15c connecting the bead retention segment 11 with the end of the signal detection segment 15e.

FIGS. 10A and 10B illustrate that the signal detection segment 15 can optionally be configured as a narrow channel or "slit", typically having a width that is 25%-75% less than a width of the bead retention segment 11.

FIGS. 11A and 11B illustrates that the signal detection segment 15 can have an end portion that is arcuate 15a, with a radius of curvature less than that of the bead retention segment 11. The distance "d" between centerlines of the bead retention segment and the arcuate end 15e can be the same as the length "L" discussed above.

FIGS. 12A and 12B illustrate that the signal detection segment 15 can have an end that has an annular channel 17 surrounding an internal upwardly projecting member 19.

The projecting member 19 can have a height sufficient to extend above the fluid in the annular channel 17 of the signal detection segment 15. This configuration can define a detectable signal comprising a portion with an annular shape.

The new geometries of the bead wells 10 are believed to improve detection in microbead array-based technologies. These well geometries can be configured such that one area of the well 11 is for magnetic loading and bead retention, and another region of the well 15 can be used (primarily or only) for detection of a signal. In some embodiments, after loading the beads 25 (shown by way of example with a solid circle in one of the wells in each of FIGS. 10A, 11A and 12A) in the bead regions 11 of the wells 10, a small volume of reagent fluid can be isolated in the wells 10 using a method such as immiscible fluid sealing or pushing against another surface such as a gasket or other substrate as is known to those of skill in the art.

While some exemplary embodiments are shown in FIGS. 10A, 10B, 11A, 11B, 12A and 12B, other embodiments may include other geometries, typically configured so that the bead retention region 11 has a pocket or receptacle with an opening diameter that is between about 101-195% of the diameter of the bead 25, and may be between about 105% and 150% in some embodiments. The depth of the well in the bead retention region 11 can be between about 50% and 185% that of the bead diameter.

The depth of the well 10 at some or all of the signal detection region 15 may be the same, deeper or more shallow than the well at the bead retention segment 11. The depth may decrease as the channel 15*ch* travels away from the bead retention segment 11. The depth may increase as the channel 15*ch* travels away from the bead retention segment 11 toward the end of the signal detection segment 15. The walls of the well 10 may taper outwardly or inwardly in a direction into the well 10.

Different wells 10 may have different volumetric capacities, geometrical shapes patterns and/or sizes.

In some embodiments, the signal detection segment or region 15 can have a channel 15*ch* such as a pocket or slit or other geometric shape into which a target bead cannot physically enter. Both regions 11, 15 are fluidically connected so that reagents and/or analytes released from the bead 25 can diffuse or otherwise mix throughout the common solution volume of the well 10. By spatially separating the bead 25 from the detection region 11, the contribution of bead fluorescence to the signal can be reduced or eliminated, improving signal to noise ratio.

The geometries of the wells 10 can allow high, single occupancy loading of reaction wells 10 while increasing a respective reaction volume, potentially improving reaction efficiency.

Figures 13A, 13B:
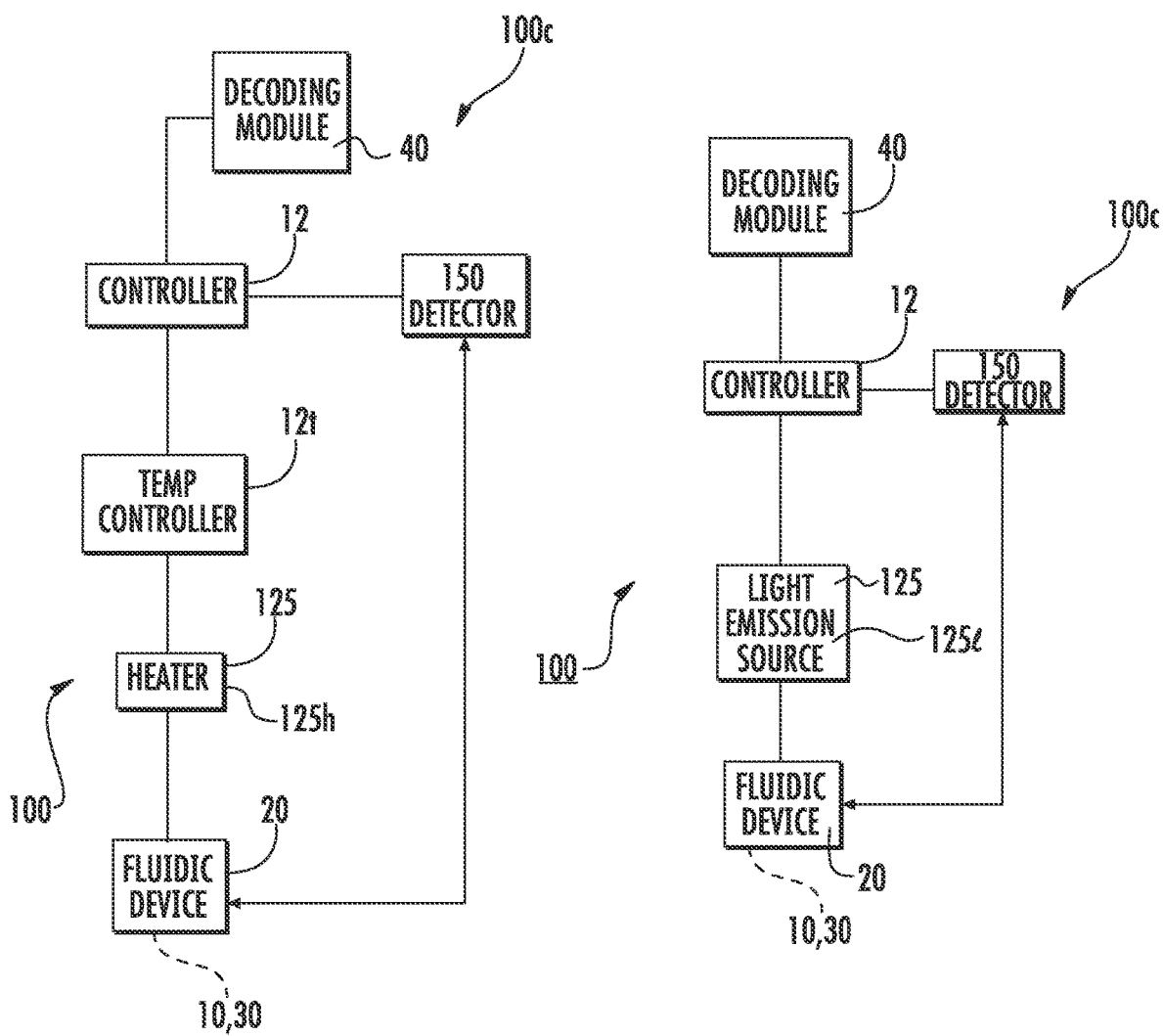
FIGS. 13A-13C are schematic illustrations of exemplary analysis systems according to embodiments of the present invention.

FIG. 13A illustrates an analysis system 100 with a Defined Event device 125 comprising at least one heater input 125*h* as the Dynamic Event applicator. The heater 125*h* can be a heating element residing under and/or over the array 30, an oven or heat gun or other appropriate heater. The thermal Defined Event input can be configured to elevate the temperature to above ambient temperature, typically to at least 1 degree above 25 degrees C., typically between about 35° C. and 200° C. The heater 125*h* can apply the critical temperature to the array 30 for between 1 microsecond –50 hours, typically between about 1 second to about 5 minutes, in some embodiments. The solid supports 10 can return to ambient or room temperature and/or to about 25° C. or other temperature, typically to about the same temperature as that used for the decoding image taken before the Defined Event, before the detector 150 takes a post Defined Event image(s). Forced cooling or passive cooling may be used once the heat input is removed.

FIG. 13B illustrates an analysis system 100 with a Defined Event device 125 comprising at least one light source 125*l* as the Dynamic Event applicator. The light source 125*l* can be a single emitter that transmits light at a defined wavelength or wavelength range or may comprise a plurality of emitters at different wavelengths, wavelength ranges or a plurality of emitters at the same wavelength or wavelength range to cover a larger area, for example. The Defined Event input 125*l* can be configured to actively transmit light to the solid supports 10 for a suitable time, such as between about 1 microsecond to 50 hours, typically between 1 second and 5 minutes, as described above.

Figure 13C:
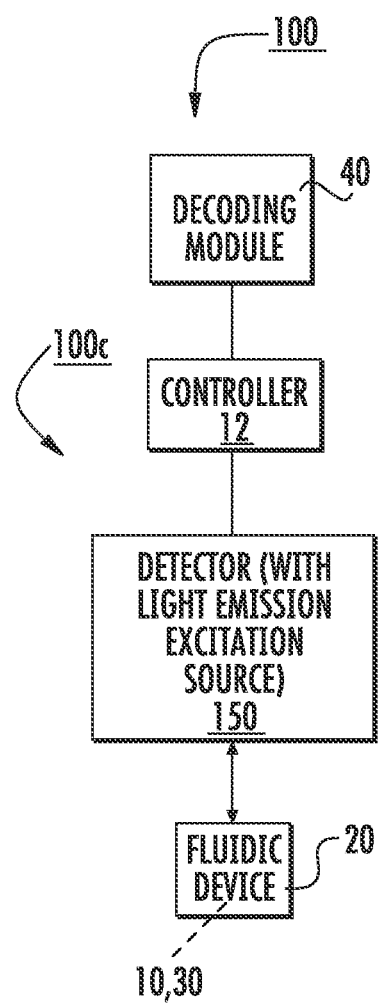

FIG. 13C illustrates an analysis system 100 with a circuit 100*c* where the detector 150 is the Defined Event device, which includes associated light emission sources as known to those of skill in the art.

As illustrated in FIGS. 14A-14E, a microfluidic device 20 may include a well array 30 with a plurality of wells 10. The wells 10 can hold beads 25 in the bead retention segments 11. The beads 25 can optionally comprise primers attached thereto and may optionally be pre-loaded into the bead retention segments 11 of the wells 10. The device 20 may comprise upper and lower substrates 50*u*, 50*b* (FIGS. 14B, 14C) that attach together. The upper substrate 50*u* may be the same or different from the lower substrate 50*b*. Either or both substrates 50*u* can be rigid and comprise glass, quartz, silicon, or a suitable metal for example. Either or both substrates 50*b* may be polymeric, such as silicone or other polymeric material (such as PMMA, COC, COP, PDMS, PP, PE, PTFE, or Kapton (polyamide), among many others), and it can provide the array of bead wells 10. The upper or lower substrate 50*u* can have at least one port 50*p* in fluid communication with the wells 10. The reaction wells 10 can optionally be perpendicular to flow through the array chamber with the array of wells 30 during reagent filling and/or oil sealing, for example: however, other alignment configurations may be used.

Figure 14A:
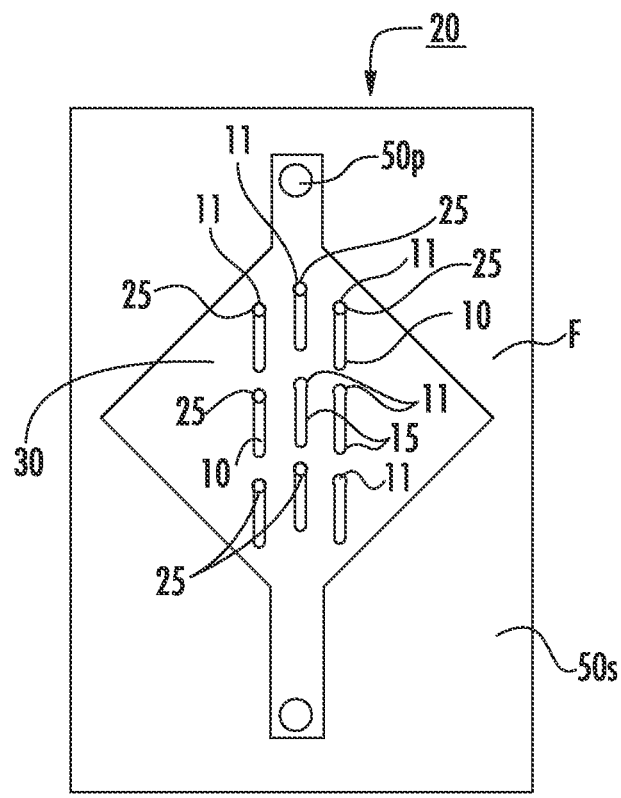
FIG. 14A is a top view of an exemplary microfluidic chip according to embodiments of the present invention.
Figure 14B:
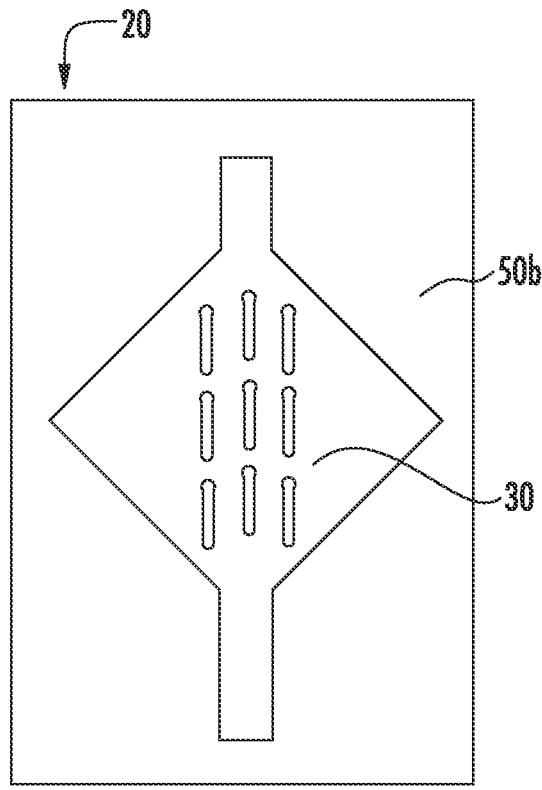
FIGS. 14B and 14C are top views of exemplary attachable substrates for the microfluidic chip shown in FIG. 14A according to embodiments of the present invention.
Figure 14C:
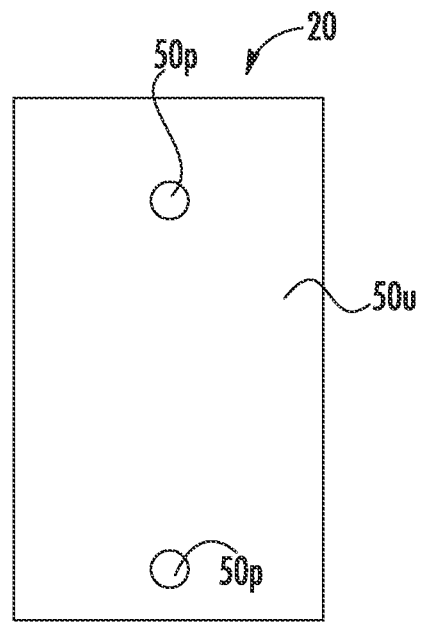

FIG. 14A shows that the microfluidic chip 20 can be configured so that the array of bead wells 30 occupy a footprint "F" (typically between 1 mm and 10 cm) with a dense array wells. The fluidic microchip 20 can include transport channel(s) for a sample and reagents or other chemical additions that can be in fluid communication with the array 30 as is well known to those of skill in the art.

Figure 14D:
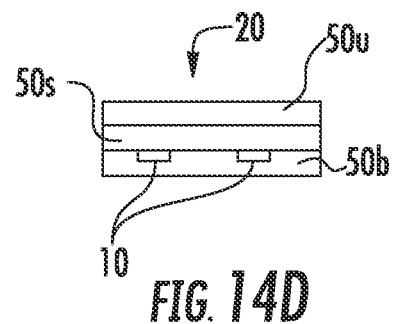
FIG. 14D is a sectional view of a microfluidic chip illustrating an optional spacer according to embodiments of the present invention.

FIG. 14D illustrates an optional spacer 50*s* that may reside between the upper and lower substrates 50*u*, 50*b*. The spacer 50*s* can define sidewalls of some or all of a respective well 10. The spacer 50*s* can comprise a photoresist used as both a gasket and spacer.

Figure 14E:
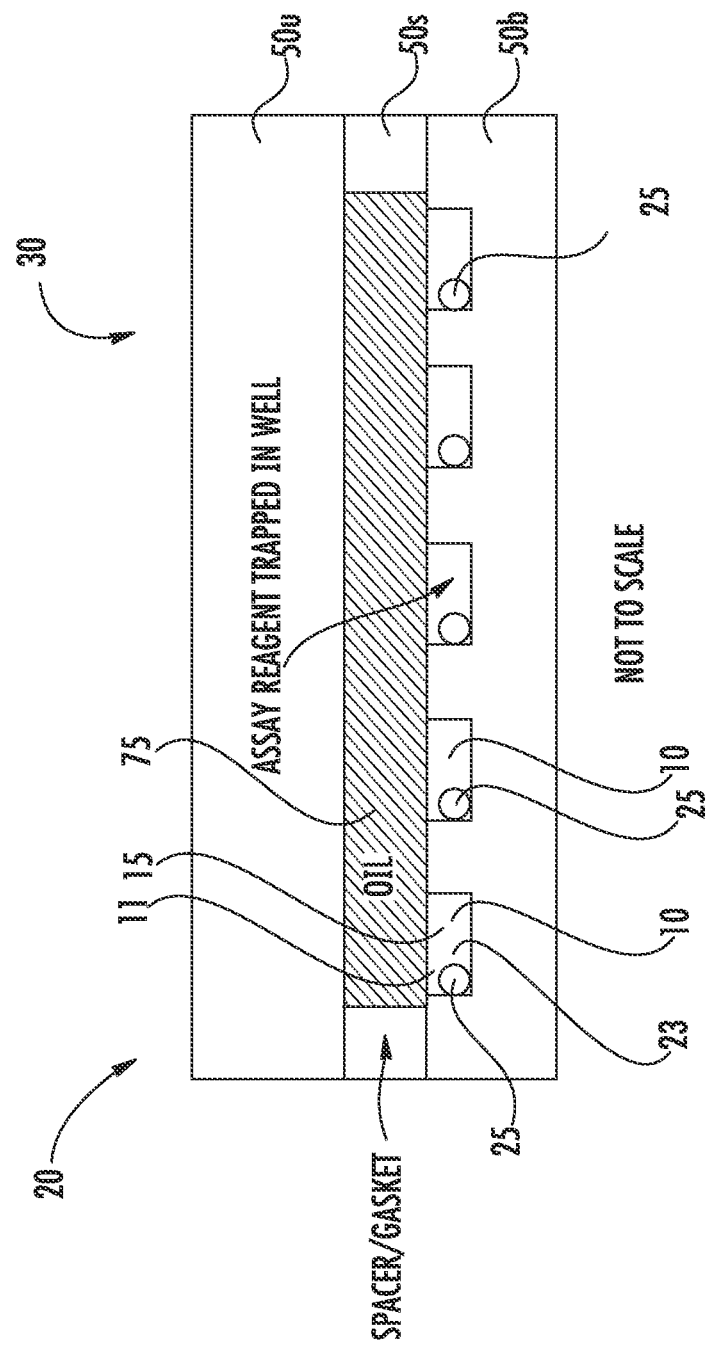
FIG. 14E is a section view of an exemplary microfluidic chip illustrating the use of a sealing agent between adjacent reaction wells according to embodiments of the present invention.

FIG. 14E illustrates that a sealing agent 75 such as sealing oil can separate adjacent wells 10 with beads 25 as is well known to those of skill in the art. Hydrophobic membrane(s) may also or alternatively be used. The sealing agent 75 (e.g., oil) can extend over the top of the bottom substrate 50*b*. The sealing agent 75 can have a thickness or depth associated with the spacer/gasket 50*s*. The sealing agent 75 and can cover everything but the bead/reaction well 10. The sealing agent 75 can comprise mineral, silicone, hydrocarbon or fluorocarbon-based oil and/or waxes. The reaction solution 23, e.g., an aqueous solution, does not typically touch the top substrate 50*u*.

This technology may be particularly advantageous for bead-based assays involving amplification methods such as the polymerase chain reaction (PCR) or enzyme-linked immunosorbent assays (ELISA) that use fluorescence signal readout in analog or digital detection modes. In these assays, zero, one, or multiple analyte molecules are captured by a solid support, which may optionally comprise a bead such as a magnetic bead. The solid support can then be loaded into a microwell array 30 with a geometry that restricts the loading of the solid supports 25 to one or zero per well 10. A small volume of amplification reagents can be sealed in each reaction well 10 with the solid support 25, and a chemical reaction can be performed to produce a fluorescence signal if the analyte molecule is present. The assay fluorescence signal can then be measured, processed, and used to determine analyte concentration in the sample.

Singleplex Reactions in a Compact Array (SiRCA) is a massively parallel amplification and detection method using a microbead-array format that has the potential to perform, hundreds, thousands, millions or billions of isolated, singleplex rt-PCR reactions for many different target sequences simultaneously. See, e.g., U.S. patent application Ser. No. 14/402,565, describing, for example, bead-based delivery of reagents for parallel assays on a multiplexed-in-space microfluidic device; the contents of this document are hereby incorporated by reference as if recited in full herein.

The ability to perform single copy, digital quantification at low analyte concentrations and multiple copy, analog rt-PCR quantification at high analyte concentrations gives a large dynamic range with aM LODs. In some embodiments, the arrays 30 can be used with individual sets of biotinylated primers that are attached to dye encoded, streptavidin-labeled, magnetic microspheres or beads. A bead set library containing up to tens to hundreds of bead types can be made, each with a different primer set for a different target sequence, and new bead sets can be added to the bead mixture at will. When the bead mixture is incubated with analyte DNA or RNA, the primers attached to the beads act as hybridization probes, capturing and purifying the nucleic acid sequence specific to that bead. Sample matrix interferents (extraneous DNA, RNA, cell membrane components, etc.) can be removed by separating the beads magnetically and washing. After cleanup, polymerase, dNTPs, and intercalating dye are added, and the beads are loaded into individual wells 10 and sealed from one another using an immiscible oil or hydrophobic membrane. Stochastically loading individual, encoded primer beads into separate microreaction wells can be accomplished in a matter of seconds to minutes, unlike hand pipetting or reagent printing. Magnetic loading of beads into optimized geometries can be more efficient than random isolation by dilution into droplets or reaction wells that do not contain regions designed for bead capture and/or a separate detection region for a well 10. The streptavidin/biotin interaction is very stable at temperatures below 50° C.; however, elevated temperatures used for denaturation during PCR may allow the subsequent release of the primers during the first rt-PCR cycle initiating amplification of target DNA.

In order to evaluate the performance of SiRCA in sub-pL reactions, preliminary testing without beads using primers and gDNA was performed in silicon fluidic chips with arrays of wells 3.7 μm in diameter, 5 μm deep (cylindrical with volume≈50 fL) with a center-to-center spacing of 10 μm, fabricated by deep reactive ion etching (DRIE) in silicon. Thus, the rt-PCR performed in ≈50 fL cylindrical reaction wells with primers and gDNA free in solution without beads. Chips were pretreated with octyltrichlorosilane in heptane to render the surfaces hydrophobic. The chips were wet with ethanol, then water, and then blocked with loading buffer (20 mM Trizma, 50 mM KCl, 2.5 mM $MgCl_2$, 1% BSA, and 0.1% Tween 20). Master mix (1× Platinum Quantitative PCR SuperMix-UDG with 0.0625 units/4 additional Platinum Taq DNA polymerase, 0.5% BSA, 2.7 μM primers, gDNA from *S. mutans*, and 3×SYBR Green) was added to the chip and then Krytox GPL104 perfluorinated oil was pulled through the chip to seal the reaction volumes from one another.

Figure 19:
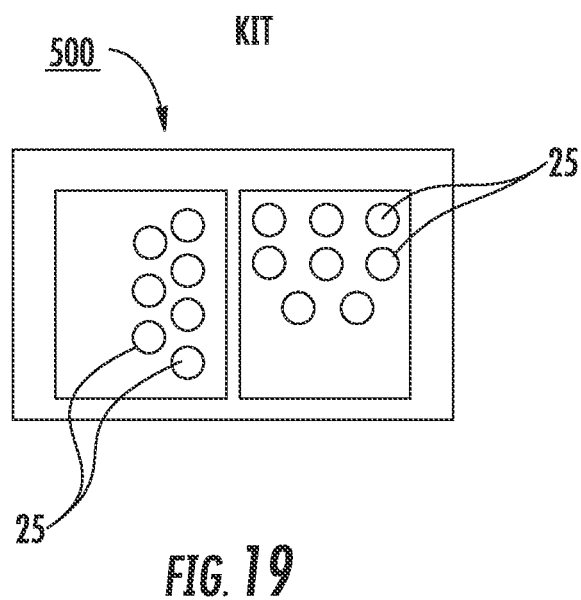
FIG. 19 is an illustration of a package with a kit according to embodiments of the present invention.

Embodiments of the invention comprise reaction wells 10 with geometries configured to contain more than one bead so that a reaction between reagents released from one or more beads and reacting in solution or upon the surface of one or more beads or any combination thereof can be studied at a designated detection region(s) as shown or alternatively upon a bead's surface. The bead well arrays 30 can include variations where some wells 10 hold one bead 25, some wells 10 hold two beads 25, and some wells 10 hold more than two beads 25 on a single substrate or fluidic device or on separate substrates or devices. Where a well 10 includes more than one bead retention segment 11, a plurality (typically each) of bead retention segments 11 can be in fluid communication with each other via a signal detection segment such as a fluidic channel 15*ch*. Kits useful for carrying out the methods of the present invention can, in general, comprise one or more sets of beads having encoding agents and, optionally, reagents attached thereto for carrying out the methods as described above, such as restriction enzymes, optionally packaged with suitable instructions for carrying out the methods. The kits may also include containers for housing elements included therein. Such containers include, but are not limited to vials, microfluidic chips with bead well arrays and cartridges, including preloaded bead devices. FIG. 19 illustrates a package with a kit 500 of encoded beads 25 suitable for a dynamic decoding protocol. The kit 500 may include one type/population of encoded beads 25 (i.e., beads that all have the same encoding signal or "fingerprint") or may include two or more different types/populations of encoded beads 25 (i.e., at least two different bead populations, one having a first encoding signal and one having a second encoding signal that is different than the first). When the kit 500 includes a two or more different types of encoded beads 25, the kit 500 may include the encoded beads 25 as a mixture in a single package or may separately package each encoded bead population (e.g., separately package the bead population with the first encoding signal and separately package the bead population with the second encoding signal).

In some embodiments, the beads 25 may have primers attached thereto. The primers may be a pair of biotinylated primers, and the beads 25 may be streptavidin-labeled such that binding of the biotinylated primers to the beads occurs. In some embodiments, the beads 25 may include a marker, such as an optical marker, that may be used during analysis to identify the primers anchored to the respective beads 25. For example, different encoded beads of the same or different sizes may be marked for identification of different attached primer sets during analysis. Various pre-encoding methods may be used to provide a marker on the beads 25, including a predefined size, shape, magnetic property and/or fluorescence doping used alone or in combination with other encoding methods. Both custom-sequence biotinylated primers and streptavidin labeled paramagnetic magnetic beads can be readily purchased from commercial vendors or made in a suitable quantity in an appropriately equipped laboratory.

As noted above, although embodiments according to the present invention are also described herein with respect to PCR reactions, it should be understood that the microfluidic devices, beads and reaction methods described herein may be used in various other reactions, e.g., where reagents are cleaved from a bead into a well to participate in a reaction. For example, any nucleic acid transcription and/or amplification-related reaction is within the scope of the current invention, including but not limited to PCR reactions, real-time PCR (rt-PCR), digital PCR (dPCR), reverse transcription of RNA into cDNA (RT), PCR of cDNA from previous RT step (RT-PCR), RT-PCR using real-time or digital quantification, immuno-PCR (iPCR) and its variants, loop-mediated isothermal amplification (LAMP), rolling circle replication, and/or non-enzymatic nucleic acid amplification methods (e.g., "DNA circuits"). Other reactions that are included within the scope of the present invention include but are not limited to enzyme-linked immunosorbent assays (ELISA), single molecule array (SiMoA) or digital ELISAs, ELISAs where the fluorogenic substrate is bound to the support surface to be cleaved at some point for subsequent reaction, reactions in which multiple beads are used to deliver different reagents for combinatorial chemistry, reactions where the beads deliver a catalyst reagent, and/or reactions where "click" chemistry reagents are delivered in stoichiometries determined by stochastic bead loading.

Figure 15:
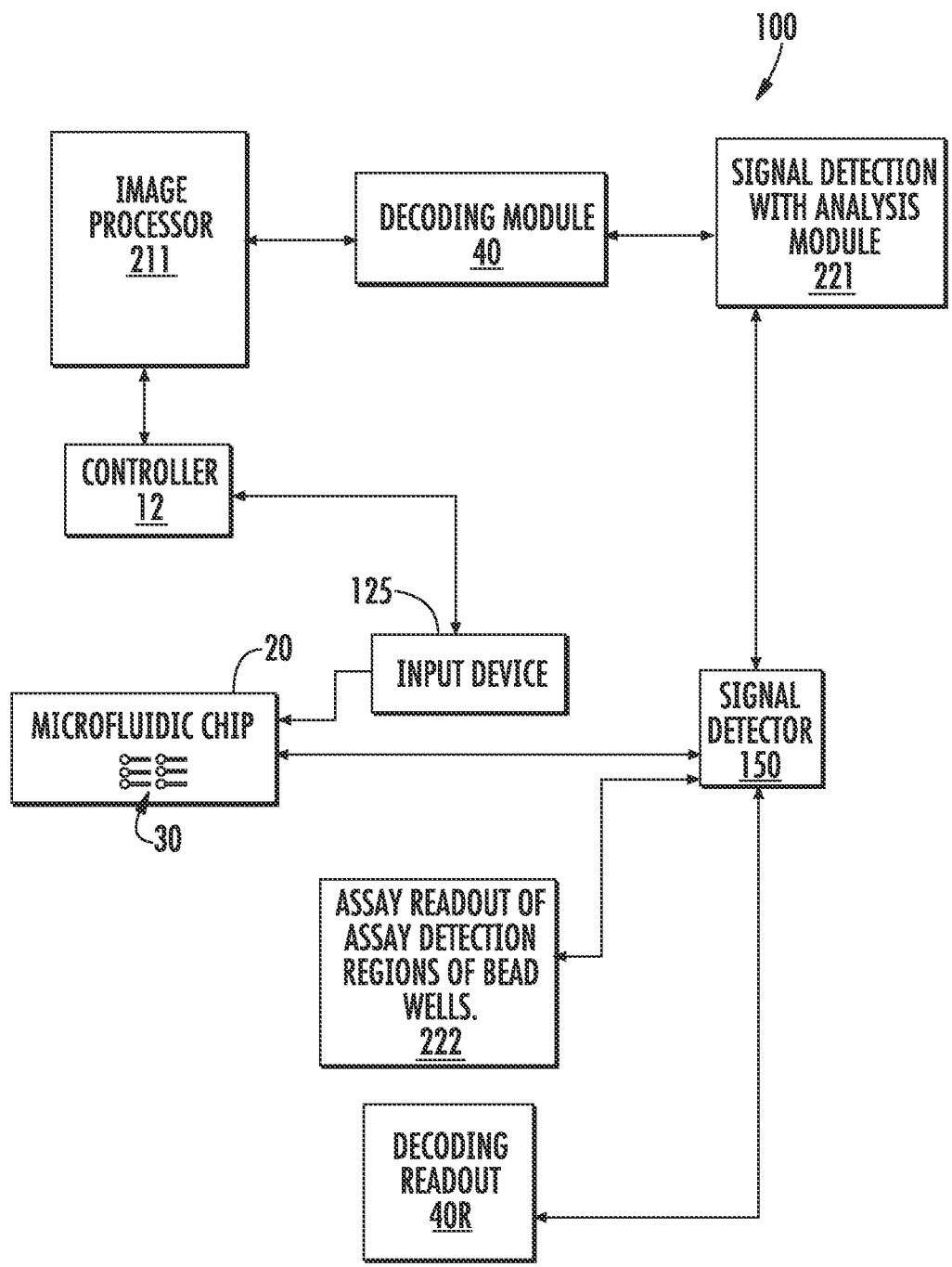
FIG. 15 is a schematic illustration of an analysis system according to embodiments of the present invention.

FIG. 15 is a schematic illustration of an analysis system 100. The system 100 can include at least one controller 12 (typically comprising at least one processor) in communication with a signal detector 150 such as a camera or other imaging device. The signal detector 150 can be configured to detect a signal (e.g., an assay signal and/or an encoding signal) of the solid substrate(s) such as beads 25 in a bead well array 30 of a respective microfluidic chip 20 with an array of wells 30. The controller 12 can be in communication with an input device 125. Although shown as a separate device, the input device 125, can exist as a part of the system instrumentation. For example, the input device 125 can be the and/or a part of the optics system, imaging device, thermal device, etc. The controller 12 can be in communication with an image processor 211 having a signal detection with analysis module 221 (e.g., computer program) configured to identify if an assay signal is present in signal detection segments of the reaction wells and a decoding module 40 configured to obtain encoding signal(s). The image processor module 211 can be totally or partially onboard or remote from the controller and/or signal detector 150. The image processor module 211 can be configured to combine a plurality of post-assay images of the wells to assess whether a well has a positive readout. The image processor module 211 may remove the background noise from the bead retention segment of respective wells. The module 211 may be configured to identify the presence of a signal from the detection segment(s) of a respective well to identify whether a positive assay reaction occurred based on an assay readout 222. The detector 150 can also detect encoding signal(s) using a decoding readout 40R.

Figure 16:
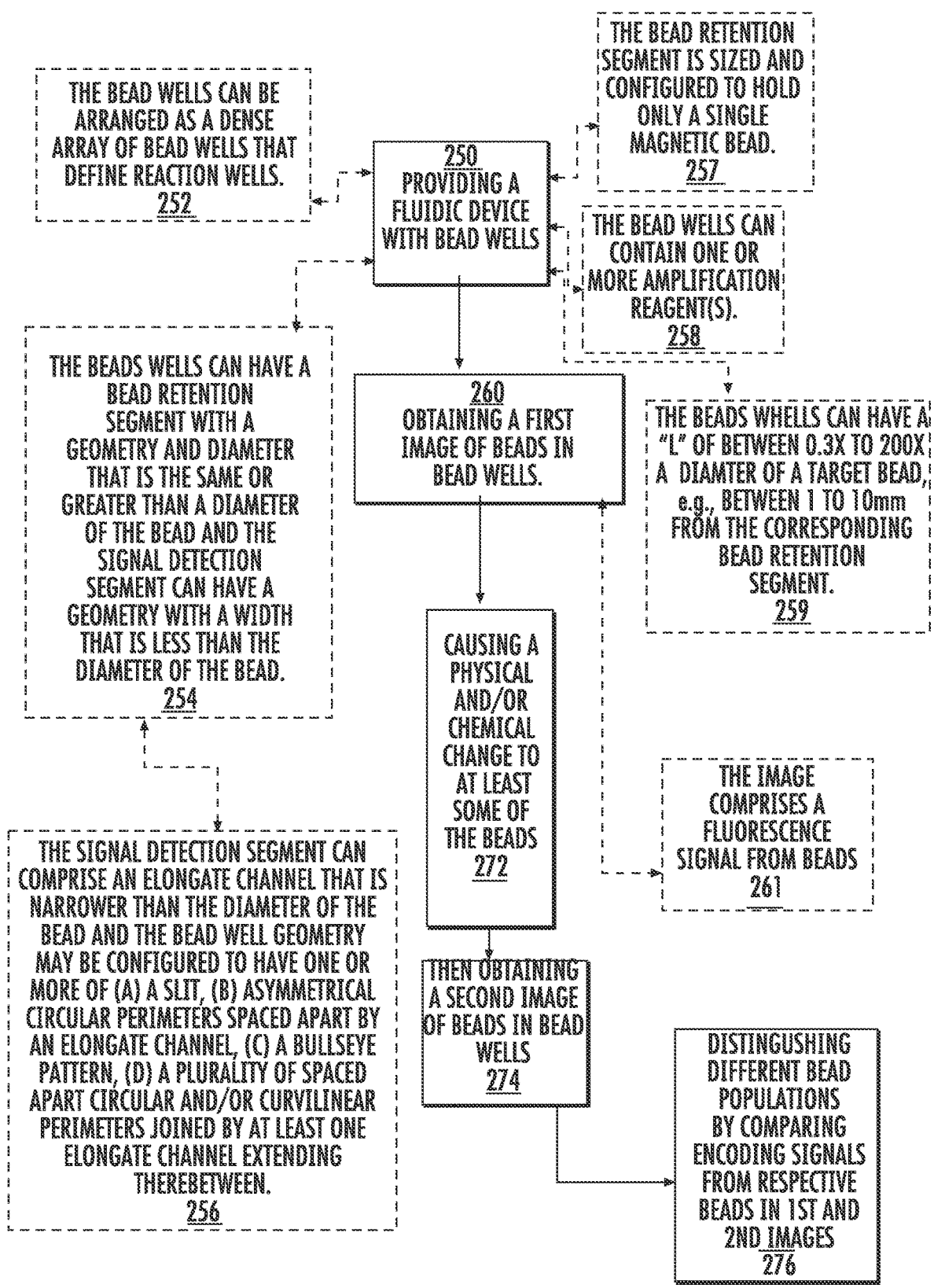
FIGS. 16-18 are flow charts representing exemplary methods of embodiments of the present invention.

FIG. 16 is a flow chart of example operations that can be used to carry out analysis methods according to embodiments of the present invention. A fluidic device with bead wells is provided (block 250). An encoding signal is obtained from the wells while beads are retained in bead wells, which may include obtaining a first image of beads retained in the bead wells (block 260). A physical and/or chemical change then occurs for at least some of the beads (block 272). A second image is then obtained (block 274). Different bead populations are distinguished by comparing the encoding signals from respective beads in the first and second images (block 276).

In these and/or other embodiments, an encoding signal can be read from the bead containing segment (i.e. directly from the bead) to ascertain what reagent(s) and/or analyte the bead may contain. In this manner, the array can be decoded to determine the meaning of a positive or negative assay signal. Beads may be encoded by means known to those skilled in the art, including fluorescent dye staining by one or more dyes at one or more intensity levels, bead diameter, bead shape, or any combination of defined and/or observable or detectable properties. Beads may also be encoded by any of the methods described herein.

The bead wells can be arranged as a dense array of bead wells that define reaction wells (block 252). The bead wells can have a bead retention segment can have a geometry and diameter that is the same or greater than a diameter of the bead and the signal detection segment, where used, has a geometry with a width that is less than the diameter of the bead (block 254).

The signal detection segment can comprise an elongate channel that is narrower than the diameter of the bead and the bead well geometry may be configured to have one or more of (a) a slit, (b) asymmetrical circular perimeters spaced apart by an elongate channel, (c) a bulls-eye pattern (i.e., an elongate channel merging into an annular channel), (d) a plurality of spaced apart circular and/or curvilinear perimeters joined by at least one elongate channel extending therebetween (block 256).

The bead retention segment can be sized and configured to hold only a single magnetic bead (block 257).

The bead wells can contain one or more amplification reagent(s) (block 258).

The bead wells can have a detection segment can be spaced apart a distance L of between 0.3× and 100× the diameter of a target bead, e.g., between 1 to 1000 μm, from the corresponding bead retention segment (block 259).

The signal can include a fluorescence signal (with a tail) if an analyte molecule is present (block 261).

Figure 17:
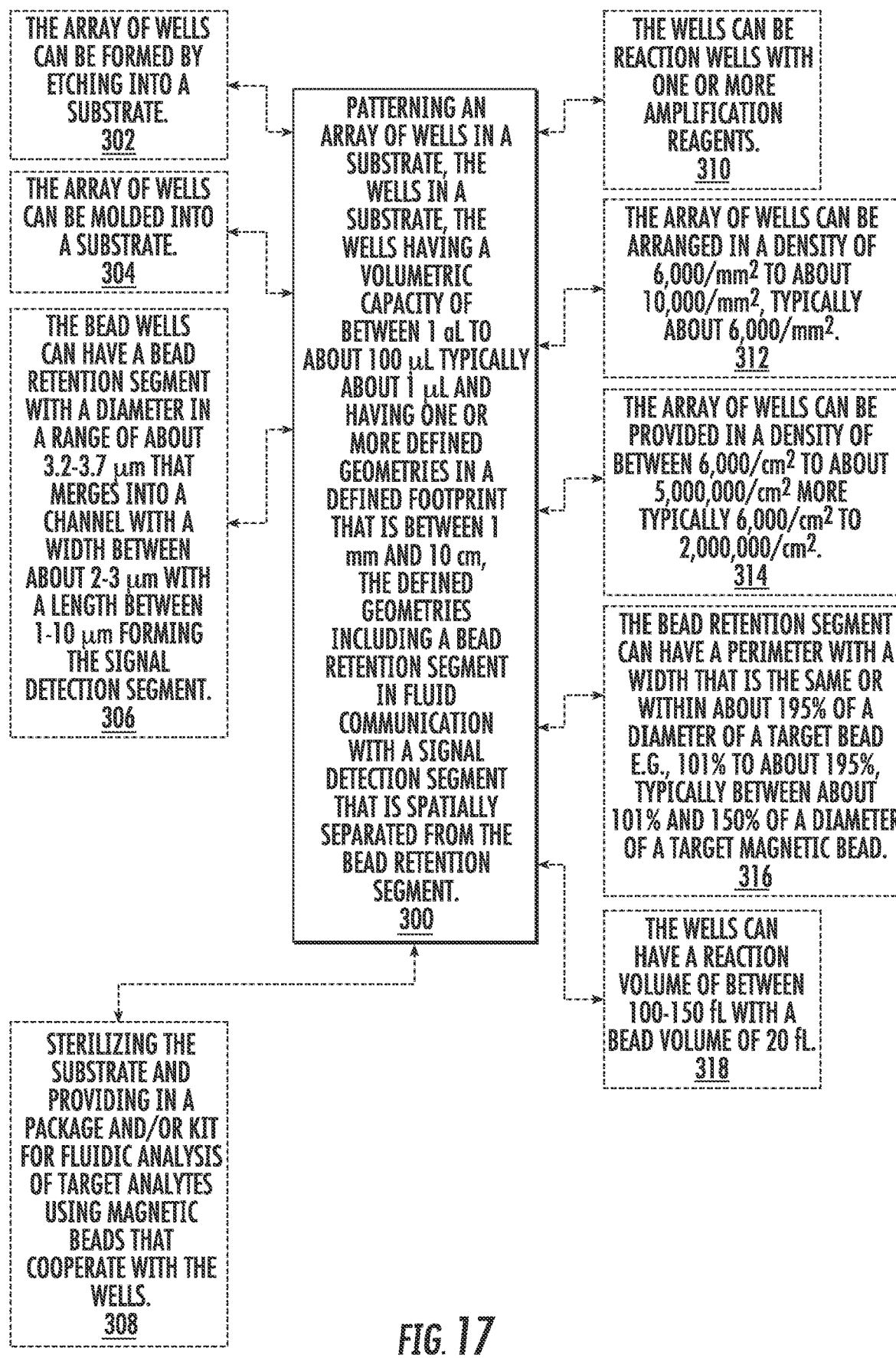

FIG. 17 is a flow chart of a method of fabricating exemplary devices according to embodiments of the present invention. An array of wells is patterned (e.g., formed) in a substrate; the wells have a volumetric capacity of between 1 aL to 100 μL, more typically between 1 fL and 1 μL, and one or more defined geometries in a defined footprint with linear dimensions between 1 mm and 10 cm, the defined geometries including a bead retention segment in fluid communication with a signal detection segment that is spatially separated from the bead retention segment (block 300).

The array of wells can be formed by etching into a substrate (block 302).

The array of wells can be molded into a substrate (block 304). Other fabrication methods are contemplated, e.g., photolithography, FIB milling, embossing, stamping and the like.

The bead wells may have a bead retention segment with a diameter in a range of about 10 nm and 5,000 μm, typically between about 3.1-3300 μm that merges into a channel with a width between about 2-3 μm with a length L of between 0.3× and 100× the diameter of a target bead, e.g., between 1-100 μm and/or between 1-10 μm, in some embodiments, forming the optional signal detection segment (block 306).

Sterilizing the substrate and providing in a package and/or kit for fluidic analysis of target analytes using magnetic beads that cooperate with the wells (block 308).

The wells can be reaction wells with one or more amplification reagents.

The array of wells can be arranged in a density of 6000/mm² to about 10,000/mm², typically about 6,000/mm² (block 312).

The array of wells can be provided in a density of between 6,000/cm² to about 5,000,000/cm², more typically 6,000/cm² to about 2,000,000/cm², (block 314).

The bead retention segment can have a perimeter with a width that is the same or within about 195% of a diameter of a target (e.g., magnetic) bead, e.g., between 101% and 195% or 150% of the diameter of a target bead (block 316).

The wells can have a reaction volume of between 100-150 fL with a bead volume of 20 fL (block 318).

Figure 18:
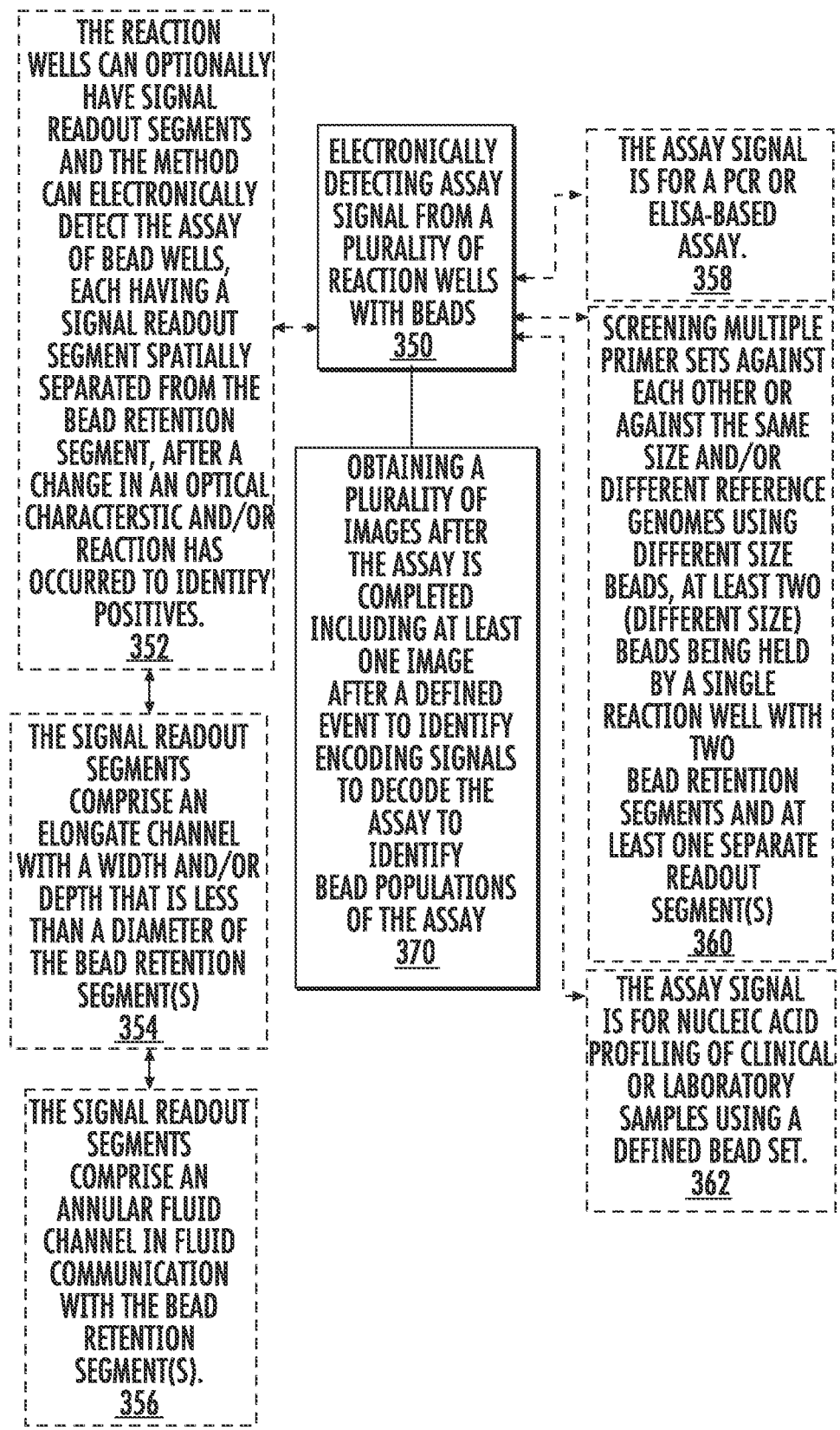

FIG. 18 is a flowchart of a method of evaluating an assay according to embodiments of the present invention. Assay signal is electronically detected from a plurality of reaction wells with beads (block 350). The term "electronically" refers to all forms of machine based detection (not human vision) such as a camera, e.g., a CCD camera, a CMOS camera, an array of electrodes, a SEM, and the like. The signal can be an increase in intensity, fluorescence, one or more defined colors, a defined pixel parameter and the like, including a change in light scattering properties (transparence), a change in transmittance or absorbance, chemiluminescence or combinations of different parameters. Before, during, and/or after the assay is completed, a plurality of images are obtained including a first image and obtaining a subsequent image after a Defined Event to identify encoding signals to decode the assay to identify bead populations in the assay sample (block 370).

The reaction wells can optionally have signal readout segments, and the method can electronically detect assay signal from an array of bead wells, each having a signal readout segment spatially separated from the bead retention segment, after a reaction has occurred to identify positives (block 352).

The signal readout segments comprise an elongate channel with a width and/or depth that is less than a diameter of the bead retention segment(s) (block 354).

The signal readout segments comprise an annular fluid channel in fluid communication with the bead retention segment(s) (block 356).

The assay signal is for a PCR or ELISA-based assays (block 358).

Multiple primer sets can be screened against each other or against different reference genomes using the same size beads or different size beads, at least two beads being held by a single reaction well with two (optionally different size) bead retention segments and at least one separate readout segment(s) (block 360). These beads may be encoded by any of the methods listed herein or those sources referenced herein.

The assay signal can be for nucleic acid profiling of clinical or laboratory samples using a defined bead set (block 362).

Prophetic Examples 1-10

The prophetic example embodiments below are described with respect to a plurality of beads that can be decoded using methods of the present invention to identify different bead populations. However, other types of solid supports may be utilized. In addition, each of the below prophetic example embodiments may be combined with one or more embodiments that utilize the time domain with respect to the same and/or a different Defined Event. For example, a plurality of beads may include one or more populations of beads that can be identified using an encoding agent that physically and/or chemically changes in response to photoexposure at a given wavelength and may include one or populations of beads that can be identified using an encoding agent that physically and/or chemically changes in response to photoexposure at the same and/or a different wavelength and/or that changes in response to temperature and/or the chemical environment. For example, the encoding signal generated by the encoding agent for a respective bead prior to the physical and/or chemical change may be different than the encoding signal generated by the encoding agent for the respective bead after the physical and/or chemical change In each of Examples 1-10, a plurality of encoded beads may be provided that includes different bead populations/subsets that can be identified by comparing the fluorescence intensity from first and/or second encoding agents attached to each bead at a first point in time before a Defined Event and an additional point in time during and/or after the Defined Event. A first bead population may include a first encoding agent (e.g., FP, organic dye and/or quantum dot) attached thereto and a second bead population may include a second encoding agent (e.g., FP, organic dye and/or quantum dot) attached thereto. Additional bead populations may include both the first and second encoding agents attached thereto in different ratios (e.g., in a ratio of first encoding agent:second encoding agent of 25:75, 50:50, or 75:25). For example, a third population may have a ratio of 30:70, a fourth population may a ratio of 50:50, etc. The first and second encoding agents may have the same and/or similar fluorescence excitation/emission properties and/or intensities such that the first, second, and additional bead populations are indistinguishable at the first point in time prior to the Defined Event. However, at least one of the encoding agents may not be stable with respect to the Defined Event. Thus, during and/or after exposure to the Defined Event, the first and second encoding agents may exhibit different fluorescence intensities, which allows for the two encoding agents to be distinguished. Thus, the first and second bead populations may be identified by comparing the fluorescence intensity before the Defined Event with the fluorescence intensity during and/or after the Defined Event. The additional bead populations may also be identified by the fluorescence intensity or change in fluorescence intensity after the Defined Event as the ratio provides different levels or a gradient of fluorescence intensities between the intensities for the first and second encoding agents. The number of additional bead populations that may be provided may depend on the number of additional fluorescence intensities that can be identified (i.e., that are distinguishable) at a point in time during and/or after the Defined Event.

In these examples, it should be noted that it would be advantageous to have many populations of substrates that can be distinguished based upon an initial reading or measurements of their properties, but within each initially distinguishable population there are different subpopulations that may not be initially identifiable. After the Defined Event (or a series of Defined Events or multiple simultaneously occurring Defined Events), the different subpopulations will be distinguishable and identifiable by a comparison of their initial signal measurements to the signal measurements occurring after and/or during the Defined Event(s). In this manner, all multiplexed populations are resolved from one another by the decoding. Although populations may be described below as indistinguishable, it should be noted that they can describe initially indistinguishable subpopulations of larger substrate sets that may have some distinguishable properties that allow an initial classification. Although Defined Events may be described below to cause physical and/or chemical changes that create different intensity levels for a given subpopulation, it should be noted that these resulting intensity levels are "different" as compared to that measured for that particular subpopulation before the Defined Event and may, in some cases, correspond to intensity levels that are similar to or the same as initial intensity levels or final intensity levels for other subpopulations that were distinguished from the given subpopulation by another distinguishable property either before, after, or during the Defined Event. Thus, comparison of the encoding signal for a particular bead at different points in time, which may include points in time before, after, or during a Defined Event, may be used to distinguish the bead from another bead.

Example 1

Photostability of organic dyes in the time domain may be used to decode the plurality of encoded beads. A first bead population may include a first organic dye attached thereto and a second bead population may include a second organic dye attached thereto. Additional bead populations may include both the first and second organic dyes attached thereto in different ratios as described above. The first and second organic dyes may have the same and/or similar fluorescence excitation/emission properties and/or intensities such that the first, second, and additional bead populations are indistinguishable at the first point in time prior to the Defined Event. The first and second organic dyes may be susceptible to different levels of photobleaching upon exposure to light for a defined time, typically between about 30 seconds and five minutes, such as about 1 minute, about 2 minutes, about 3 minutes or more. Thus, after photobleaching for the defined time, e.g., at least one microsecond, the different bead populations have different fluorescence intensities. For example, the first organic dye may be not as susceptible (i.e., more stable) to photobleaching compared to the second organic dye (i.e., the dynamic element) and the fluorescence intensity for the first organic dye may only reduce by 10% after 1 minute, whereas the fluorescence intensity for the second organic dye may reduce by 90% after 1 minute. Thus, the first and second bead populations may be identified by the fluorescence intensity after the Defined Event (i.e., photobleaching). The additional bead populations may also be identified by the fluorescence intensity after the defined event as the ratio provides different levels or a gradient of fluorescence intensities between the intensities for the first and second organic dyes.

Example 2

Photostability of an organic dye and quantum dot in the time domain may be used to decode the plurality of encoded beads. A first bead population may include an organic dye attached thereto and a second bead population may include a quantum dot attached thereto. Additional bead populations may include both the first organic dye and organic dot attached thereto in different ratios as described above. The first organic dye and quantum dot may have the same and/or similar fluorescence excitation/emission properties and/or intensities such that the first, second, and additional bead populations are indistinguishable at the first point in time prior to the Defined Event. The first organic dye (i.e., the dynamic element) may be susceptible photobleaching upon exposure to light for 1 minute or more, whereas the quantum dot is not susceptible to photobleaching. Thus, after photobleaching for at least one minute the different bead populations have different fluorescence intensities. For example, the fluorescence intensity for beads with only the first organic dye may by significantly reduced after a defined time, e.g., 1 minute, whereas the fluorescence intensity for beads with only the quantum dot may not be reduced after 1 minute. Thus, the first and second bead populations may be identified by the fluorescence intensity after the Defined Event (i.e., photobleaching). The additional bead populations may also be identified by the fluorescence intensity after the Defined Event as the ratio provides different levels or a gradient of fluorescence intensities between the intensities for the first organic dye and quantum dot.

Example 3

Thermal stability of an encoding agent may be used to decode the plurality of encoded beads by comparing the fluorescence intensity from first and/or second encoding agents attached to each bead at a first point in time before a thermal Defined Event and at an additional point in time during and/or after the thermal Defined Event. A first bead population may include a first encoding agent (e.g., organic dye and/or quantum dot) attached thereto and a second bead population may include a second encoding agent (e.g., organic dye and/or quantum dot) attached thereto. Additional bead populations may include both the first and second encoding agents attached thereto in different ratios as described above. At least one of the encoding agents may not be stable to an increase or decrease in temperature. For example, an encoding agent (i.e., the dynamic element) in response to a defined thermal event may change in structure and/or charge, which may provide a change in the fluorescence intensity of the encoding agent. In some embodiments, the thermal Defined Event may cause a change and/or disrupt the chemical bonds associated with the encoding agent and/or bead, such as, e.g., the chemical bonds of a binding pair (e.g., streptavidin-biotin) attaching the encoding agent to the bead. Thus, during and/or after exposure to a change in temperature, the first and second encoding agents may exhibit different fluorescence intensities that allows for the two encoding agents to be distinguished. Thus, the first and second bead populations may be identified by the fluorescence intensity after the Defined Event (i.e., increase or decrease in temperature). The additional bead populations may also be identified by the fluorescence intensity after the Defined Event as the ratio provides different levels or a gradient of fluorescence intensities between the intensities for the first and second encoding agents.

Example 4

A thermal Defined Event may activate or deactivate an agent (e.g., a quencher) that affects the fluorescence intensity of at least one of the encoding agents (i.e., the dynamic element). For example, a heat-labile compound may be activated by a thermal Defined Event where the temperature is increased. The agent in response to the thermal Defined Event may interact with an encoding agent, no longer interact with the encoding agent, and/or may affect the chemical properties of the environment in which the encoding agent is present (e.g., change the pH), which may provide a change in the fluorescence intensity of the encoding agent. Thus, during and/or after exposure to the thermal Defined Event, the first and second encoding agents may exhibit different fluorescence intensities that allows for the two encoding agents to be distinguished. Thus, the first and second bead populations may be identified by the fluorescence intensity after the defined event (i.e., increase or decrease in temperature). The additional bead populations may also be identified by the fluorescence intensity after the defined event as the ratio provides different levels or a gradient of fluorescence intensities between the intensities for the first and second encoding agents.

Example 5

An optical Defined Event may activate or deactivate an agent (e.g., a quencher) that affects the fluorescence intensity of at least one of the encoding agents (i.e., the dynamic element). For example, a photoactivated compound may be present with the encoded beads and may be activated by an optical Defined Event where light is exposed to the encoded beads and agent. The agent in response to the Defined Event may interact with an encoding agent, no longer interact with the encoding agent, and/or may affect the chemical properties of the environment in which the encoding agent is present (e.g., change the pH), which may provide a change in the fluorescence intensity of the encoding agent. Thus, during and/or after exposure to the optical Defined Event, the first and second encoding agents may exhibit different fluorescence intensities that allows for the two encoding agents to be distinguished. Thus, the first and second bead populations may be identified by the fluorescence intensity after the defined optical event (e.g., exposure to light of a given wavelength and/or wavelength range). The additional bead populations may also be identified by the fluorescence intensity after the Defined Event as the ratio provides different levels or a gradient of fluorescence intensities between the intensities for the first and second encoding agents.

Example 6

A chemical Defined Event may be used to identify different bead populations/subsets. A change in the chemical environment may cause a change in the fluorescence intensity of at least one of the encoding agents. For example, the chemical Defined Event may cause and/or provide a change in pH of the bead environment, change the composition (e.g., remove and/or add a chemical/ingredient and/or change a solvent), activate or deactivate an agent (e.g., a quencher) that affects the fluorescence intensity of at least one of the encoding agents, and/or change the stability of a binding complex, which may cause a change in fluorescence intensity of the encoding agent. Accordingly, during and/or after the Defined Event, the first and second encoding agents may exhibit different fluorescence intensities that allows for the two encoding agents to be distinguished. Thus, the first and second bead populations may be identified by the fluorescence intensity after the Defined Event. The additional bead populations may also be identified by the fluorescence intensity after the defined event as the ratio provides different levels or a gradient of fluorescence intensities between the intensities for the first and second encoding agents.

Example 7

In some embodiments, an additional population (e.g., a third population) to those described in Examples 1-6 above may be identified if the Defined Event provides a fluorescence intensity that is exhibited after the Defined Event that was not present before the Defined Event and is different than the fluorescence intensity of the other bead populations. For example, a third bead population may include an encoding agent that does not exhibit fluorescence at a first point in time before the Defined Event. Thus, the first, second, and third bead populations are indistinguishable at a first point in time using fluorescence intensity. However, the Defined Event may activate the fluorescence of the encoding agent so that after the Defined Event a third fluorescence intensity is provided that is different than that for the first and second bead populations.

Example 8

Table 3 shows a conventional fluorescence encoding scheme where three intensity levels (low, medium, and high) of two different color dyes (red and blue) are used to encode nine populations of solid supports.

TABLE 3

|  | Low Blue (LB) | Medium Blue (MB) | High Blue (HB) |
|---|---|---|---|
| Low Red (LR) | LR (LB) | LR (MB) | LR (HB) |
| Medium Red (MR) | MR (LB) | MR (MB) | MR (HB) |
| High Red (HR) | HR (LB) | HR (MB) | HR (HB) |

Table 4 shows how encoding with four dyes (red stable, red unstable, blue stable, blue unstable i.e. only two total colors) using mixtures to obtain 6 different dynamic properties (Low that stay low, medium that stays medium, medium that bleaches low, high that stays high, high that bleaches medium, and high that bleaches low) for each color results in 36 different populations that can be distinguished using a measurement of only two colors (red and blue) and three intensities (low, medium, and high) before and after a Defined Event.

TABLE 4

|  | Low Blue (LB) | Medium Blue (MB) | Medium Blue to Low Blue (MB > LB) | High Blue (HB) | High Blue to Medium Blue (HB > MB) | High Blue to Low Blue (HB > LB) |
|---|---|---|---|---|---|---|
| Low Red (LR) | LR (LB) | LR (MB) | LR (MB > LB) | LR (HB) | LR (HB > MB) | LR (HB > LB) |
| Medium Red (MR) | MR (LB) | MR (MB) | MR (MB > LB) | MR (HB) | MR (HB > MB) | MR (HB > LB) |
| Medium Red to Low Red (MR > LR) | MR > LR (LB) | MR > LR (MB) | MR > LR (MB > LB) | MR > LR (HB) | MR > LR (HB > MB) | MR > LR (HB > LB) |

TABLE 4-continued

|  | Low Blue (LB) | Medium Blue (MB) | Medium Blue to Low Blue (MB > LB) | High Blue (HB) | High Blue to Medium Blue (HB > MB) | High Blue to Low Blue (HB > LB) |
|---|---|---|---|---|---|---|
| High Red (HR) | HR (LB) | HR (MB) | HR (MB > LB) | HR (HB) | HR (HB > MB) | HR (HB > LB) |
| High Red to Medium Red (HR > MR) | HR > MR (LB) | HR > MR (MB) | HR > MR (MB > LB) | HR > MR (HB) | HR > MR (HB > MB) | HR > MR (HB > LB) |
| High Red to Low Red (HR > LR) | HR > LR (LB) | HR > LR (MB) | HR > LR (MB > LB) | HR > LR (HB) | HR > LR (HB > MB) | HR > LR (HB > LB) |

Example 9

Table 5 shows a conventional encoding a scheme where two colors (red and blue), three intensities (low, medium, high), and two sizes (small and big) are used to encode 18 populations of substrates. It should be noted that the populations in Table 5 are similar to those in Table 3, but by adding a bead size dimension with two levels (small and big), the number of available conventional encoding levels was doubled from 9 to 18.

TABLE 5

|  | Low Blue (LB) and big | LB and small | Medium Blue (MB) and big | MB and small | High Blue (HB) and big | HB and small |
|---|---|---|---|---|---|---|
| Low Red (LR) | LR (LB) big | LR (LB) small | LR (MB) big | LR (MB) small | LR (HB) big | LR (HB) small |
| Medium Red (MR) | MR (LB) big | MR (LB) small | MR (MB) big | MR (MB) small | MR (HB) big | MR (HB) small |

TABLE 5-continued

|  | Low Blue (LB) and big | LB and small | Medium Blue (MB) and big | MB and small | High Blue (HB) and big | HB and small |
|---|---|---|---|---|---|---|
| High Red (HR) | HR (LB) big | HR (LB) small | HR (MB) big | HR (MB) small | HR (HB) big | HR (HB) small |

Table 6 shows how the dynamic decoding approach described herein can be applied to further increase the number of distinguishable populations or encoding states by the addition of two dynamic dimensions related to bead size: an increase in size by swelling or a decrease in size by dissolving. This results in 54 different populations that can be distinguished based upon changes observed (or observed not to occur) after a Defined Event. This gain in potential multiplexing is achievable by measuring only two colors (red and blue) at three intensities (low, medium, and high), and four sizes (big, bigger, small, dissolves/not detected). This encoding scheme can be further expanded by the incorporation of any of the other methods described herein.

TABLE 6

|  | Low Blue (LB) and big | LB and small | Medium Blue (MB) and big | MB and small | High Blue (HB) and big | HB and small |
|---|---|---|---|---|---|---|
| Low Red (LR) | LR (LB) big | LR (LB) small | LR (MB) big | LR (MB) small | LR (HB) big | LR (HB) small |
| Low Red (LR) dissolves | LR (LB) big dissolves | LR (LB) small dissolves | LR (MB) big dissolves | LR (MB) small dissolves | LR (HB) big dissolves | LR (HB) small dissolves |
| Low Red (LR) swells | LR (LB) big swells | LR (LB) small swells | LR (MB) big swells | LR (MB) small swells | LR (HB) big swells | LR (HB) small swells |
| Medium Red (MR) | MR (LB) big | MR (LB) small | MR (MB) big | MR (MB) small | MR (HB) big | MR (HB) small |
| Medium Red (MR) dissolves | MR (LB) big dissolves | MR (LB) small dissolves | MR (MB) big dissolves | MR (MB) small dissolves | MR (HB) big dissolves | MR (HB) small dissolves |
| Medium Red (MR) swells | MR (LB) big swells | MR (LB) small swells | MR (MB) big swells | MR (MB) small swells | MR (HB) big swells | MR (HB) small swells |
| High Red (HR) | HR (LB) big | HR (LB) small | HR (MB) big | HR (MB) small | HR (HB) big | HR (HB) small |
| High Red (HR) dissolves | HR (LB) big dissolves | HR (LB) small dissolves | HR (MB) big dissolves | HR (MB) small dissolves | HR (HB) big dissolves | HR (HB) small dissolves |
| High Red (HR) swells | HR (LB) big swells | HR (LB) small swells | HR (MB) big swells | HR (MB) small swells | HR (HB) big swells | HR (HB) small swells |

Example 10

FIGS. 20 and 21 show examples of instrumentation that is not array based but utilizes a flow cytometer to make a measurement of a bead before or after a Defined Event. In FIG. 20 solid supports are measured before and after illumination photobleaches an encoding agent or agents. FIG. 21 shows an example where solid supports are measured before and after a sheath flow or additional reagent stream is mixed into the stream containing the beads. This flow can contain an agent such as but not limited to a buffer of a different pH, solvent, or ligand that affects at least one encoding agent or the solid support structure to cause a physical and/or chemical change. A comparison of the optical properties of the solid supports before and after the Defined Event can be used to decode one population or subpopulation from another.

Example 11

Multiplexing bead-based bioassays typically requires that each type of microsphere be uniquely encoded to distinguish one type from another. Microspheres are typically encoded using fluorescent dyes with different spectral properties and varying concentrations. However, practical limits exist on the number of dyes that can be spectrally resolved or the number of distinguishable intensity levels with each dye. To expand the number of encoding levels, a method was developed that incorporates photobleaching kinetics into bead decoding, unlocking additional multiplexing levels unattainable by conventional decoding methods. To demonstrate this technique, beads were encoded with two dyes having overlapping fluorescence excitation and emission wavelengths but different photostabilities. All beads initially exhibited similar fluorescence intensities; however, following appropriate photoexposure, the less photostable dye had reduced emission intensity due to photobleaching. By comparing the original fluorescence emission intensity to that obtained after photobleaching, multiple different populations could be reliably identified. Using only a single excitation/emission band, two different initial intensity levels were optimized to produce six uniquely identifiable bead populations whereas only two could have been achieved with conventional decoding methods. Incorporation of this encoding strategy into bead-based microwell array assays significantly increases the number of encoding levels available for multiplexed assays without increasing the complexity of the imaging instrumentation.

The method incorporated a dynamic element into the decoding process. Rather than using single time-point encoding measurements, the method described herein employs the photobleaching kinetics to distinguish bead populations. Two dyes with overlapping spectral properties, but different photostabilities, were utilized to encode beads that could then be differentiated based on simple photobleaching rate measurements. The methods reported here monitor photobleaching, which occurs on the seconds timescale for these experiments, significantly increasing the multiplexing capacity of bead-based assays without increasing the complexity of the analytical platform.

Materials and Methods

Bead Encoding Procedure

Streptavidin-functionalized ProMag magnetic microspheres, nominally 3 μm in diameter, were purchased from Bangs Laboratories (Fishers, IN). R-phycoerythrin (PE) biotin conjugate and 605 Qdots (QDs) biotin conjugate (Life Technologies; Carlsbad, CA) were used as the encoding dyes for this study. "High" level beads were labeled with 5 nM PE, 250 nM QDs, or an 18 nM PE/22 nM QD mixture. The "low" level beads were labeled with 0.6 nM PE, 4 nM QDs, or a 0.45 nM PE/2 nM QD mixture. The buffer utilized throughout this encoding procedure was comprised of 1× Tris-buffered saline, pH 7.2 (Thermo Scientific; Waltham, MA) and 0.1% Tween 20 (Sigma Aldrich; St. Louis, MO).

A 10 μL aliquot of bead stock solution (2.6% solids) was used for each labeling reaction. Beads were first washed 3× with 100 μL aliquots of buffer, magnetically collected, and then resuspended in 10 μL. Encoding was performed by adding 15 μL of dye solution to the beads and incubating for 1 h at ambient temperature. Dye labeling bead solutions were shielded from light and placed in a rotator (Labnet International; Edison, NJ) to ensure beads remained suspended for the duration of the labeling reaction. After functionalization, beads were washed 3× and then resuspended in 20 μL of buffer and stored at 4° C.

Microwell Array Fabrication

Microwell array chips for these studies were fabricated using silicon and glass. Silicon wafers were purchased from University Wafer (South Boston, MA) and coated with chromium and positive photoresist by NanoFilm (Westlake Village, CA). The array containing 3.5 μm diameter bead wells was photolithographically patterned onto the wafers using a Heidelberg Instruments DWL FS66 laser writer (Heidelberg, Germany). Following development of the photoresist and removal of the exposed chromium, wafers were etched in an Alcatel AMS 100 deep reactive ion etcher to a depth of ≈5 μm.23 After etching, the remaining photoresist and chromium were removed from the wafer. SU-8 2050 (MicroChem; Westborough, MA) was then patterned onto the wafer to form the outer fluidic boundaries of the device. To complete the microchip, a glass substrate containing vias for fluid and bead access was aligned over the silicon array and epoxied into place (Loctite 120 HP). Once bonded, chips were treated with a 1% trichloro(octyl)silane (Sigma Aldrich) in heptane (Fisher Scientific; Pittsburgh, PA) to render the surfaces hydrophobic.

Encoding Experiments

Microchips were conditioned with a buffer containing 20 mM Tris, pH 8.0 (Life Technologies), 50 mM KCl (Life Technologies), 2.5 mM MgCl2 (Fluka; St. Louis, MO), 0.1% Tween 20, and 1% bovine serum albumin (Thermo Scientific). Beads were pipetted into a via and pulled over the array magnetically where uniform loading was achieved throughout the chip. Following loading, chips were sealed with Krytox oil (DuPont; Wilmington, DE) to isolate individual wells from each other. Sealed chips were kept in darkness until ready for imaging.

The imaging system utilized in these experiments was comprised of a Nikon AZ100 fluorescence microscope (Melville, NY), a Prior Scientific Lumen 200 Pro fluorescence illumination system (Rockland, MA), and a Hamamatsu ORCA Flash 4.0 CMOS camera (Middlesex, NJ). Loaded chips were placed on the microscope stage and 2 s exposures were acquired every 2.5 s using Micro-Manager software. The excitation source shutter was fully open only during the exposure. Subsequent data plots in this manuscript display x-axis time points as real time (i.e. 2.5 s per image) rather than exposure time (i.e. 2 s per image). Images for both PE- and QD-encoded beads were acquired using a single filter set (545/30 nm excitation, 620/60 nm emission).

To evaluate bleaching behavior, replicate chips were loaded with a single bead type and repeatedly imaged. This was conducted for all bead populations. The resulting images were processed with FIJI software.26 After the location of each bead in the array wells was determined, fluorescence signals were ascertained throughout the set of images. The fluorescence intensity was plotted as a function of optical irradiance exposure time to compare population decay profiles. For histogram analysis, normalized intensity values from the final three images terminating at a given time point (e.g. when evaluating 90 s of exposure, the t=80 s, 85 s, and 90 s images were utilized) were averaged to minimize fluctuations in the signal and reduce noise. These endpoint decay values were then sorted to determine appropriate histogram bin ranges specific to each bead population.

Results and Discussion

Photobleaching Rates

Differences in the photostabilities of quantum dots and organic dyes offer an intriguing opportunity for encoding microspheres when they have sufficiently overlapping excitation or emission maxima. The fluorescent protein phycoerythrin has a high fluorescence quantum yield but is susceptible to photobleaching upon prolonged photoexposure. In contrast, quantum dots are generally resistant to photobleaching and maintain (or even increase) their observed emission following additional exposure. By encoding one bead set with PE and another with QDs, it was hypothesized that the initial fluorescence between the two populations would appear the same, but that they could be distinguished after extended exposure. Introduction of photobleaching kinetics into such encoding measurements would therefore enable additional encoding levels to be achieved for increased multiplexing unattainable by conventional, single-image decoding methods.

Bead sets encoded with PE, QDs, or a mixture of both dyes were loaded into microwell array chips and repeatedly imaged. Inspection of the resulting images illustrated that beads underwent a differential change following prolonged imaging (see, e.g., FIGS. 3A, 3B, and 3C). As predicted, beads encoded with PE experienced significant reduction in fluorescence signal as the dye bleached over the course of 3 min while the fluorescence signal from the QD-encoded beads was largely unaffected by photoexposure over the same duration. Beads labeled with a mixture of both dyes exhibited a moderate decrease in fluorescence signal that was less severe than the PE-encoded population. A plot of the fluorescence decay profiles shows good resolution between each bead set. Very similar bleaching rates were observed within each bead population indicating high precision for this dynamic decoding approach.

Bleaching Duration and Population Overlap

Figure 22:
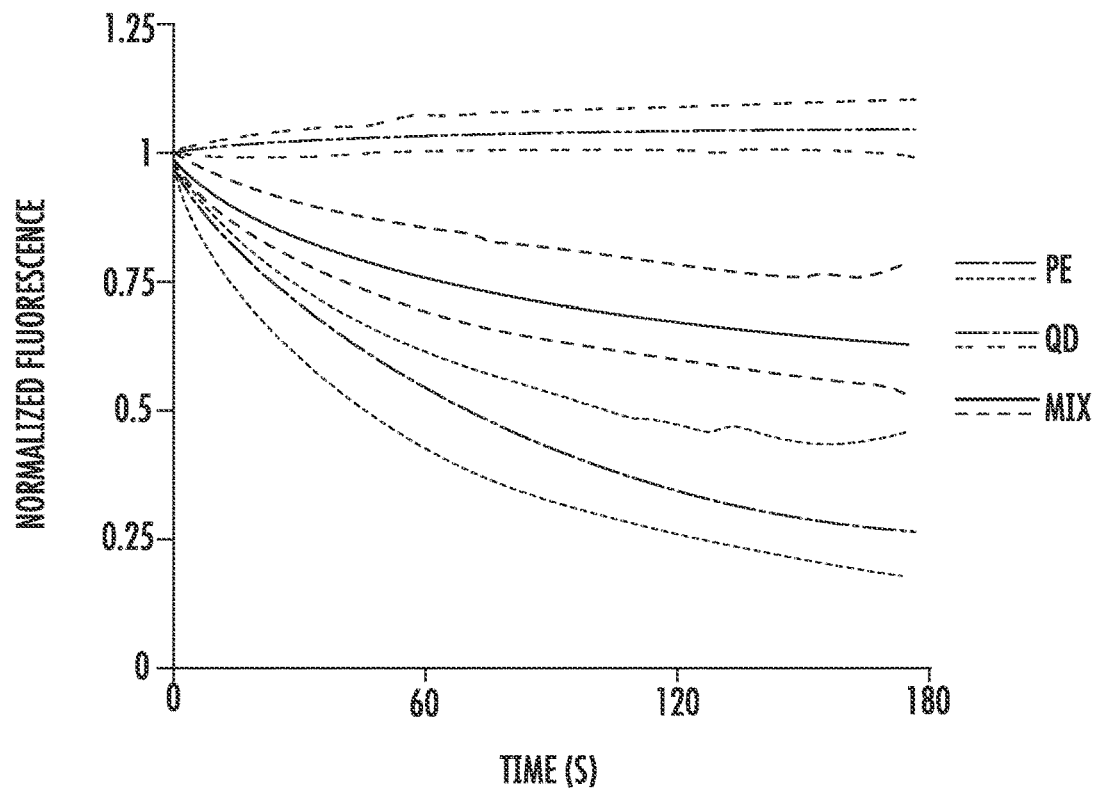
FIG. 22 is a graph of average fluorescence values over time for each population with the top and bottom 5% of fluorescence values plotted using dashed lines.

Although the average fluorescence decay profiles of each bead set were quite distinct from one another, each population exhibited variance in photobleaching. Consequently, the boundaries of each population were inspected to verify that they did not overlap with one another in order to avoid bead misidentification. FIG. 22 illustrates the photobleaching profiles from the top and bottom 5% of beads from each population. These traces show that not only is the average decay of each bead population well-resolved from one another, but the range within each group is resolved as well. FIG. 22 also suggests that 3 min of photobleaching under these conditions is somewhat excessive since each population appears to be identifiable in a shorter time period.

Given that both throughput and performance of bioassays will benefit from a reduction in decoding time, the minimum photobleaching duration required to obtain acceptable resolution between populations was sought within the parameters of our experimental setup. Endpoint fluorescence values for individual beads were binned into histograms after different lengths of photobleaching, where bleaching was characterized as "fast" (PE beads), "moderate" (Mix beads), and "slow" (QD beads) (Table 7). Each population had >50 k beads in the data set (n=5 chips) to provide a sufficiently large sample size to accurately represent the population distribution. Decoding data revealed that the different bead sets were fairly well resolved within 30 s, although some overlap was still observed between the Mix beads and the other populations. The maximum misidentification after 30 s of bleaching was 1.7%, occurring between the PE and Mix beads. While this error may be acceptable for certain applications where a small amount of misidentification is tolerable, it is too high for many digital, low LOD assays. In general, the percentage of bead misidentification should be less than the noise of the bioassay to ensure it does not significantly impact the measurement precision. Additionally, this short bleaching time required that 2.5% of both PE and Mix beads be excluded from the data set because they exhibited fluorescence in overlap regions between adjacent bead populations. Removing this fairly small percentage of beads was found to significantly improve identification accuracy and remove ambiguity from the analysis.

Extending the photobleaching duration increased resolution between the bead populations (Table 7). After 1.5 min of bleaching, identification accuracy increased to >99.9% with <0.8% of beads excluded due to ambiguity. However, diminishing returns were observed when bleaching time was further extended. Identification accuracy following 3 min of bleaching was >99.98% while the exclusion rate was <0.3%. Although superior, the extra resolution was deemed superfluous for most bioassays where non-specific binding causes a background signal of 0.1-1%.7 Due to the combination of high encoding accuracy, low exclusion rate, and faster throughput, photoexposure times of 1.5 min were deemed optimal for bead decoding under these experimental parameters. Other systems with higher intensity lamps, broader band-pass filter sets, etc. may be used to reduce this time further.

TABLE 7

The percentages of beads in each population were sorted into three photobleaching bins ("fast", "moderate", and "slow") based on endpoint fluorescence decay. The percentage of misidentified beads diminished as bleaching time was increased. Beads exhibiting decay values in ambiguous overlap regions between populations were omitted ("excluded") from the data sets.

| Bleaching | 0.5 min | | | 1.5 min | | | 3 min | | |
| --- | --- | --- | --- | --- | --- | --- | --- | --- | --- |
| Bin | PE | Mix | QD | PE | Mix | QD | PE | Mix | QD |
| Fast | 97.19 | 1.67 | 0 | 99.14 | 0.087 | 0 | 99.89 | 0.018 | 0 |
| Moderate | 0.304 | 95.78 | 0.024 | 0.084 | 99.26 | 0.004 | 0.015 | 99.68 | 0 |

TABLE 7-continued

The percentages of beads in each population were sorted into three photobleaching bins ("fast", "moderate", and "slow") based on endpoint fluorescence decay. The percentage of misidentified beads diminished as bleaching time was increased. Beads exhibiting decay values in ambiguous overlap regions between populations were omitted ("excluded") from the data sets.

| Bleaching | 0.5 min | | | 1.5 min | | | 3 min | | |
|---|---|---|---|---|---|---|---|---|---|
| Bin | PE | Mix | QD | PE | Mix | QD | PE | Mix | QD |
| Slow | 0 | 0.050 | 99.89 | 0 | 0.016 | 99.96 | 0 | 0.020 | 99.99 |
| Excluded | 2.50 | 2.51 | 0.085 | 0.773 | 0.639 | 0.036 | 0.100 | 0.280 | 0.013 |

Additional Encoding States

To further enhance the number of encoding states with this dynamic decoding technique, new sets of beads at a lower initial intensity level were developed using lower dye concentrations ("low" beads). The amounts of each dye were optimized to obtain similar initial fluorescence values for the three bleaching-distinguishable bead types (PE, QD, and Mix, as before) while also ensuring they underwent a resolvable degree of photobleaching decay. Following optimization of dye concentrations, bleaching profiles for three populations were measured. Each bead population exhibited similar normalized photobleaching to its corresponding profile the "high" intensity beads described in the previous section) with high precision. Histograms were constructed to measure the overlap between these "low" intensity bead populations after bleaching. Overlap between the three bead sets was indicating that "low" intensity level beads perform as well as "high" intensity beads, and both can be readily implemented into multiplexed bead assays.

While optimizing dye concentrations, care was taken to ensure the "low" intensity populations did not overlap in initial intensity with the "high" encoding populations. This is crucial since normalized decay cannot be used to distinguish between beads encoded with the same dye. Sorting the data into histograms validated that the "high" and "low" intensity levels demonstrated no overlap. It can also be seen that the wide range in fluorescence values of the "high" population makes it difficult to achieve an intermediate encoding level, a common limitation that precludes high degrees of multiplexing with conventional bead encoding approaches. However, with the incorporation of the time domain, multiple additional encoding levels were attained despite the high variance in initial intensity.

Figure 23:
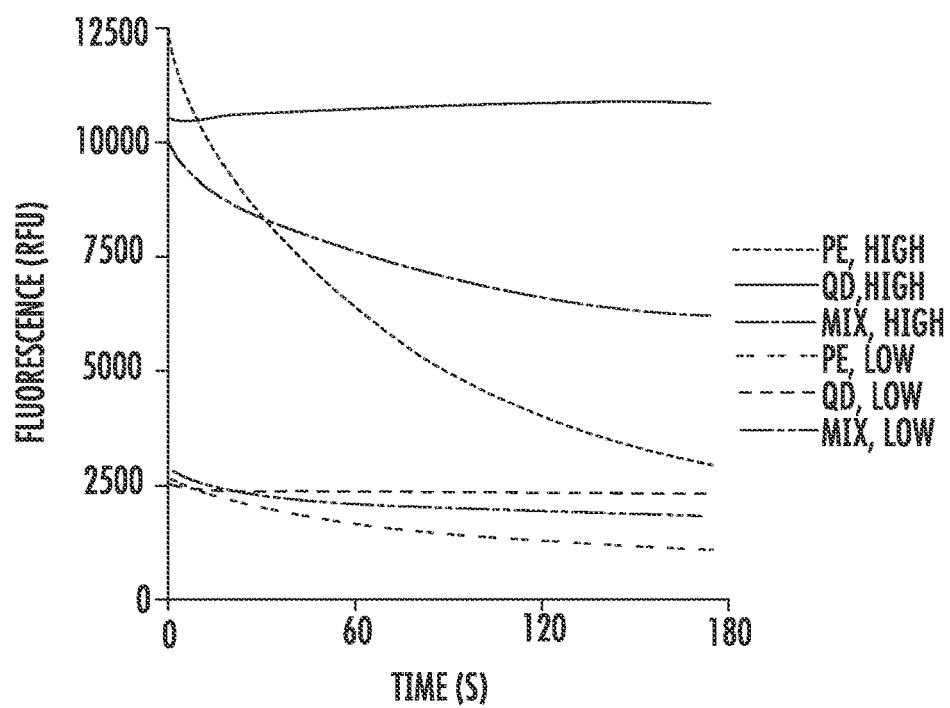
FIG. 23 is a graph of raw fluorescence intensity data over time from the six encoded bead populations. Initial fluorescence values distinguish the "high" and "low" populations from one another while photobleaching determines the specific encoding dye(s) used.

Ultimately, combining beads of two intensity levels ("high" and "low"), each with three distinguishable sub-populations (PE, QD, and Mix), enabled a total of six distinct encoding states to be achieved with single wavelength detection. Individual beads were first assigned to the "high" or "low" bins based on the t=0 fluorescence and then repeatedly imaged to identify the specific encoding dye(s) used (FIG. 23). This approach was shown to significantly enhance the multiplexing capability of bead-based POC assays compared to conventional encoding approaches while also minimizing cost and complexity of the assay optical system.

Theoretical Considerations

Standard encoding is typically based upon a single time point observation of wavelengths and intensities. The number of available encoding states is determined by the number of distinguishable populations for each excitation/emission band and can be expressed according to the following equation for three bands:

$$T_{conventional}=(n_i+1)*(n_j+1)*+(n_k+1)$$

where $T_{conventional}$ is the total number of encoding states, $n_i$, $n_j$, and $n_k$ are the number of encoded intensity levels in excitation/emission bands I, J, and K, respectively. The lowest level of fluorescence is the level 0, or non-encoded, where the presence of an encoding dye cannot be detected.

Mixing two or more dyes with similar spectral properties, but different stabilities, provides additional states of encoding within the distinguishable fluorescence intensity levels. Two spectrally similar dyes can be mixed together at different ratios to achieve 0-5 encoding levels. The lowest level, 0, uses no dye. The next level, 1, can use one equivalent of either the stable or the labile dye. Level 2 can use two equivalents of either dye or a mix of one equivalent of each dye. It can be observed that for band I, for each intensity level i, there are i+1 dye combinations that will react differently to photoexposure. The total number of available encoding states ($T_{dynamic}$) can be expressed as a function of the number of distinguishable fluorescence levels:

$$T_{dynamic}=(\Sigma_{i=0}^{n_i}(i+1))*(\Sigma_{j=0}^{n_j}(j+1))*(\Sigma_{k=0}^{n_k}(k+1))$$

where i, j, and k represent intensity levels in excitation/emission bands I, J and K. For five different encoding levels and three excitation/emission bands, a traditional single time point measurement will yield 216 unique encoding states. Using a time-domain approach with five different intensity levels results in 21 different types of uniquely encoded beads and the theoretical number of unique encoding states for three excitation/emission bands is 9,261.

Prophetic Example 12

The photostability of organic dyes in the time domain may be used to decode a biological sample. A first antibody may include a first organic dye attached thereto and a second antibody may include a second organic dye attached thereto. A third antibody may include both the first and second organic dyes attached thereto in different ratios as described above. The first and second organic dyes may have the same and/or similar fluorescence excitation/emission properties and/or intensities such that the first, second, and additional antibodies are indistinguishable at the first point in time prior to the Defined Event. The first and second organic dyes may be susceptible to different levels of photobleaching upon exposure to light for a defined time, typically between about 30 seconds and five minutes, such as about 1 minute, about 2 minutes, about 3 minutes or more. Thus, after photobleaching for the defined time, e.g., at least one microsecond, the different antibodies have different fluorescence intensities. For example, the first organic dye may be not as susceptible (i.e., more stable) to photobleaching compared to the second organic dye (i.e., the dynamic element) and the fluorescence intensity for the first organic dye may only reduce by 10% after 1 minute, whereas the fluorescence intensity for the second organic dye may reduce by 90% after 1 minute. Thus, the first and second antibody populations may be identified by the fluorescence intensity after the Defined Event (i.e., photobleaching). The third antibody population may also be identified by the fluorescence intensity after the Defined Event as the ratio provides different levels or a gradient of fluorescence intensities between the intensities for the first and second organic dyes. A biological sample (e.g., a tissue) may be contacted with the first, second and third antibodies. Each of the encoded antibodies may bind to a portion of the sample. The fluorescence intensity at different locations on the sample may be compared at different time points to identify the location of each antibody in and/or on the sample, and may be used to identify what elements are present in a sample and/or where the elements are in a sample.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A plurality of solid supports comprising:
   a first population of solid supports comprising at least one encoding agent at a first concentration; and
   a second population of solid supports comprising the at least one encoding agent at a second concentration and at least one additional encoding agent,
   wherein the second population of solid supports comprises the at least one encoding agent at a ratio to the at least one additional encoding agent, and
   wherein the fluorescence excitation and emission wavelengths for the at least one encoding agent and the at least one additional encoding agent respectively overlap, and
   wherein the at least one encoding agent has a different stability in response to a defined event that causes a physical and/or chemical change in an encoding signal associated with the at least one encoding agent compared to the at least one additional encoding agent such that the population of solid supports encoded with the at least one encoding agent is distinguishable from the population of solid supports encoded with the at least one additional encoding agent after the defined event, and further wherein the defined event is a thermal, optical, or chemical event.

2. The plurality of solid supports of claim 1, wherein the at least one encoding agent is stable and the at least one additional encoding agent is unstable in response to the defined event.

3. The plurality of solid supports of claim 1, further comprising a third population of solid supports, and respective solid supports in the third population comprise an encoding agent that does not have a fluorescence excitation and emission wavelength that overlaps with the at least one encoding agent or the at least one additional encoding agent.

4. The plurality of solid supports of claim 1, wherein the at least one encoding agent and/or the at least one additional encoding agent comprises a dye, fluorescent protein, or quantum dot.

5. The plurality of solid supports of claim 1, wherein defined event is a thermal event.

6. The plurality of solid supports of claim 1, wherein the plurality of solid supports comprises at least 20 differently encoded solid supports.

7. The plurality of solid supports of claim 6, wherein the plurality of solid supports encodes at least 1,000 encoding states that are detectable.

8. A kit comprising the plurality of solid supports of claim 1.

9. The kit of claim 8, further comprising a microfluidic device.

10. The plurality of solid supports of claim 1, wherein the at least one encoding agent and the at least one additional encoding agent have different photostabilities.

11. The plurality of solid supports of claim 1, wherein the at least one additional encoding agent and the at least one encoding agent have different photobleaching kinetics.

12. The plurality of solid supports of claim 1, wherein the ratio is a ratio of the at least one encoding agent:the at least one additional encoding agent of 25:75, 50:50, or 75:25.

13. The plurality of solid supports of claim 1, wherein the plurality of solid supports comprises a primer or probe that is coupled to solid supports in the first population of solid supports and/or solid supports in the second population of solid supports, wherein the at least one encoding agent is attached to the primer or probe.

14. The plurality of solid supports of claim 1, wherein the plurality of solid supports comprises an antibody that is coupled to solid supports in the first population of solid supports and/or solid supports in the second population of solid supports, wherein the at least one encoding agent is attached to the antibody.

15. The plurality of solid supports of claim 1, wherein the plurality of solid supports comprises a peptide or protein that is coupled to solid supports in the first population of solid supports and/or solid supports in the second population of solid supports, wherein the at least one encoding agent is attached to the peptide or protein.

16. The plurality of solid supports of claim 1, wherein the plurality of solid supports comprises an aptamer that is coupled to solid supports in the first population of solid supports and/or solid supports in the second population of solid supports, wherein the at least one encoding agent is attached to the aptamer.

17. The plurality of solid supports of claim 1, wherein the plurality of solid supports comprises an oligonucleotide that is coupled to solid supports in the first population of solid supports and/or solid supports in the second population of solid supports, wherein the at least one encoding agent is attached to the oligonucleotide.

* * * * *

UNITED STATES PATENT AND TRADEMARK OFFICE
CERTIFICATE OF CORRECTION

| | | |
|---|---|---|
| PATENT NO. | : 12,146,876 B2 | Page 1 of 1 |
| APPLICATION NO. | : 17/244257 | |
| DATED | : November 19, 2024 | |
| INVENTOR(S) | : Ramsey et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 556 days.

Signed and Sealed this
Sixth Day of May, 2025

Coke Morgan Stewart
*Acting Director of the United States Patent and Trademark Office*